US011932726B2

(12) United States Patent
Culbertson et al.

(10) Patent No.: US 11,932,726 B2
(45) Date of Patent: Mar. 19, 2024

(54) METHOD OF MAKING RELEASABLE POLYMERIC REAGENTS

(71) Applicant: Nektar Therapeutics, San Francisco, CA (US)

(72) Inventors: Sean M. Culbertson, Gurley, AL (US); Samuel P. McManus, Huntsville, AL (US); Antoni Kozlowski, Huntsville, AL (US); Venkata Ravidnranadh Somu, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 522 days.

(21) Appl. No.: 17/284,378

(22) PCT Filed: Oct. 11, 2019

(86) PCT No.: PCT/US2019/055971
§ 371 (c)(1),
(2) Date: Apr. 9, 2021

(87) PCT Pub. No.: WO2020/077289
PCT Pub. Date: Apr. 16, 2020

(65) Prior Publication Data
US 2021/0388161 A1    Dec. 16, 2021

Related U.S. Application Data

(60) Provisional application No. 62/744,512, filed on Oct. 11, 2018.

(51) Int. Cl.
*C08G 65/333* (2006.01)
*A61K 47/60* (2017.01)
*C08G 65/30* (2006.01)

(52) U.S. Cl.
CPC ........ *C08G 65/33396* (2013.01); *A61K 47/60* (2017.08); *C08G 65/30* (2013.01)

(58) Field of Classification Search
CPC ........ C08G 65/33396; C08G 65/33337; A61K 47/60
See application file for complete search history.

(56) References Cited

U.S. PATENT DOCUMENTS

| 8,252,275 B2 | 8/2012 | Bentley et al. |
| 8,604,159 B2 | 12/2013 | McManus et al. |
| 8,905,235 B2 | 12/2014 | Culbertson et al. |
| 9,334,364 B2 | 5/2016 | Kozlowski et al. |
| 10,421,838 B2 | 9/2019 | Kozlowski et al. |
| 2010/0048707 A1* | 2/2010 | Culbertson ............ C08F 32/08 526/280 |
| 2012/0318701 A1 | 12/2012 | Culbertson et al. |
| 2013/0225789 A1 | 8/2013 | Sun et al. |

FOREIGN PATENT DOCUMENTS

| EP | 3 279 236 A1 | 2/2018 |
| WO | WO 01/45796 A2 | 6/2001 |
| WO | WO 2007/016560 A3 | 2/2007 |

OTHER PUBLICATIONS

Dujardin et al., "Ion-exchange resins bearing thiol groups to remove mercury. Part 1: synthesis and use of polymers prepared from thioester supported resin", Reactive and Functional Polymers, vol. 43, pp. 123-132, (2000).
Meng et al., "Stepwise and Concerted Solvolytic Elimination and Substitution Reactions: E1 Reaction via a Primary Carbocation", J. Am. Chem. Soc., vol. 119, pp. 4834-4840, (1997).
Pangborn et al., "Safe and Convenient Procedure for Solvent Purification", Organometallics, vol. 15, pp. 1518-1520, (1996).
Shechter et al., "Reversible pegylation of insulin facilitates its prolonged action in vivo", European Journal of Pharmaceutics and Biopharmaceutics, vol. 70, pp. 19-28, (2008).
Tripp et al., "Reactive Filtration": Use of Functionalized Porous Polymer Monoliths as Scavengers in Solution-Phase Synthesis, Organic Letters, vol. 2, No. 2, pp. 195-198, (2000).
Williams et al., "Drying of Organic Solvents: Quantitative Evaluation of the Efficiency of Several Desiccants", J. Org. Chem., vol. 75, pp. 8351-8354, (2010).
PCT International Search Report and Written Opinion corresponding to PCT Application No. PCT/US2019/055971 dated May 11, 2020.
PCT International Preliminary Report on Patentability corresponding to PCT Application No. PCT/US2019/055971 dated Apr. 22, 2021.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003—1$^{st}$, (Jan. 2003).
NOF Corporation, PEG Derivatives, Phospholipid and Drug Delivery Materials for Pharmaceuticals, 27 pages, Catalogue 2003—2$^{nd}$, (Mar. 2004).

(Continued)

*Primary Examiner* — Jeffrey C Mullis
(74) *Attorney, Agent, or Firm* — Susan T. Evans

(57) ABSTRACT

The instant disclosure provides (among other things) improved methods of preparing fluorenyl-based polymeric reagents, methods of recovering and purifying such polymeric reagents, methods of reducing unwanted impurities in a fluorenyl-based polymeric reagent, fluorenyl-based polymeric reagents prepared by the methods described herein, and conjugates prepared by reaction with fluorenyl-based polymeric reagents prepared by the methods described herein.

81 Claims, No Drawings

(56) References Cited

OTHER PUBLICATIONS

NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).

* cited by examiner

METHOD OF MAKING RELEASABLE POLYMERIC REAGENTS

CROSS REFERENCE TO RELATED APPLICATIONS

This application is a 35 U.S.C. § 371 application of International Application No. PCT/US2019/055971, filed on Oct. 11, 2019, designating the United States, which claims the benefit of priority under 35 U.S.C. § 119(e) to U.S. Provisional Patent Application No. 62/744,512, filed on Oct. 11, 2018, the disclosure of which is incorporated herein by reference in its entirety.

FIELD

The instant application relates to (among other things) improved methods of preparing fluorenyl-based polymeric reagents, methods of recovering and purifying such polymeric reagents, methods of reducing unwanted impurities in a fluorenyl-based polymeric reagent, fluorenyl-based polymeric reagents prepared by the methods described herein, and conjugates prepared by reaction with fluorenyl-based polymeric reagents prepared by the methods described herein.

BACKGROUND

Modification of bioactive molecules by covalent attachment of polyethylene glycol can enhance the pharmacological and pharmaceutical properties of such molecules and has been used successfully in several approved drugs. For example, PEGylation has been used to create marketed drugs in which a biopharmaceutical agent is covalently attached to polyethylene glycol with a stable bond, such as, for example, CIMZIA® (PEGylated tumor necrosis factor (TNF)), NEULASTA® (PEGylated granulocyte-colony stimulating factor (GCSF)), PEGASYS® (PEGylated interferon α-2a), and ADYNOVATE® (PEGylated Factor VIII). In many cases, stable covalent attachment of one or more polyethylene glycol chains to an active agent results in PEG conjugates having reduced functional activity when compared to the unmodified molecule. When an active drug is covalently attached to a polymer via a stable linkage, the polymer-bound drug may retain the properties of the unbound drug, although its efficacy per gram of drug generally differs from the unmodified drug, since the covalently attached polymer can change, among other things, the steric and electronic environment surrounding the drug molecule, and can render the drug less effective (on a per gram basis of drug). However, this effect can be offset in certain instances, by, for example, a longer circulation time such that enhanced drug efficacy may be achieved.

PEGylation technologies also exist in which a PEG reagent is covalently attached to a therapeutic agent via a releasable linkage. Releasable PEGylation (in some instances also referred to as "reversible PEGylation"), is a technology in which an active agent conjugate (which includes a drug molecule that is releasably chemically bonded to one or more water-soluble polymer moieties such as polyethylene glycol), following administration, releases the one or more polymer moieties from the drug over time, through a chemical process that occurs in vivo. Such releasably-polymer modified drugs are sometimes referred to as pro-drugs, since in theory, the polymer(s) is/are released over time in the circulation and the activity of the parent drug molecule can be recovered. The efficacy of releasable drug delivery systems can be affected by, e.g., the release rate of one or more covalently attached polymer moieties from a drug conjugate.

One class of PEGylation reagents that may be used to form drug conjugates capable of undergoing reversible (releasable) PEGylation is based on the fluorenylmethyl-oxycarbonyl (FMOC) amine protecting group (see, e.g., Wuts, P. G., Greene, T. W., *Protective Groups in Organic Synthesis,* Fourth Ed., 2007, John Wiley & Sons, Inc., New Jersey; Bentley, M. D., et al., U.S. Pat. No. 8,252,275; Shechter Y., et al., *Eur J. Pharm Biopharm,* 2008, 70, 19-28). A generalized structure of one particular class of these reagents, referred to herein as polymeric, or in some particular instances, PEGylated FMOC reagents, possessing a branched architecture, is shown in Structure X below (as described, for example, in Bentley, M. D., et al., U.S. Pat. No. 8,252,275, incorporated herein by reference in its entirety, where descriptions for L1 and L2, and $R^{e1}$ and $R^{e2}$ are provided therein). In this illustrative structure, the polymeric reagent is activated as an N-hydroxyl succinimidyl carbonate (NETS) ester, i.e., comprises a succinimidyl carbonate ester leaving group.

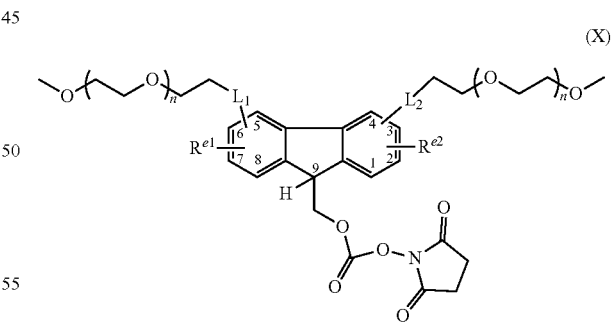

(X)

The PEG2 FMOC reagents may be reacted with a therapeutic agent comprising a nucleophilic atom capable of reacting with an FMOC-type reagent to form, for example, a carbamate adduct. This reaction scheme is illustrated below, showing, as an example, reaction of a protein lysine group with a generalized form of an exemplary PEG2-FMOC reagent comprising a reactive N-succinimidyl carbonate group (Scheme I).

Scheme I.

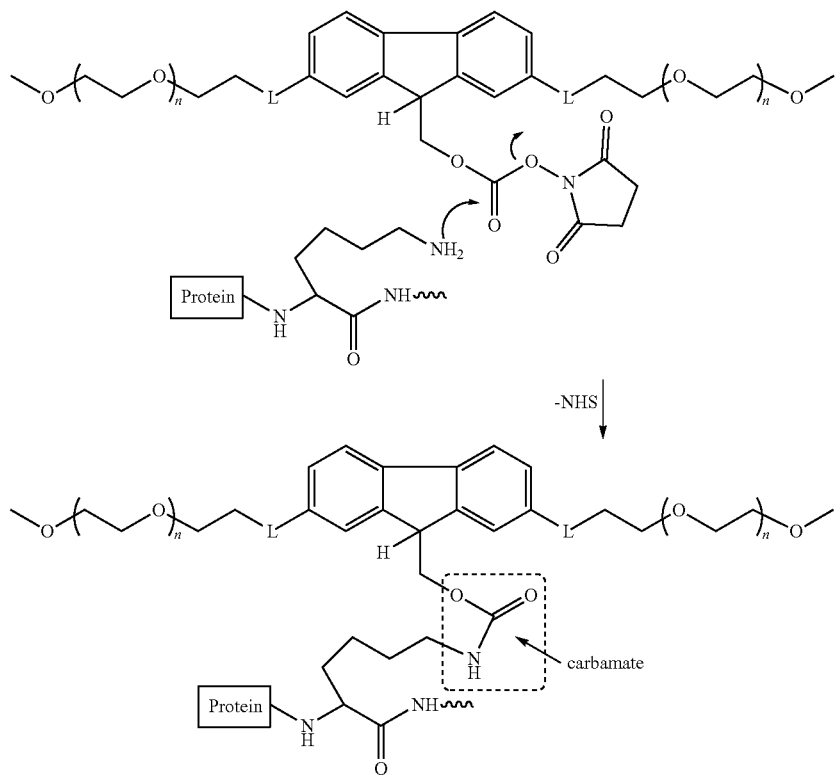

During the manufacturing of various FMOC reagents by previously described synthetic approaches, the Applicants have experienced unwanted side reactions. These side reactions can result in the formation of undesirable side products that (i) can potentially adversely impact the quality of the final polymer-therapeutic agent conjugate, and (ii) may alter the mechanism of release of the FMOC polymer moiety (or moieties) from the therapeutic agent. The instant disclosure describes challenges associated with previously described methods of preparing the subject polymeric FMOC reagents, and provides several process improvements aimed at overcoming such problems, to thereby provide, for example, improved methods of making the polymeric FMOC reagents, improved methods for making intermediates useful in preparing the polymeric FMOC reagents, improved methods for activating an FMOC intermediate, methods for removing one or more undesirable polymeric FMOC-derived side-products or impurities, and methods for stabilizing certain polymeric FMOC reagents, among other things. Thus, the present disclosure seeks to address these and other challenges related to the preparation of the subject polymeric FMOC reagents and their conjugates.

SUMMARY

In a first aspect, provided herein is a method, i.e., an improved method, for preparing a reactive polymeric reagent. The method comprises (i) reacting a water-soluble 9-hydroxymethyl fluorene polymer having a structure (I):

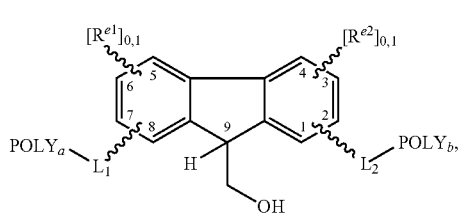

wherein $POLY_a$ is a first water-soluble, non-peptidic polymer; $POLY_b$ is a second, water-soluble non-peptidic polymer; $R^{e1}$, when present, is a first electron-altering group; and $R^{e2}$, when present, is a second electron-altering group; $L_1$ is a first linking moiety; and $L_2$ is a second linking moiety;

with dibenzotriazolyl carbonate (BTC) in an aprotic organic solvent in the presence of a base under anhydrous conditions to provide a reaction mixture comprising a water-soluble 9-methyl benzotriazolyl carbonate fluorene polymer having a structure:

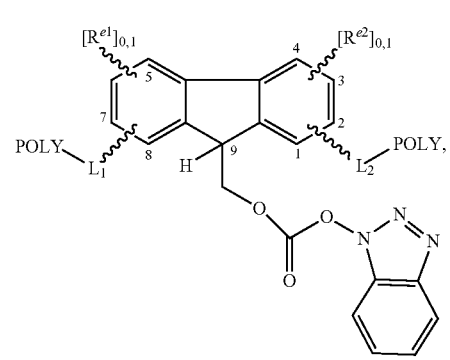

wherein POLY$_a$, POLY$_b$, R$^{e1}$, R$^{e2}$, L$_1$, and L$_2$ each have values as described in step (i), and (ii) recovering the water-soluble 9-methyl benzotriazolyl carbonate fluorene polymer (II) by precipitation with an anhydrous solvent effective to promote precipitation of the water-soluble 9-methyl benzotriazolyl carbonate fluorene polymer.

In one or more embodiments related to the method, in step (i) the water-soluble 9-hydroxymethyl fluorene polymer of structure (I) is reacted with less than about 30 equivalents of dibenzotriazolyl carbonate (di-BTC).

In some embodiments, the base is an amine. In some further embodiments, the base is a non-nucleophilic amine or is a weakly nucleophilic amine. Bases, include, for example, pyridine, 4-dimethylaminopyridine, N,N-diisopropylethylamine, 2,6-di-tert-butylpyridine, N-methylimidazole, N-methylmorpholine, 2,6-lutidine, 2,4,6-collidine, N,N,2,6-tetramethylpyridine-4-amine, and insoluble-polymer-bound forms of any of the foregoing. The amine may also be a polyamine such as, for example, N,N,N',N'-tetramethyl-1,6-hexamethyldiamine, N,N', N', N'',N''-pentamethyldiethylenetriamine, and hexamethylenetetramine.

In one or more embodiments of the method, in step (ii), the anhydrous solvent effective to promote precipitation further comprises an acid.

In yet some further embodiments, the method further comprises, prior to the reacting step, dissolving the water-soluble 9-hydroxymethyl fluorene polymer of structure (I) in the aprotic organic solvent to form a polymer solution, and drying the polymer solution by azeotropic distillation to provide a polymer solution having a water content of less than about 500 ppm.

In some additional embodiments, the recovered water-soluble 9-methyl benzotriazolyl carbonate fluorene polymer from step (ii) comprises less than 10 mole percent of a water-soluble fulvene polymer.

In yet some other embodiments of the method, the recovering step comprises filtering the reaction mixture from step (i) to remove solids to provide a solution comprising the water-soluble 9-methyl benzotriazolyl carbonate fluorene polymer, followed by adding an amount of an anhydrous solvent effective to precipitate the water-soluble 9-methyl benzotriazolyl carbonate fluorene polymer from the solution.

In yet some additional embodiments, the anhydrous solvent effective to promote precipitation of the water-soluble 9-methyl benzotriazolyl carbonate fluorene polymer comprises a small amount of acid.

Yet in some further embodiments, the method comprises washing the recovered water-soluble 9-methyl benzotriazolyl carbonate fluorene polymer with an anhydrous solvent in which the water-soluble 9-methyl benzotriazolyl carbonate fluorene polymer is insoluble or is substantially insoluble, the solvent comprising from about 0.0001 to about 0.5 mole percent acid.

In some further embodiments, the method further comprises (iii) purifying the recovered water-soluble 9-methyl benzotriazolyl carbonate fluorene polymer.

In a second aspect, provided herein is a method comprising converting a recovered or purified water-soluble 9-methyl benzotriazolyl carbonate fluorene polymer as described above to a different reactive carbonate, such as, e.g., a water-soluble 9-methyl N-hydroxy succinimidyl carbonate fluorene polymer, under conditions effective to carry out such transformation. In one or more illustrative embodiments, such conversion is carried out in the presence of dimethylaminopyridine. In yet one or more embodiments, the conversion reaction is carried out in a solvent, such as for example, dichloromethane.

Also provided, in a third aspect, is a method for preparing an N-hydroxyl succinimidyl carbonate ester-activated polymeric reagent. The method comprises (i) reacting a water-soluble 9-hydroxymethyl fluorene polymer having a structure:

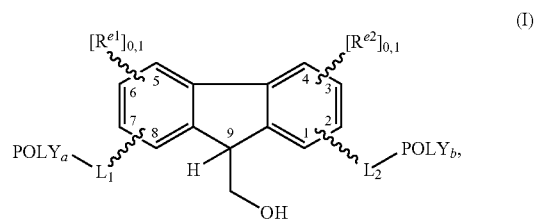

(I)

wherein POLY$_a$ is a first water-soluble, non-peptidic polymer; POLY$_b$ is a second, water-soluble non-peptidic polymer; R$^{e1}$, when present, is a first electron-altering group; R$^{e2}$, when present, is a second electron-altering group; L$_1$ is a first linking moiety; L$_2$ is a second linking moiety; R$^{e1}$, which may or may not be present, is a first electron-altering group; and R$^{e2}$, which may or may not be present, is a second electron-altering group, with from about 1 to 20 equivalents of disuccinimidyl carbonate in an anhydrous aprotic organic solvent in the presence of base to provide a reaction mixture comprising a water-soluble 9-methyl N-succinimidyl carbonate fluorene polymer having a structure:

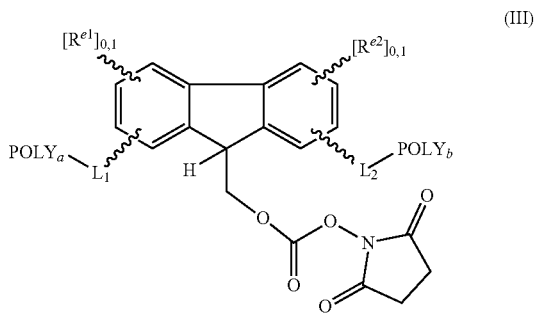

(III)

wherein POLY$_a$, POLY$_b$, R$^{e1}$, R$^{e2}$, L$_1$, and L$_2$ each have values as described in step (i); and (ii) recovering the water-soluble 9-methyl N-hydroxysuccinimidyl carbonate fluorene polymer of structure (III) from the reaction mixture.

Exemplary water-soluble 9-methyl N-hydroxysuccinimidyl carbonate fluorene polymers include the following, structures XI-XIV, wherein mPEGO~ is shorthand for methoxypolyethylene glycol or CH$_3$O(CH$_2$CH$_2$O)$_n$CH$_2$CH$_2$O—, (although any of a number of reactive groups suitable for reaction with a functional group of a target drug molecule can also suitably be envisioned, such as benzotriazolyl carbonate, as can additional water-soluble polymeric chains substituted onto the fluorene core other than polyethylene glycol), wherein each (n) is in a range from about 3 to 2273, including each and every one of the subranges and particular values for (n) described elsewhere herein,

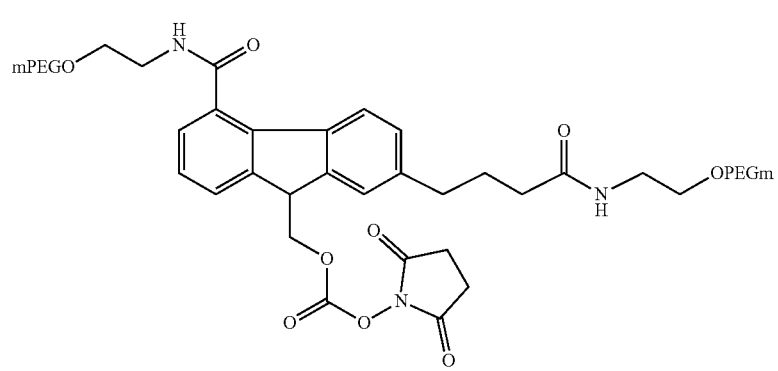
Structure (XI): 9-hydroxymethyl-4-(mPEG-carboxyamide)-7-(3-(mPEGcarbamoyl-propyl)-fluorene-N-hydroxysuccinimidyl carbonate ("CAC-PEG2-FMOC-NHS")
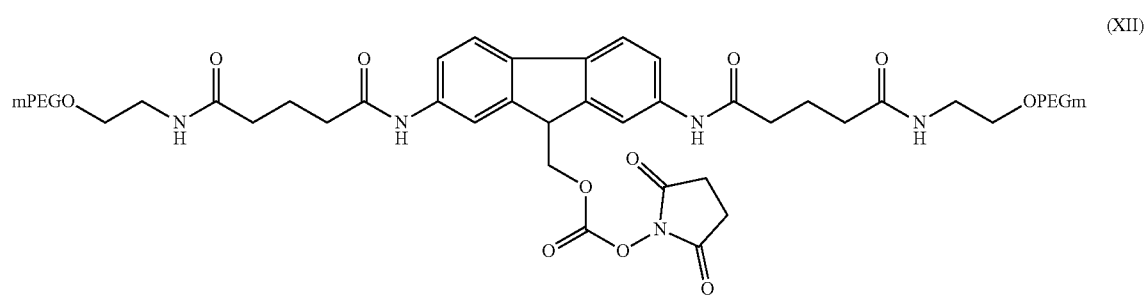
Structure (XII): 9-hydroxymethyl-2,7-di(mPEG-amidoglutaric amide)fluorene-N-hydroxysuccinimidyl carbonate ("G2-PEG2-FMOC-NHS")
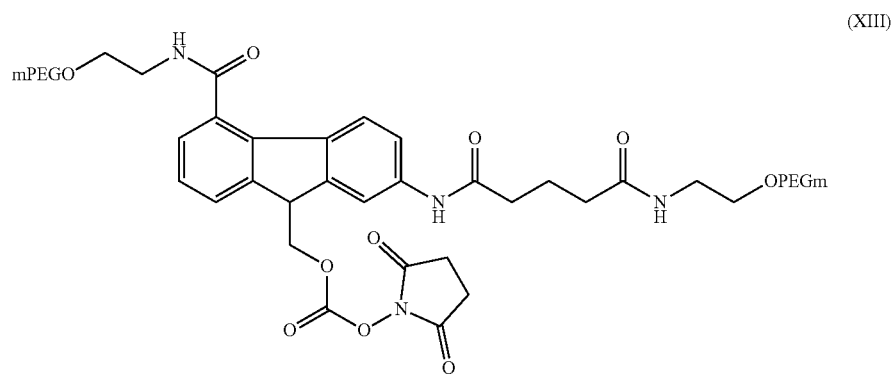

Structure (XIII): 9-Hydroxymethyl-4-(mPEG-carboxyamide)-7-(mPEG amidoglutaric amide)fluorene-N-hydroxysuccinimidyl carbonate ("CG-PEG2-FMOC-NHS") and

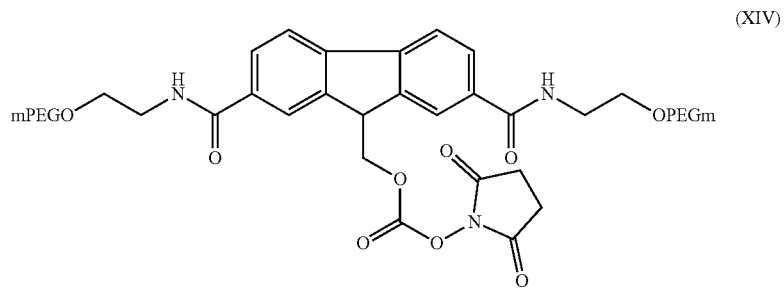

(XIV)

Structure XIV: 9-hydroxymethyl-2,7-(bis-mPEG-carboxyamide)-fluorene-N-hydroxysuccinimidyl carbonate ("C2-PEG2-FMOC-NHS").

In some embodiments of the foregoing method, prior to reacting step (i), the water-soluble 9-hydroxymethyl fluorene polymer is dissolved in the anhydrous aprotic organic solvent to provide a polymer solution, followed by drying the polymer solution to remove water that may be present to provide a dried polymer solution having a water content of less than 500 ppm.

In some further embodiments of the method, the drying is repeated until a dried polymer solution having a water content of less than 200 ppm is attained.

In some additional particular embodiments, the drying step comprises azeotropically distilling the polymer solution.

In some further embodiments related to the foregoing, the drying is repeated until the water content of the polymer solution remains constant.

In one or more additional embodiments, the method further comprises, prior to the recovering step, adding an acid to the reaction mixture from step (i) in an amount effective to neutralize the base.

In some embodiments, the method is effective to produce a recovered water-soluble 9-methyl N-hydroxysuccinimidyl carbonate fluorene polymer comprising 15 mole percent or less of a water-soluble fulvene polymer.

In one or more embodiments of the method, the precipitating solvent is at a temperature above its freezing point and below room temperature.

In yet some further embodiments, the precipitating solvent comprises a small amount of acid.

In some embodiments, the method further comprises washing the recovered water-soluble 9-methyl N-hydroxysuccinimidyl carbonate fluorene polymer with an acidified precipitating solvent.

In one or more embodiments, the method further comprises purifying the recovered water-soluble 9-methyl N-hydroxysuccinimidyl carbonate fluorene polymer.

In yet some additional embodiments, the purifying step comprises dissolving the recovered water-soluble 9-methyl N-hydroxysuccinimidyl carbonate fluorene polymer in a solvent to provide a solution, passing the solution through a thiol-containing resin to remove any water-soluble fulvene polymer to thereby provide a purified solution, and removing solvent from the purified solution to recover purified water soluble 9-methyl N-hydroxysuccinimidyl carbonate fluorene polymer.

In yet one or more further embodiments, a recovered or purified water-soluble 9-methyl benzotriazolyl carbonate fluorene polymer or other reactive carbonate prepared by a method as described herein, is reacted with an amine-containing biologically active agent to provide a conjugate.

In another aspect, provided is a brominated water-soluble fluorene polymer. In one or more embodiments, the brominated water-soluble fluorene polymer has a structure selected from:

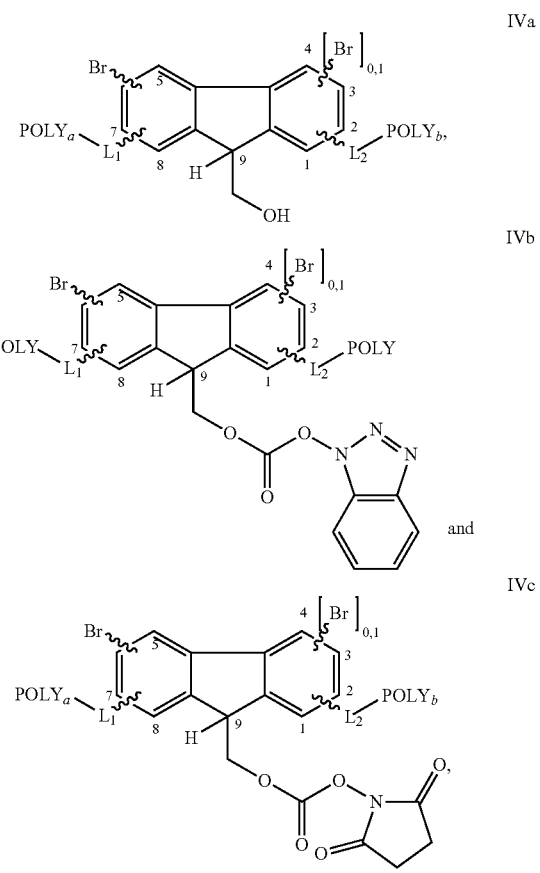

wherein $POLY_a$, $POLY_b$, $L_1$, and $L_2$ have values as described elsewhere herein.

Additional aspects and embodiments are set forth in the following description and claims.

BRIEF DESCRIPTION OF THE DRAWINGS

This section intentionally left blank as a placeholder.

DETAILED DESCRIPTION

Definitions

In describing and claiming certain features of this disclosure, the following terminology will be used in accordance with the definitions described below unless indicated otherwise.

As used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

"Water soluble, non-peptidic polymer" refers to a polymer that is at least 35% (by weight) soluble in water at room temperature. Preferred water soluble, non-peptidic polymers are however preferably greater than 70% (by weight), and more preferably greater than 95% (by weight) soluble in water. Typically, an unfiltered aqueous preparation of a "water-soluble" polymer transmits at least 75% of the amount of light transmitted by the same solution after filtering. Preferably, such unfiltered aqueous preparation transmits at least 95% of the amount of light transmitted by the same solution after filtering. Most preferred are water-soluble polymers that are at least 95% (by weight) soluble in water or completely soluble in water. With respect to being "non-peptidic," a polymer is non-peptidic when it contains less than 35% (by weight) of amino acid residues.

The terms "monomer," "monomeric subunit" and "monomeric unit" are used interchangeably herein and refer to one of the basic structural units of a polymer. In the case of a homo-polymer, a single repeating structural unit forms the polymer. In the case of a co-polymer, two or more structural units are repeated—either in a pattern or randomly—to form the polymer. Preferred polymers used in connection with the present invention are homo-polymers. The water-soluble, non-peptidic polymer comprises three or more monomers serially attached to form a chain of monomers.

"PEG" or "polyethylene glycol," as used herein, is meant to encompass any water-soluble poly(ethylene oxide). Unless otherwise indicated, a "PEG polymer" or a polyethylene glycol is one in which substantially all (preferably all) monomeric subunits are ethylene oxide subunits, though, the polymer may contain distinct end capping moieties or functional groups, e.g., for conjugation. PEG polymers will generally comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG polymers, the variable (n) ranges from about 3 to 2273, and the terminal groups and architecture of the overall PEG can vary. Additional sub-ranges for "n" are described herein. PEG polymers in connection with the present disclosure are typically end-capped, where a preferred end-capping group is a lower alkyl group, with a most preferred end-capping group being methyl.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques (e.g. gel filtration chromatography). Most commonly employed are gel permeation chromatography and gel filtration chromatography. Other methods for determining molecular weight include end-group analysis or the measurement of colligative properties (e.g., freezing-point depression, boiling-point elevation, or osmotic pressure) to determine number average molecular weight or the use of light scattering techniques, ultracentrifugation, MALDI TOF, or viscometry to determine weight average molecular weight. PEG polymers are typically polydisperse (i.e., the number average molecular weight and the weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

"Branched," in reference to the geometry or overall structure of a polymer, refers to a polymer having two or more polymer "arms" or "chains" extending from a branch point or central structural feature. Examples of some preferred branched polymers are those having one or more of the following features: having two or more polymer arms, having two polymer arms, comprised of polymer chains having the same structure (for example, comprised of the same monomer subunits), and comprised of polymer arms having the same weight average molecular weight.

A "stable" linkage or bond refers to a chemical bond that is substantially stable in water, that is to say, does not undergo hydrolysis or degradation under physiological conditions to any appreciable extent over an extended period of time. Examples of hydrolytically stable linkages generally include but are not limited to the following: carbon-carbon bonds (e.g., in aliphatic chains), ether linkages, amide linkages, amine linkages, and the like. It is to be understood however, that the stability of any given chemical bond may be affected by the particular structural features of the molecule in which the bond is positioned as well as the placement of the subject linkage within a given molecule, adjacent and neighboring atoms, and the like, as will be understood by one of skill in the chemical arts. One of ordinary skill in the art can determine whether a given linkage is stable or releasable in a given context by, for example, placing a linkage-containing molecule of interest under conditions of interest (e.g., under physiological conditions) and testing for evidence of release over a suitable time period. Generally, a stable linkage is one that exhibits a rate of hydrolysis of less than about 1-2% per day under physiological conditions. Hydrolysis rates of representative chemical bonds can be found in most standard organic chemistry textbooks.

A covalent "releasable" linkage, for example, in the context of a water-soluble polymer such as a polymeric FMOC reagent that is covalently attached to a target molecule, such as for example, an active moiety or other molecule, is one that, under physiological conditions, releases or detaches one or more water-soluble polymers from the active moiety. The release may occur, for example, by any suitable mechanism, and at a rate that is clinically useful. A releasable linkage may also be referred to as a physiologically cleavable bond or linkage.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 3-methylpentyl, and the like.

"Lower alkyl" refers to an alkyl group containing from 1 to 6 carbon atoms, and may be straight chain or branched, as exemplified by methyl, ethyl, n-butyl, i-butyl, and t-butyl.

"Alkoxy" refers to an —OR group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para). Substituents on aryl moieties that are a part of a more complex system, such as a naphthalene or fluorene core, may occupy any aryl ring position not otherwise occupied in the structure.

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl. An aromatic moiety (e.g., $Ar^1$, $Ar^2$, and so forth), means a structure containing aryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is a heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl, and substituted aryl.

An "anhydrous" substance is one that contains 500 parts per million (ppm) water or less. Preferably, an anhydrous substance or condition is one that contains 450 ppm water or less, or 400 ppm water or less. More preferably, an anhydrous substance of condition contains 200 ppm water or less. Most preferably, an anhydrous substance contains less water than is measurable by modern analytical methods, which currently is less than 100 ppm. An illustrative range of water content for an anhydrous substance or condition described herein is from about 80 ppm to about 200 ppm.

"Anhydrous conditions", for example, in reference to reaction conditions, refers to conditions in which care has been taken to exclude moisture from reactants, solvents, glassware, the atmosphere, and the like. Anhydrous conditions typically include the use of dried solvents (using any suitable drying technique well-known to those of skill in the chemical arts), dried reagents, an inert atmosphere, dried reaction equipment, and the like. Typical methods for drying solvents and measuring the residual water in such solvents may be found in works such as by Pangborn, A. B., et al *Organometallics*, 1996, 15, 1518-1520; and Williams, D. B. G., et al *J. Org. Chem.* 2010, 75, 8351-8354.

"Substantially" or "essentially" means nearly totally or completely, for instance, 95% or greater of a given quantity.

Similarly, "about" or "approximately" as used herein means within plus or minus 5% of a given quantity.

"Optional" or "optionally" means that the subsequently described circumstance may but need not necessarily occur, so that the description includes instances where the circumstance occurs and instances where it does not.

"Pharmaceutically acceptable excipient" or "pharmaceutically acceptable carrier" refers to a component that may be included in the compositions described herein and causes no significant adverse toxicological effects to a subject.

The term "patient," or "subject" as used herein refers to a living organism suffering from or prone to a condition that can be prevented or treated by administration of a compound or composition or combination as provided herein, such as a cancer, and includes both humans and animals. Subjects include, but are not limited to, mammals (e.g., murines, simians, equines, bovines, porcines, canines, felines, and the like), and preferably are human.

Overview

The polymeric FMOC reagents and some of the intermediates leading to the final polymeric reagent are susceptible to base-catalyzed loss of the carbonate functionality. The basic portion of the substance catalyzing the reagent's decomposition may be negatively charged or uncharged. This process is the same type of process that provides the PEG2-FMOC-therapeutic agent conjugates their efficacy. (Note that references to PEG-containing reagents or conjugates is also meant herein to apply equally to other water-soluble polymers such as those described herein). More particularly, a PEG2-FMOC conjugate releases a covalently attached therapeutic agent ("drug") by reaction in vivo with any substance capable of abstracting the ionizable benzylic proton at the 9-position of the fluorene ring. The drug release process is illustrated in Scheme II in relation to a particular illustrative PEG2-FMOC conjugate structure.

Scheme II.

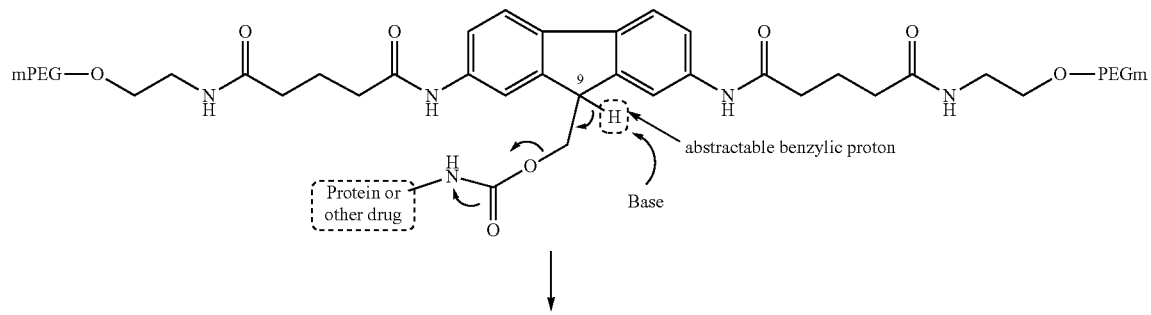

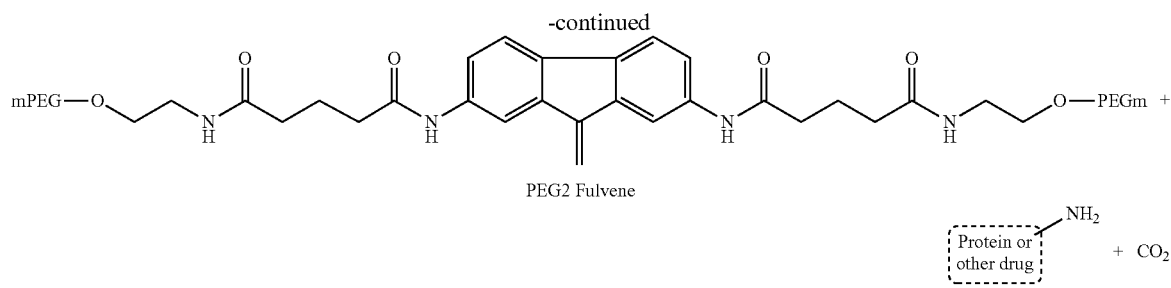

PEG2 Fulvene

Protein or other drug—NH₂ + CO₂

Following a similar mechanistic pathway to the pathway illustrated in Scheme II, the PEG2-FMOC-NHS reagent (or any other suitably activated PEG2-FMOC reagent) may react with a basic substance that is charged or uncharged. This is shown in Scheme III, illustrating the mechanism of the undesirable base-catalyzed elimination reaction of a PEG2-FMOC intermediate or reagent to provide a PEG2 fulvene derivative.

withdrawing due to the presence of certain atoms near or directly attached to the fluorene core. For example, the presence of electron withdrawing groups attached to the fluorenyl core can make the elimination reaction (e.g., Schemes II and III) much more facile, since electron withdrawing influences can affect the proton at the 9 position, making it more acidic and thus more susceptible to removal by a basic species. Thus, base catalyzed decomposition can

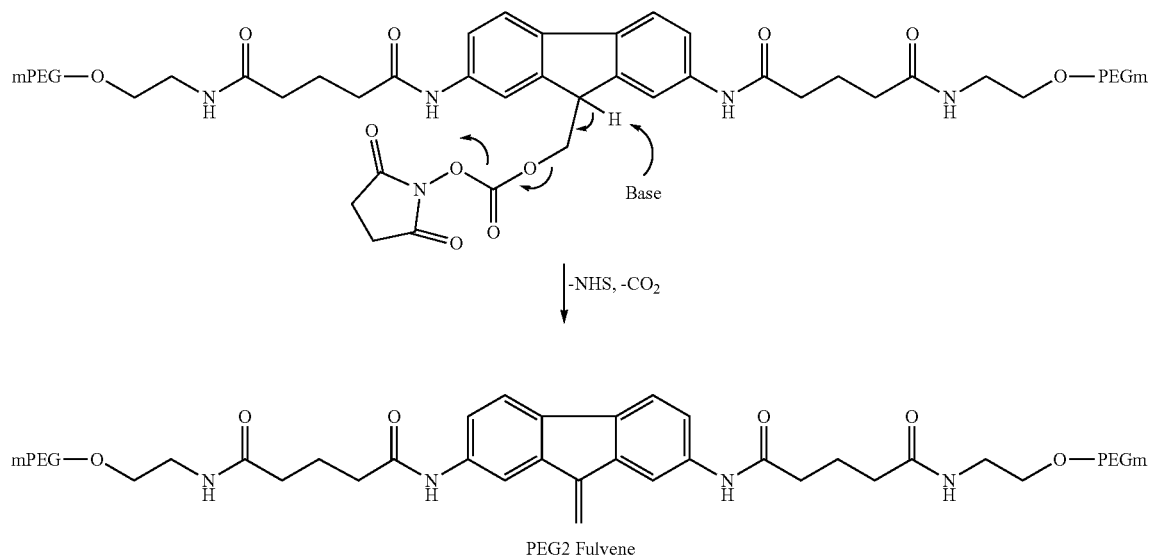

Scheme III.

PEG2 Fulvene

The PEG2-FMOC-BTC intermediates are degraded following a similar base-catalyzed process as shown for the NHS reagent in Scheme III, where the leaving group is 1-hydroxybenzotriazolyl rather than N-hydroxysuccinimide.

Thus, in order to provide an advantageous polymeric reagent, synthetic processes to provide these and other similar ester-like reagents should ideally be carried out under conditions effective to minimize losses due to the interaction of basic substances with the intermediates and final reagents. Such methodologies are particularly preferred when the fluorene ring is substituted with one or more electron withdrawing groups, such as $R^{e1}$ and $R^{e2}$ in Structure X. The reaction methods, conditions, intermediates, product recovery and purification procedures described herein illustrate that handling and care, for example, to exclude basic substances during processing or workup steps can also be important, for example, when the linker(s), i.e. $L_1$ or $L_2$, connecting the polymer become more electron be particularly problematic, and while typically not severe with the PEG2-G2-FMOC reagent class, it can be very severe with the PEG2-C2-FMOC reagents and reactive intermediates. As a result, the processes previously described for manufacture of the less reactive PEG-FMOC reagents have been discovered to be less preferred for providing good quality, highly reactive PEG-FMOC reagents (such as, e.g., the NHS reagents), and may not be successfully applied to the preparation of PEG-FMOC reagents of all reactivity types.

One consequence of the presence of the PEG2 fulvene in the reagent is the potential for an undesirable side reaction between targeted therapeutic agents and the PEG2 fulvene impurity. This side reaction is shown in illustrative Scheme IV below (where the exemplary water-soluble FMOC reagent shown is meant to be illustrative, and not limiting with respect to the structure of the FMOC polymeric fulvene).

Scheme IV.

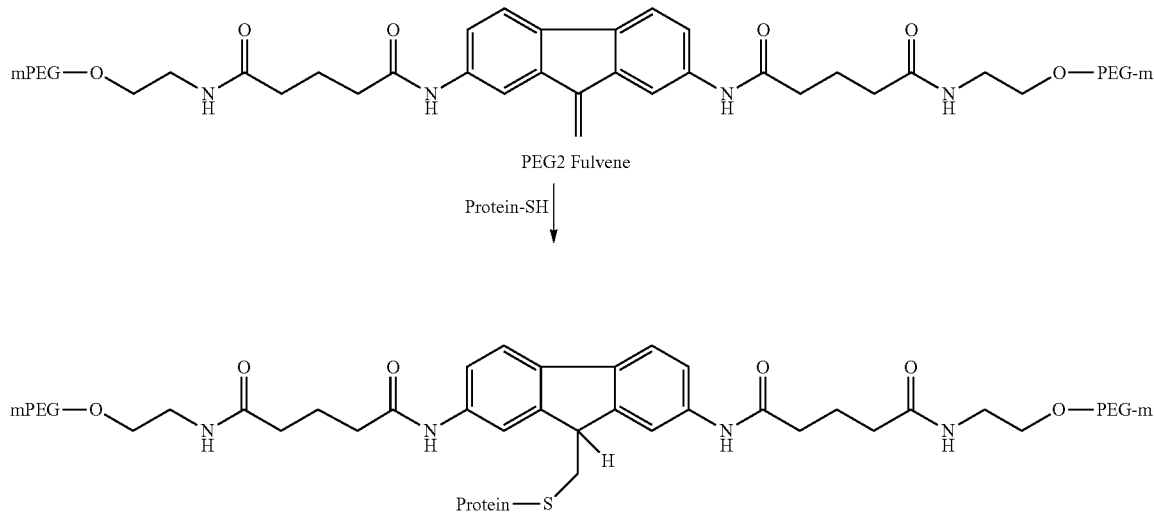

PEG2 Fulvene

In this reaction, a thiol group of a therapeutic agent, for example, a protein, may react with the PEG2 fulvene (see for example, Culbertson, S., et al., U.S. Pat. No. 8,905,235). Upon formation of a polymer conjugate as shown in Scheme IV, rather than of the intended conjugate formed by reaction between the PEG2 FMOC active carbonate reagent and, for example, a protein (see, e.g., Scheme I), release of the protein may occur by a totally different mechanism, and under very different environmental conditions. Thus, in one or more aspects, one object of the methods provided herein is to minimize and/or prevent the process shown in Scheme IV. A similar reaction may occur with any reactive nucleophile, such as, for example, an amine, but such reactions are not typically anticipated under the conjugation conditions.

It should be noted that the PEG2-fulvene is not removed during customary purification of a PEG-FMOC-NHS reagent, since a typical purification process is a re-precipitation procedure that removes most small molecules, but does not remove other PEG polymeric impurities. This represents a challenge that has not previously been addressed, but is addressed, among other challenges, by the instant disclosure.

Among the numerous process improvements and improved materials described herein, the present disclosure provides but is not limited to the following:

(i) improvements to methods for manufacturing reactive water-soluble polymeric FMOC reagents, such as, for example, C2-PEG2-FMOC-NHS;

(ii) methods in which the extremely toxic reagent, phosgene (or its precursors (e.g. triphosgene)), is replaced with safer reagents effective to form intermediates that can readily be converted into a reactive polymeric FMOC N-hydroxysuccinimide (NHS) reagent (i.e., methods that are absent phosgene or a phosgene precursor);

(iii) methods for the direct activation of 9-hydroxylmethyl fluorene polymers such as C2-PEG2-FMOC-OH with disuccinimidyl carbonate (DSC);

(iv) methods for removing the reactive PEG fulvene impurity prior to activation of polymeric hydroxymethylfluorene;

(v) methods for stabilization of the polymer FMOC active carbonate reagents by acidic additives; and (vi) methods where a typical polymer-FMOC intermediate, e.g. the chloroformate (ClC(O)O~) or a BTC derivative, is used as a reagent in the formation of a polymer-FMOC-therapeutic agent conjugate to thereby minimize the production of polymer-substituted fulvene, and to improve the yield of the polymer-FMOC therapeutic agent conjugate.

These and other aspects and embodiments are described in greater detail in the sections which follow.

Methods

As described above, process improvements are provided herein that allow for the manufacture of particularly reactive PEG-FMOC reagents. These discoveries were arrived at, at least in part, by first identifying the root causes of the reactive paths that can lead to the destruction of such reagents. While hydrolysis of a polymer reagent is generally a pathway for destruction of active ester or active carbonate reagents, this pathway has already been addressed (i.e., minimized) in previous descriptions of methods for making and recovering PEG-FMOC reagents (see, e.g., Bentley, M., et al, U.S. Pat. No. 8,252,275). In the methods described herein, attention is directed to the elimination process that leads to formation of the water soluble polymeric fulvene side product that can form as a primary impurity in the water-soluble polymer-FMOC active carbonate product. The fulvene is formed from the reagent as shown in illustrative Scheme III above. As the polymeric fulvene side product is an undesirable impurity in the reagent—because it is a reactive rather than an inert impurity—one of the aims of the methods provided herein is to remove or minimize formation of the fulvene. To that end, several process reactive substances that can lead to formation of the fulvene impurity have been identified, and modified reaction processes have in turn been developed (i) that eliminate or remove those substances, or (ii) in which substances have been added that are effective to neutralize undesirable reactive substances, so that they may not catalyze or otherwise cause the polymeric fulvene to form. A generalized reaction scheme is shown below as Scheme Va.

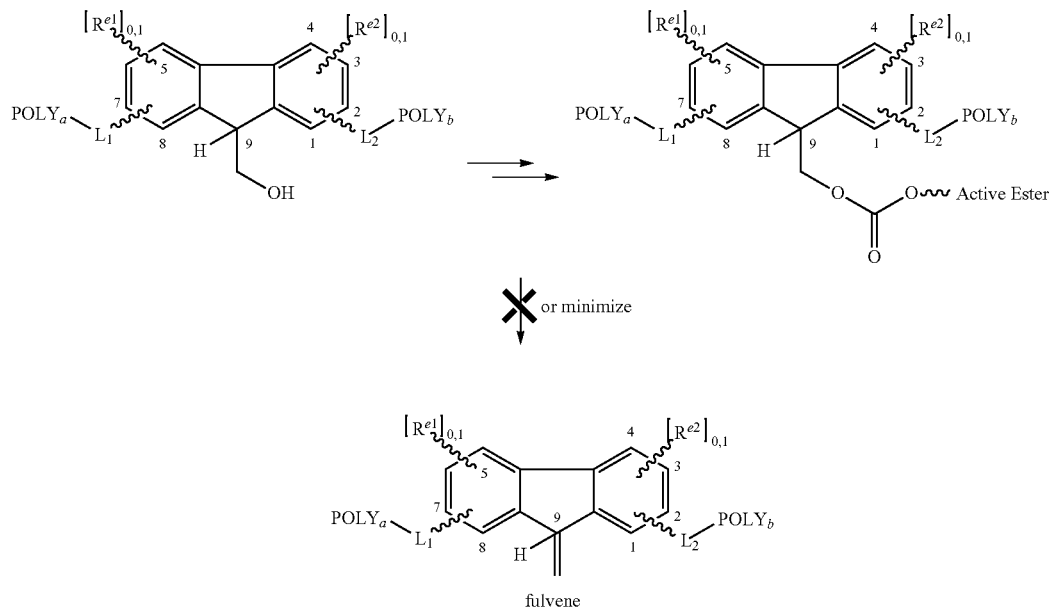

wherein, in each of the structures provided above, POLY$_a$ is a first water-soluble, non-peptidic polymer; POLY$_b$ is a second, water-soluble non-peptidic polymer; R$^{e1}$, when present, is a first electron-altering group; R$^{e2}$, when present, is a second electron-altering group; L$_1$ is a first linking moiety; and L$_2$ is a second linking moiety, where the features of each of POLY$_a$, POLY$_b$, R$^{e1}$, R$^{e2}$, L$_1$, and L$_2$ are provided in greater detail below.

Specifically, the undesirable substances that most often lead to formation of the fulvene species from the polymeric reagent, or from reactive intermediates leading to it, are basic substances that are ordinarily present in the reaction process. Such substances can be any chemical species that bears an atom that has a tendency to act as a base. For example, water may act as an acid or a base, and the tendency to act as one or the other is generally dependent on the pH of the medium. In the method of making a desired active carbonate polymer FMOC reagent, the most commonly definable substance that may act as a base is pyridine or a similar type basic substance. This chemical species acts to promote formation of the final active carbonate reagent. So its inclusion, or the inclusion of similar species, is typically utilized to provide favorable product yields. To prevent or minimize the reaction shown in Scheme IV, one of the approaches described herein is to either remove (or substantially remove) pyridine (or a similar species) during product isolation, or, neutralize this or a similar base to minimize its reactivity as a base. Thus, in one or more aspects or embodiments, an improved method for preparing a water-soluble polymeric FMOC reagent, such as an active carbonate ester, encompasses one or more steps for removing the basic species added to the process.

Also, in one or more additional aspects or embodiments of preparing a water-soluble polymeric FMOC reagent such as an active carbonate ester, or a precursor thereof, an acidic species is added to the reaction mixture following the reacting step, to thereby neutralize the pyridine or any other basic species that were added during the reaction process to facilitate product formation. In one or more embodiments, the acid is selected from, but is not limited to, acetic acid, triflouroacetic acid, citric acid, sodium dibasic phosphoric acid, potassium hydrogen phosphate, sulfuric acid, m-nitrobenzoic acid, trichloroacetic acid, phosphoric acid or any other inorganic or organic acidic species that does not cause undesirable effects in the reactive carbonate product. In one or more particular embodiments, the acid that is added to the reaction mixture is selected from acetic acid, citric acid, and phosphoric acid.

For example, in a method for preparing a reactive polymeric FMOC active carbonate reagent, a water-soluble 9-hydroxylmethyl fluorene polymer (e.g., of any one of structures (I), (I-a), (I-b), (I-c), (I-d), (I-e), (I-f), (I-g), (I-h)) is reacted with a reagent useful for forming an active carbonate of the water-soluble fluorene polymer in the presence of a base, followed by recovery of the water-soluble polymer 9-methyl fluorene active carbonate by precipitation. Suitable reactants for forming an active carbonate, or an active-carbonate precursor include, e.g., dibenzotriazolyl carbonate, N-hydroxy succinimide, chloroformates such as 4-nitrobenzyl chloroformate or 4-nitrophenyl chloroformate, and 1-hydroxybenzotriazole.

Representative water-soluble 9-hydroxylmethyl fluorene polymer starting materials are shown below:

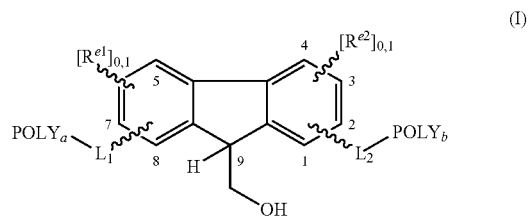

(I)

where POLY$_a$ is a first water-soluble, non-peptidic polymer; POLY$_b$ is a second, water-soluble non-peptidic polymer; R$^{e1}$, when present, is a first electron-altering group; and R$^{e2}$, when present, is a second electron-altering group; L$_1$ is a first linking moiety; and L$_2$ is a second linking moiety;

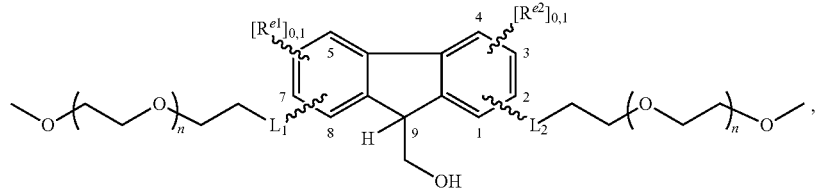

(I-a)

where $R^{e1}$ and $R^{e2}$, $L_1$ and $L_2$ are as described above (and in greater detail herein), and each $POLY_a$ and $POLY_b$ are, in this case, mPEG where n independently is in a range from about 3 to about 2273;

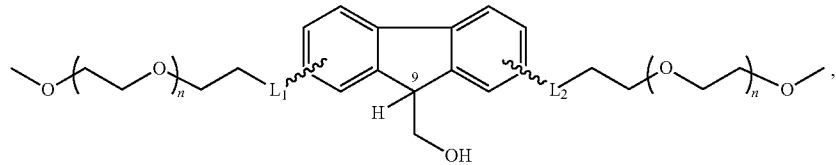

(I-b)

where $L_1$ and $L_2$ are as described above (and in greater detail herein), and each $POLY_a$ and $POLY_b$ are, in this case, mPEG where n independently is in a range from about 3 to about 2273;

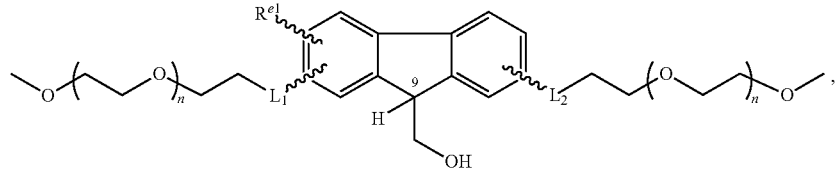

(I-c)

where $R^{e1}$, $L_1$ and $L_2$ are as described above (and in greater detail herein), and each $POLY_a$ and $POLY_b$ are, in this case, mPEG where n independently is in a range from about 3 to about 2273;

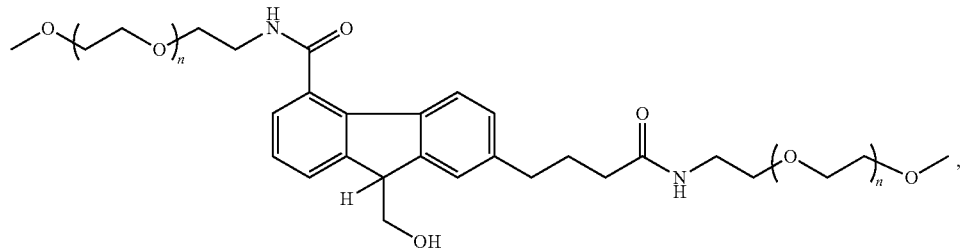

(I-d)

where each $POLY_a$ and $POLY_b$ are, in this case, mPEG where n independently is in a range from about 3 to about 2273;

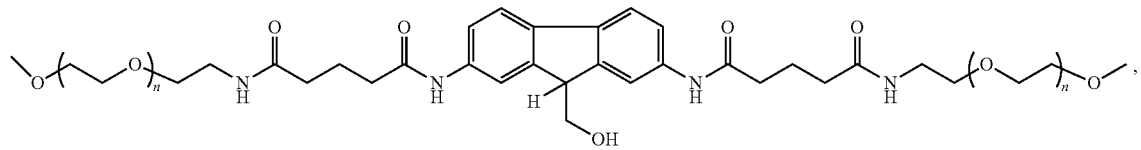

(I-e)

POLY$_a$ and POLY$_b$ are, in this case, mPEG where each n independently is in a range from about 3 to about 2273;

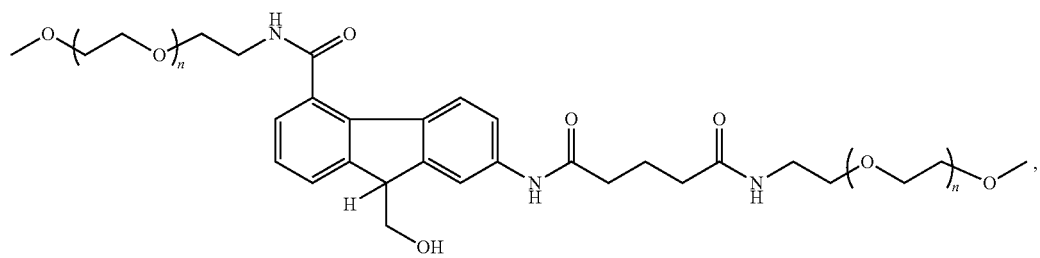

(I-f)

where POLY$_a$ and POLY$_b$ are, in this case, mPEG and each n independently is in a range from about 3 to about 2273;

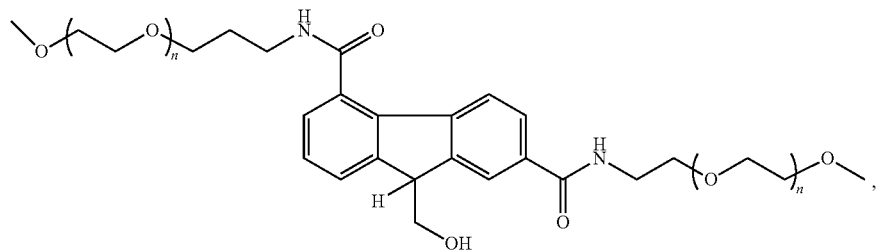

(I-g)

where POLY$_a$ and POLY$_b$ are, in this case, mPEG and each n independently is in a range from about 3 to about 2273, and

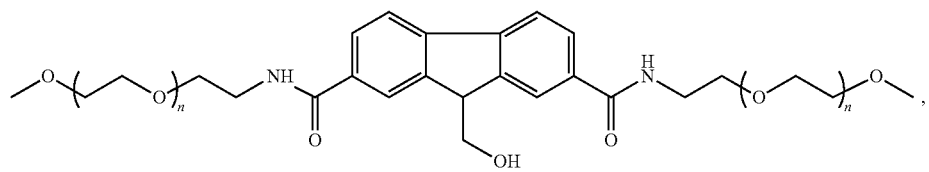

(I-h)

where POLY$_a$ and POLY$_b$ are, in this case, mPEG and each n independently is in a range from about 3 to about 2273.

Generally, the reaction is carried out under anhydrous conditions and in an anhydrous aprotic solvent. Exemplary aprotic solvents include, for example, halogenated aprotic solvents such as, for example, dichloromethane or trichloroethylene, or non-polar solvents such as benzene, chlorobenzene, nitrobenzene, xylene, cyclohexane, tetralin and toluene. In some embodiments, a mixture of two solvents may prove superior to either alone, and thus may be preferred. In some embodiments, the solvent is an aprotic polar solvent that is effective to dissolve the polymeric starting material. Other aprotic solvents that may be used include, e.g., dimethylformamide, acetone, acetonitrile, dioxane, tetrahydrofuran (THF), dimethylsulfoxide, HMPA (hexamethylphosphoramide), DMA (dimethylacetamide), and NMP (N-methylpyrrolidinone). Again, in some embodiments, a mixture of two or more solvents may be preferred. Aprotic solvents lack an acidic hydrogen, i.e., they are not proton donors. Some aprotic solvents, however, tend to be mildly basic and may hence not be good choices. One skilled in the art of chemistry would be able to readily determine additional aprotic solvents suitable for use in the reactions described herein. Generally, the choice of a proper solvent depends on the solvent's ability to dissolve all components of a reaction without reacting with any reaction component or reaction product. Alternatively, the ability of a solvent to be employed under anhydrous conditions is important, since in the reactions described herein, moisture should be minimized to protect moisture-sensitive reactants and products. Furthermore, a solvent may be used to co-distill with moisture that may be present. Some solvents may be better at removing moisture than others, as may be determined through routine experimentation using the guidance provided herein. In one or more embodiments, during the recovery step, the precipitating solvent comprises an acid (such as described above) in an amount effective to partially or completely neutralize excess base present in the reaction mixture.

As some processes that are suitable for a laboratory in which reactions are carried out by skilled and highly educated chemists are moved into production facilities (in which reactions may be carried out by skilled but less highly educated operators), safety of the technicians becomes a major concern. Thus, to address this concern, in yet one or more further aspects or embodiments, synthetic methods are provided herein in which certain undesirable or dangerous to handle reagents, such as phosgene or its precursors (e.g., triphosgene), are replaced with safer to handle reagents that ultimately lead to the reactive N-hydroxysuccinimide (NHS) reagent. That is to say, in one or more aspects or embodiments, provided herein is a method of preparing a water-soluble polymeric FMOC reagent such as an active carbonate or an intermediate effective to form an active ester such as an active carbonate ester, that is carried out absent the use of phosgene or one of its precursors as shown generally in Scheme Va or Vb above. Additionally, in some embodiments, diBTC, which under certain circumstances is explosive, is eliminated as a direct route to the NHS carbonate is employed. Thus, in some further embodiments, neither a phosgene derivative nor diBTC is used to preparee the desired active carbonate.

One such method for making a water-soluble polymer FMOC active carbonate comprises as a reactant, dibenzotriazolyl carbonate (diBTC). DiBTC is an explosion hazard when handled as a dry powder, but is considered safe to handle as a suspension in certain halogenated solvents. Such suspensions are commercially available; moreover, diBTC does not have, like phosgene, the potential to release toxic gases. As a result, in one or more further aspects or embodiments, provided herein is a method that employs a safer-to-use reagent, such as diBTC, to effect the conversion of an intermediate water-soluble polymeric hydroxymethyl fluorene derivative (see, e.g., structure (I), or any one of structures (I-a), (I-b), (I-c), (I-d), (I-e), (I-f), (I-g), (I-h)) to the corresponding polymeric fluorene BTC active carbonate (see, for example, Scheme Va and b). Exemplary BTC carbonates are provided below.

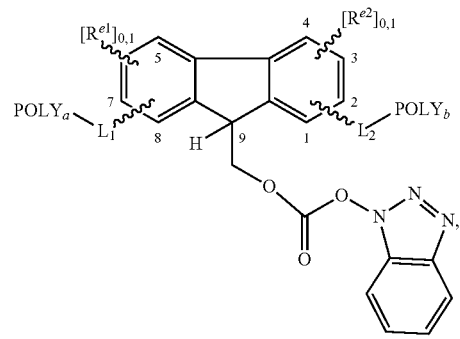

(II)

where $POLY_a$, $POLY_b$, $R^{e1}$, $R^{e2}$, $L_1$ and $L_2$ are as described above (and in greater detail herein);

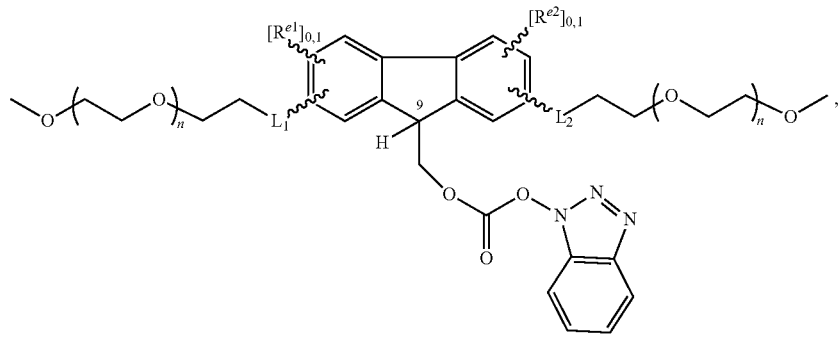

(II-a)

where $R^{e1}$, $R^{e2}$, $L_1$ and $L_2$ are as described above (and in greater detail herein), and $POLY_a$ and $POLY_b$ are, in this case, mPEG where each n independently is in a range from about 3 to about 2273;

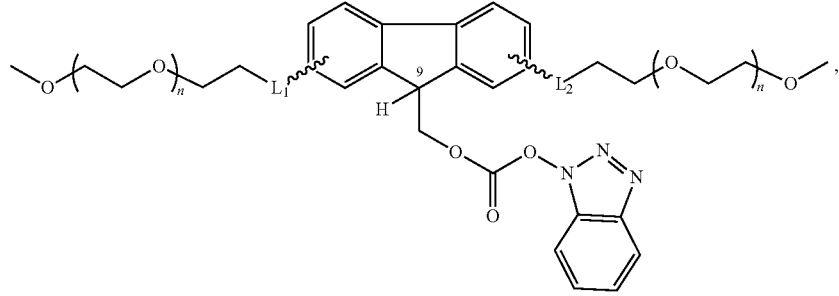

(II-b)

where $L_1$ and $L_2$ are as described above (and in greater detail herein), and $POLY_a$ and $POLY_b$ are, in this case, mPEG where each n independently is in a range from about 3 to about 2273;

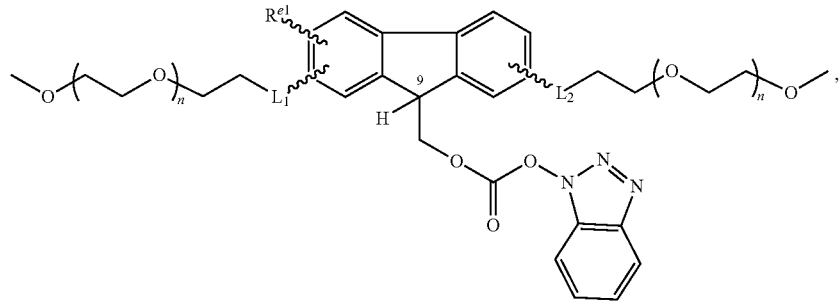

(II-c)

where $L_1$ and $L_2$ are as described above (and in greater detail herein), and $POLY_a$ and $POLY_b$ are, in this case, mPEG where each n independently is in a range from about 3 to about 2273;

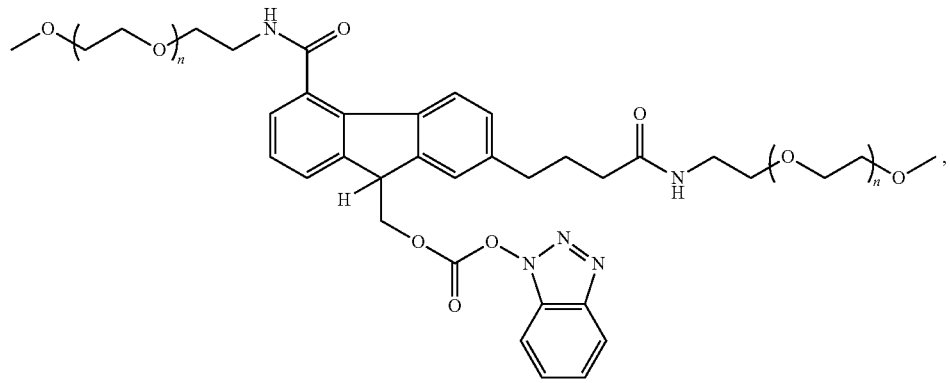

(II-d)

wherein $POLY_a$ and $POLY_b$ are, in this case, mPEG and each n independently is in a range from about 3 to about 2273;

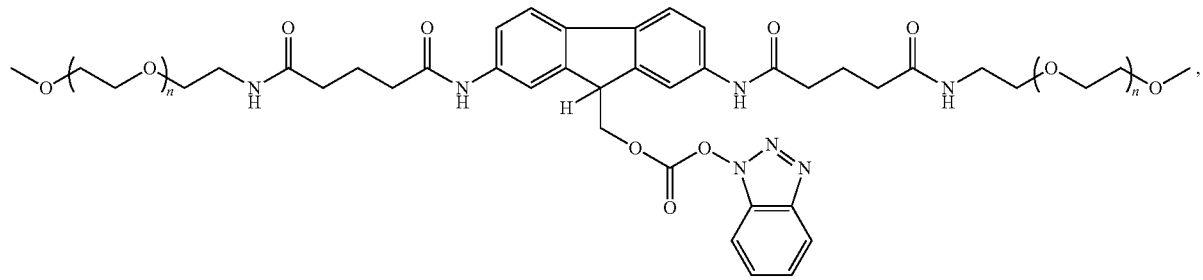

(II-e)

wherein $POLY_a$ and $POLY_b$ are, in this case, mPEG where each n independently is in a range from about 3 to about 2273;

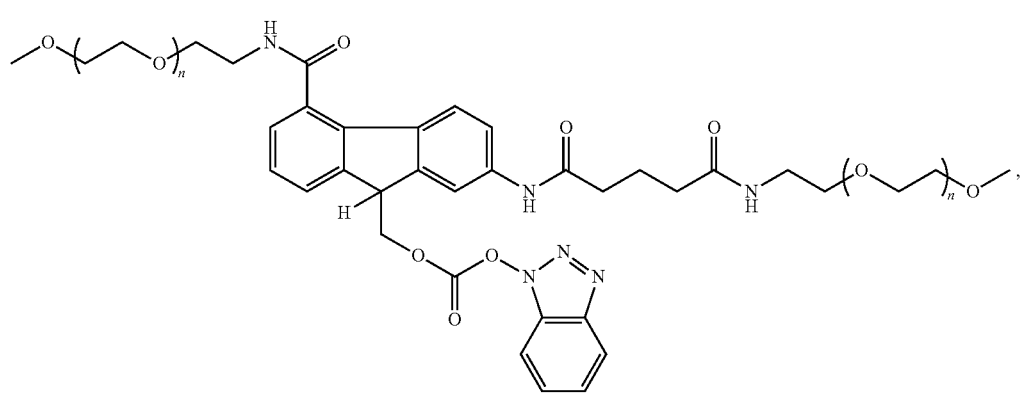

(II-f)

wherein POLY$_a$ and POLY$_b$ are, in this case, mPEG and each n independently is in a range from about 3 to about 2273;

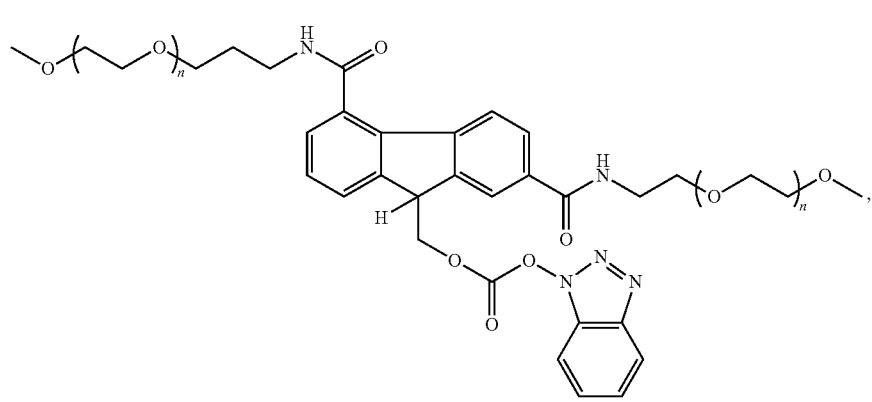

(II-g)

wherein POLY$_a$ and POLY$_b$ are, in this case, mPEG and each n independently is in a range from about 3 to about 2273; and

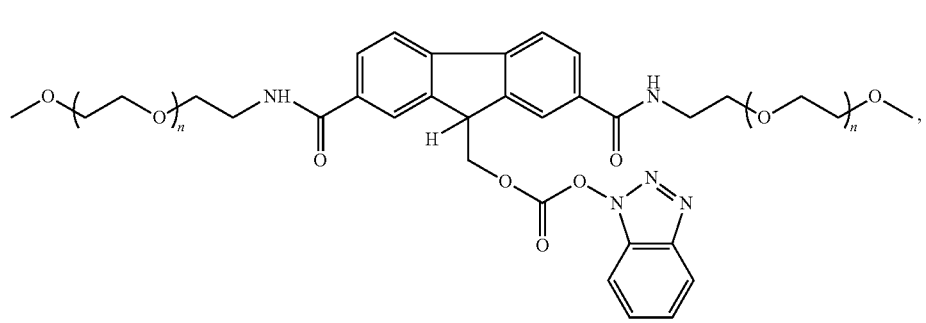

(II-h)

wherein POLY$_a$ and POLY$_b$ are, in this case, mPEG and each n independently is in a range from about 3 to about 2273.

In the method, a water-soluble 9-hydroxymethyl fluorene polymer having a structure such as structure (I) (or, for example, any one of structures (I-a), (I-b), (I-c), (I-d), (I-e), (I-f), (I-g), (I-h)) is reacted with dibenzotriazolyl carbonate in an anhydrous aprotic solvent in the presence of a base under anhydrous conditions to provide a reaction mixture comprising a water-soluble 9-methyl benzotriazolyl carbonate fluorene polymer of structure (II), or in one or more embodiments, for example, any one of structures (II-a), (II-b), (II-c), (II-d), (II-e), (II-g), (II-h), followed by recovering the water-soluble 9-methyl benzotriazolyl carbonate fluorene polymer by precipitation with an anhydrous solvent effective to promote precipitation of the water-soluble 9-methyl benzotriazolyl carbonate fluorene polymer.

As described above, exemplary anhydrous aprotic solvents for carrying out the reaction include, for example, anhydrous halogenated aprotic solvents such as, for example, dichloromethane or trichloroethylene, or non-polar solvents such as benzene, chlorobenzene, nitrobenzene, xylene, tetralin and toluene. Other anhydrous aprotic solvents that may be used include, e.g., dimethylformamide, acetone, acetonitrile, dioxane, tetrahydrofuran (THF), dimethylsulfoxide, HMPA (hexamethylphosphoramide), DMA (dimethylacetamide), and NMP (N-methylpyrrolidinone). Additional comments, found elsewhere in this application, related to choosing an acceptable solvent or mixture of solvents for a particular reaction, also apply here. One skilled in the art would be able to readily determine other suitable aprotic solvents for use in the reactions described herein. In some particular embodiments, the reaction solvent is an anhydrous chlorinated solvent such as dichloromethane or trichloroethylene. In yet some other embodiments, the reaction solvent is an anhydrous solvent selected from dimethylformamide, acetone, acetonitrile, and tetrahydrofuran. In some related embodiments, prior to the reaction, the water-soluble 9-hydroxymethyl fluorene polymer is dissolved in the aprotic organic solvent to form a solution, followed by azeotropic distillation of the solution to provide a solution and/or residue having a water content of less than 500 ppm. Additional approaches for preparing an anhydrous solvent, and/or anhydrous polymeric reactants, intermediates or reagents, and/or for providing anhydrous reaction conditions are described elsewhere herein.

The reaction comprises a sufficient amount of di-BTC to effect formation of the BTC carbonate ester. Generally, a sufficient amount of di-BTC is less than about 30 equivalents. For example, in some embodiments of the method, the water-soluble 9-hydroxymethyl fluorene polymer is reacted with less than about 30 equivalents of di-BTC. For example, the water-soluble 9-hydroxymethyl fluorene polymer may be reacted with from about 1 equivalent to about 30 equivalents of di-BTC (e.g., 1, 2, 3, 4, 5, 6, 7, 8, 9, 10, 11, 12, 13, 14, 1, 16, 17, 18, 19, 20, 21 22, 23, 24, 25, 26, 27, 28, 29, or 29.9 equivalents, inclusive of any and all ranges between any two of the preceding values). For example, the amount may be from about 1 to about 25 equivalents of di-BTC, or from about 1 to 20 equivalents of di-BTC, or from about 1 to 15 equivalents of di-BTC, or from about 1 to 10 equivalents of di-BTC. Additional suitable amounts of the di-BTC reagent relative to the water-soluble 9-hydroxymethyl fluorene polymer are from about 2 to about 20 equivalents, from about 5 to about 15 equivalents, or from about 10-20 equivalents.

Generally, the base used in the reaction is a non-nucleophilic amine or is a weakly nucleophilic amine. For example, illustrative bases that may be used include pyridine, 4-dimethylaminopyridine, N,N-diisopropylethylamine, 2,6-di-tert-butylpyridine, N-methylimidazole, N-methylmorpholine, 2,6-lutidine, 2,4,6-collidine, N,N,2,6-tetramethylpyridine-4-amine, and the like. Additionally, insoluble-polymer-bound forms of any of the foregoing bases may also be employed. For example, polymer bound 4-dimethylaminopyridine is available from Sigma-Aldrich (~3 mmol/g loading, matrix crosslinked with 2% divinylbenzene); also available from Sigma-Aldrich is polymer bound 2,6-di-tert-butylpyridine (~1.8 mmol/g loading, 1% crosslinked with divinyl benzene), along with a number of additional polymer-supported bases. The amine may also be a polyamine such as, for example, N,N,N',N'-tetramethyl-1, 6-hexamethyldiamine, N,N',N',N",N"-pentamethyldiethylenetriamine, and hexamethylenetetramine, or an insoluble polymer-bound form of any of the foregoing. In one or more embodiments of the method, the amount of base ranges from about 1 to about 30 equivalents, or from about 1 to about 10 equivalents. More particularly, the reaction may be carried out with about 1, 2, 3, 4, 5, 6, 7, 8, 9, 10, 11, 12, 13, 14, 1, 16, 17, 18, 19, 20, 21 22, 23, 24, 25, 26, 27, 28, 29, or 30 equivalents of base, wherein the foregoing is inclusive of any and all ranges between any two of the preceding values. The optimum amount of base for any particular process is best determined by experiment. The minimum amount of base required to provide the highest reaction yield is preferred.

The reaction may be carried out with or without mechanical agitation. Typically, but not necessarily, the reaction is carried out with mechanical agitation. Mechanical agitation is especially recommended for large scale reactions to facilitate good mixing. Generally, the water-soluble 9-hydroxymethyl fluorene polymer is reacted with dibenzotriazolyl carbonate at a temperature in a range of from about −20° C. to about 35° C. Additional exemplary temperature ranges include from about −10° C. to about 25° C., or from about −5° C. to about 10° C.

In turning now to the recovery of the water-soluble 9-methyl benzotriazolyl carbonate fluorene polymer, in some embodiments, the water-soluble 9-hydroxymethyl fluorene polymer and the corresponding water-soluble 9-methyl benzotriazolyl carbonate fluorene polymer product are both soluble in the aprotic organic solvent(s). Thus, in some embodiments, the resulting reaction mixture comprises solids, and recovery of the product comprises first removing the solids comprised in the reaction mixture, followed by recovery of the benzotriazolyl carbonate product. For example, solids comprised in the reaction mixture may be removed by any suitable method using best practices. For example, the solids may be removed by filtration. Following removal of the solids, an anhydrous precipitating solvent is then typically added to the remaining solution (or filtrate in the instance of having removed solids by filtration) in an amount effective to precipitate the benzotriazolyl carbonate product. Alternatively, following removal of the solids, the remaining benzotriazolyl carbonate product is added to the anhydrous precipitating solvent. That is to say, the anhydrous precipitating solvent may be added to the polymer product, benzotriazolyl carbonate, to effect precipitation, or the polymer product may be added to the anhydrous precipitating solvent. In some instances, the anhydrous precipitating solvent is miscible with the anhydrous aprotic organic solvent from the reacting step, and is also a solvent in which the 9-methyl benzotriazolyl carbonate fluorene product is insoluble or is substantially insoluble.

In one or more embodiments, the anhydrous solvent that is incorporated to promote precipitation of the BTC ester product may comprise an acid. In one or more embodiments, the acid is selected from, but is not limited to, acetic acid, triflouroacetic acid, citric acid, sodium dibasic phosphoric acid, potassium hydrogen phosphate, sulfuric acid, m-nitrobenzoic acid, chloroacetic acid, trichloroacetic acid, phosphoric acid or any other inorganic or organic acidic species that does not cause undesirable effects in the reactive carbonate product. In one or more particular embodiments, the acid that is added to the reaction mixture is selected from acetic acid, citric acid, and phosphoric acid. In some preferred embodiments, the acid is phosphoric acid. The acid is generally added in an amount that is sufficient to partially or completely neutralize the base that is contained in the reaction mixture. In some embodiments, the amount of acid that is added to the anhydrous solvent for promoting precipitation of the water-soluble 9-methyl benzotriazolyl carbonate fluorene polymer comprises a small amount of acid. For example, the anhydrous solvent may comprise from about 0.0001 to about 0.5 mole percent acid. For example, the anhydrous precipitating solvent may comprise from about 0.0002 to about 0.4 mole percent acid, or from about 0.0010 to about 0.4 mole percent acid, or from about 0.0050 to about 0.3 mole percent acid. The exact amount of acid used in a particular process is selected based on the anticipated amount of the base to be neutralized and is best determined by experiment.

Exemplary precipitating solvents can be determined by those of skill in the art and include aliphatic hydrocarbons and other non-reactive miscible solvents in which the BTC ester product is insoluble or substantially insoluble. Illustrative precipitating solvents include, for example, diethyl ether, isopropyl alcohol (IPA), methyl-t-butyl ether (MTBE), pentane, hexane and heptane, and mixtures of any two or more of the foregoing. One exemplary mixture is a mixture of isopropyl alcohol and methyl-t-butyl ether. One such preferred mixture is a 1:1 mixture of isopropyl alcohol and methyl-t-butyl ether, although any combination of the two solvents may be employed.

Following recovery of the precipitated BTC ester product, e.g., by filtration, the recovered product may be further washed with an anhydrous precipitating solvent, i.e., a solvent in which the BTC ester is insoluble or substantially insoluble, where the solvent may comprise a small amount of acid, e.g., from about 0.0001 to about 0.5 mole percent acid. Washes of a recovered FMOC-polymeric product, with, for example, an anhydrous precipitating solvent (also referred to as a "non-solvent"), may further comprise an antioxidant, such as butylated hydroxyl toluene (BHT), to avoid oxidative degradation. The recovered product may then be further dried if desired, and/or further purified using standard art-known methods for purifying water-soluble polymeric reagents. One such particularly preferred method is chromatography, e.g., size exclusion chromatography.

Example 1 provides an illustration of the reaction and related processing steps described above. See, Example 1B, describing the preparation of G2-PEG2-FMOC-BTC-20kD from the corresponding G2-PEG2-FMOC-OH-20kD. As described therein, following dissolution of the G2-hydroxymethyl fluorene polymer in anhydrous dichloromethane and anhydrous toluene, the solvents were then removed by distillation to remove moisture, followed by dissolution in anhydrous acetonitrile. Following reaction of the G2-hydroxymethyl fluorene polymer with di-BTC, the product was precipitated by addition of anhydrous isopropyl alcohol (containing butylated hydroxytoluene), recovered by filtration, and further washed with non-solvents (e.g., isopropyl alcohol and diethyl ether), and dried under vacuum.

Example 3, Part 2, IB describes the preparation of C2-PEG2-FMOC-BTC-20kD from the corresponding C2-PEG2-FMOC-OH-20kD. Briefly, C2-PEG2-FMOC-OH-20kD, was dissolved in anhydrous solvent, toluene, and then dried by azeotropically distilling off the solvent under reduced pressure. This process was then repeated. The dried C2-PEG2-FMOC-OH-20kD was then dissolved in anhydrous acetonitrile, the solution cooled (e.g., to 5° C.), followed by addition of di-BTC and the base, pyridine. The mixture was then stirred for several hours. Following reaction, the mixture was added to a solution of cooled isopropyl alcohol containing the acid, phosphoric acid (0.005%). The mixture was then further mixed, and chilled MTBE containing phosphoric acid (0.005%) was added to the mixture followed by additional stirring to facilitate precipitation. The precipitated product was then recovered by filtration, and washed multiple times with a mixture of IPA/MTBE containing phosphoric acid, where subsequent washes contained slightly less phosphoric acid (e.g., 0.005% and 0.002%). The product was then dried under vacuum at reduced temperature, 15° C.

While a BTC derivative itself may be used to react with proteins or other suitable active agents to form polymer-active agent conjugates, the corresponding biotherapeutic agent conjugates are typically formed rapidly when a more active carbonate, e.g., the N-hydroxy succinimidyl (NHS) carbonate (sometimes called an active ester) is employed. Therefore, in yet one or more additional aspects or embodiments, provided is a method in which a polymeric FMOC-BTC derivative such as that of structure (II), or, for example, of any one of structures (II-a) through (II-h), is used as an intermediate that may be converted into the desired NHS active carbonate ester (see, e.g., Scheme VI), e.g., having a generalized structure such as (X). Particular PEG2 FMOC-NHS esters are shown in structures (XI), (XII), (XIII), and (XIV). A preferred NHS ester is shown in structure (XIV). The particular reaction conditions for converting a polymeric FMOC-BTC ester into the corresponding reactive NHS ester shown in illustrative Scheme Vb below (e.g., acetonitrile solvent, pyridine base, N-hydroxysuccinimide (NETS) reagent; or e.g., dichloromethane solvent, dimethylaminopyridine, NETS) are meant to be illustrative; suitable solvents, bases, coupling or other additional reagents, and reaction conditions can be readily determined by those skilled in the art for transforming a water-soluble polymer FMOC BTC carbonate (or other less reactive carbonates) into a corresponding NHS carbonate. For example, the conversion reaction may be carried out using from about 1 to about 30 equivalents of NHS. Additional illustrative amounts of the NHS reagent include, for example, from about 1 to about 25 equivalents, from about 2 to about 20 equivalents, from about 3 to about 15 equivalents, and from about 5 equivalents to about 15 equivalents. Typically, during addition of the NHS reagent, the reaction temperature is maintained at from about −20° C. to about 25° C. Illustrative reaction temperature ranges are selected from, for example, from about −15° C. to about 20° C., from about −10° C. to about 10° C., from about −10° C. to about 0° C., from about −8° C. to about 5° C. , and from about −7° C. to about 0° C. In some embodiments, the temperature is in a range between about −10° C. to about 10° C. The optimum temperature for a specific reaction can be determined by experimentation. In some embodiments, conversion of the polymeric FMOC-BTC ester into the NHS ester by reaction with NHS is carried out in dichloromethane in the presence of dimethylaminopyridine. Suitable amounts of dimethylaminopyridine to facilitate the conversion range, for example, from about 4 equivalents to about 0.10 equivalents, from about 3 equivalents to about 0.15 equivalents, from about 2 equivalents to about 0.20 equivalents, from about 1 equivalent to about 0.40 equivalents, and from about 0.75 equivalents to about 0.50 equivalents. In some embodiments, DMAP is present in an amount from about 2 equivalents to about 0.20 equivalents. In some other embodiments, DMAP is present in an amount from about 1 equivalent to about 0.4 equivalents. In some other embodiments, DMAP is present in an amount from about 0.75 equivalents to about 0.50 equivalents. All of the processes where active carbonates are prepared, isolated, purified, or otherwise handled, are preferably carried out in a very dry environment, preferably in a glove box under a blanket of dry nitrogen or argon or in a laboratory with very low humidity. Furthermore, all solvents and reagents should preferably be of high quality and maintained in a dry environment prior to use. When drying techniques are used to remove moisture prior to a reaction, a moisture analysis is typically carried out to assure that the moisture levels are as low as can be attained using the specified procedure. In repeat experiments, the moisture analysis may be omitted if the moisture-removing process has been validated. Following preparation of a polymeric FMOC-NHS ester, the polymeric FMOC-NHS ester may be recovered and further processed as described below.

Scheme Vb.
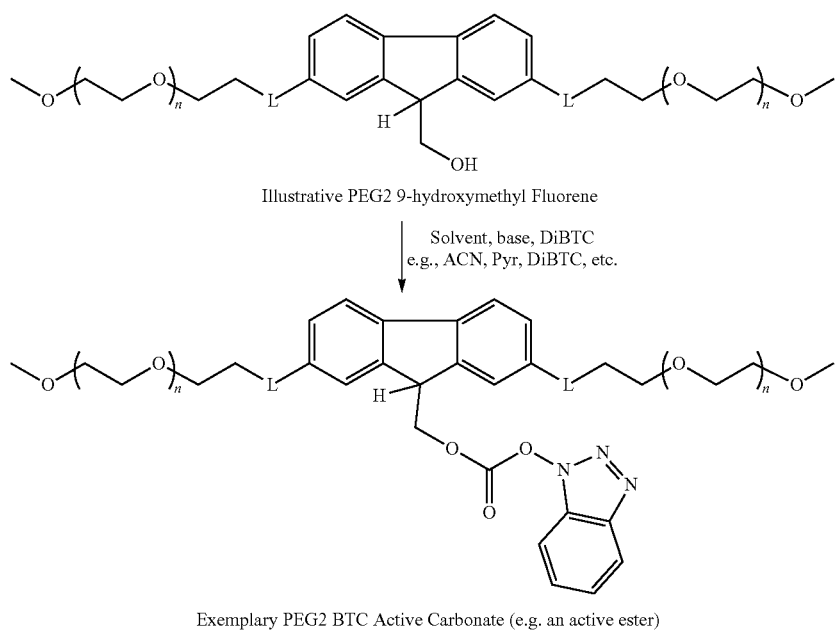
L = Linker
Scheme VI.
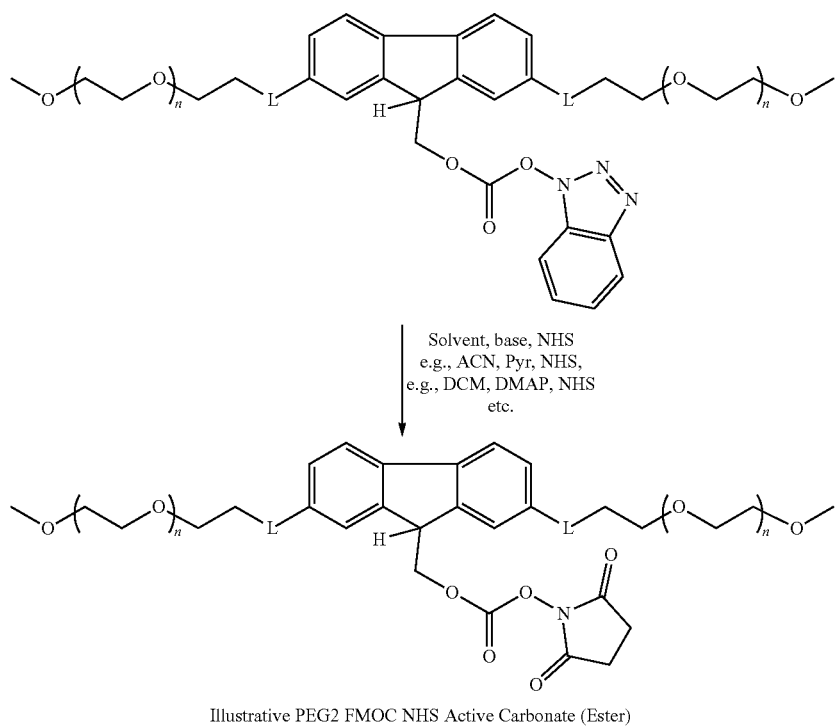
L = Linker
See, for example, Example 1C, in which an illustrative 9-methyl benzotriazolyl carbonate fluorene PEG polymer, G2-PEG2-FMOC-BTC-20kD, is converted to the corresponding succinimidyl ester according to the method provided herein. As described in the example, G2-PEG2-FMOC-BTC-20kD was dissolved in an anhydrous solvent, dichloromethane, and the solution then cooled (to 8° C.). N-hydroxysuccinimide was then added to the cooled solution, and the reaction mixture stirred overnight at 8° C. The resulting NHS ester product was then recovered by precipitation with isopropyl alcohol (containing citric acid and the antioxidant, BHT), isolated by filtration, and then further washed with non-solvents (first with anhydrous isopropyl alcohol (containing BHT), followed by anhydrous methyl-tert butyl ether containing citric acid and BHT), followed by vacuum drying. To determine percent substitution of the active carbonate, reaction with glycine was carried out, followed by analysis. Notably, the NHS ester prepared and processed as described above possessed 88.1 mole percent substitution; following storage at 11° C. for 136 hours, the product exhibited a percent substitution of 86.6 mole % (a loss of about 1-2%). In contrast, a similar NHS ester product prepared but precipitated absent the addition of acid to the solvent, isopropyl alcohol, and also having no acid present in the methyl tert-butyl ether wash was found to have a degree of substitution of 86.2 mole percent following preparation (slightly less than by the present method). However, following storage at 11° C. for 136 hours, the stored product was determined to have a percent substitution of 75.3 mole % (that is, a loss of product of about 11%). Thus, the process improvements described herein are effective to provide active fluorene polymer NHS ester reagents having greater stability upon storage, e.g., by using acidic additives during recovery and processing of both intermediates and active carbonate reagents.

This process is also further exemplified in Example 3, Part 2, IC, which describes the preparation of C2-PEG2-FMOC-NHS 20 kD from C2-PEG2-FMOC-BTC 20 kD.

Since the water-soluble polymer FMOC active NHS carbonate (ester) may be more highly desired as a reagent for conjugation with an active agent, such as, for example, a protein, to form a polymeric prodrug, in one or more further aspects or embodiments, also provided herein are methods for the direct activation of C2-PEG2-FMOC-OH (or any other water-soluble 9-hydroxymethyl fluorene polymer as described herein) with disuccinimidyl carbonate (DSC) to provide the corresponding NHS active carbonate. Illustrative polymeric starting materials include those described by structures (I), (I-a), (I-b), (I-c), (I-d), (I-e), (I-f), (I-g), and (I-h)), where the corresponding NHS active carbonates correspond to each of the foregoing structures wherein the 9-methyl hydroxyl proton is replaced with ~C(O)O— succinimide. Similarly illustrative products, i.e., the NHS carbonates, include those having structures (III), (X), (XI), (XII), (XIII), (XIV). See generalized Schemes VIa and VIb below, where Scheme VIa illustrates the subject reaction for a generalized water soluble 9-hydroxymethyl fluorene polymer, while Scheme VIb shows the same reaction for a preferred water soluble PEG-2 9-hydroxymethyl fluorene polymer having a C2 core.

Scheme VIa.

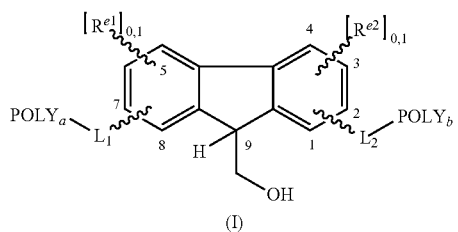

(I)

anh. solvent | DSC base

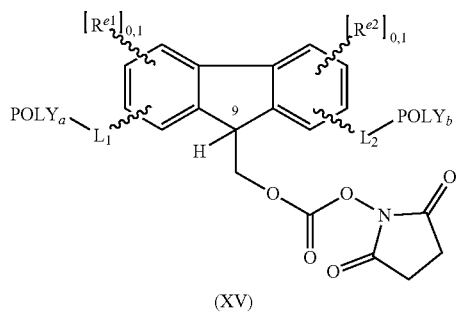

(XV)

Scheme VIb.

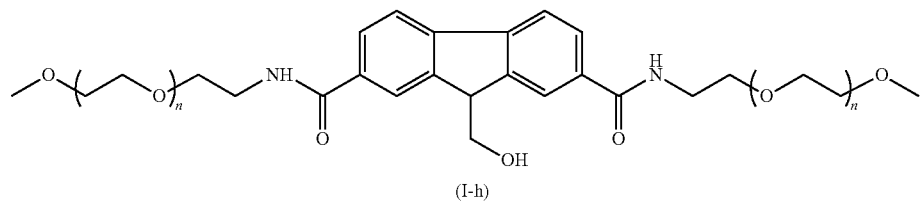

(I-h)

anh. solvent | DSC, base

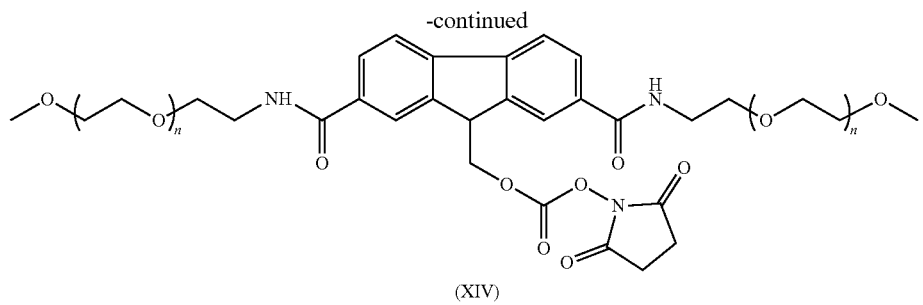

(XIV)

As this process can be productive under a variety of conditions, numerous conditions were explored to find optimum conditions. In one or more embodiments, a polymeric hydroxymethyl fluorene derivative, such as, for example C2-PEG2-FMOC-OH, (or having a structure such as structure (I), (I-a), (I-b), (I-c), (I-d), (I-e), (I-g), and (I-h)) is dissolved in a suitable anhydrous solvent. Exemplary solvents include aprotic organic solvents such as, for example, chloroform, dichloromethane, acetonitrile, dimethylformamide, dioxane, acetone, tetrahydrofuran, and the like, including mixtures of the foregoing. In some embodiments, the aprotic organic solvent is a polar aprotic solvent. Preferably, the polymeric hydroxymethyl fluorene derivative is soluble in the aprotic organic solvent. The resulting solution may then be further dried, for example, by using commonly employed methods to remove any traces of moisture that may hydrolyze the highly reactive carbonate reagent. Such methods are well known in the art and include, for example, use of an inert, dry atmosphere such as nitrogen or argon, the use of dessicants such as molecular sieves, sodium sulfate, magnesium sulfate, calcium chloride, calcium sulfate, azeotropic distillation. The drying process may then preferably be repeated until the moisture content remains constant, as measured by standard moisture titration methods or other methods known in the art. (See Pangborn et al.; and Williams et al.; op. cit.) Ideally, the process is repeated until a moisture content of less than about 500 ppm is achieved. For example, the drying may be repeated until a dry polymer solution having a water content of less than about 400 ppm is attained, or more preferably less than about 300 ppm moisture is attained. Most preferably, drying is repeated until a moisture content of less than about 200 ppm is attained. In some embodiments, drying of the solvent comprises one or more azeotropic distillations. In some instances, it may be determined by experiment that some solvents or mixtures of solvents provide a lower moisture content than others. Working under a dry and inert environment (e.g., nitrogen, argon, helium), disuccinimidyl carbonate (DSC) is then added. The DSC is typically added at a ratio of about one to twenty equivalents. For example, the number of DSC equivalents may be selected from 1, 2, 3, 4, 5, 6, 7, 8, 9, 10, 11, 12, 13, 14, 15, 16, 17, 18, 19 and 20. Illustrative amounts of the DSC reagent include, for example, from about 1 to about 15 equivalents, or from about 2 to about 10 equivalents, or from about 2 to about 7 equivalents, or from about 2 to about 5 equivalents. The minimum amount of DSC for a particular reaction, e.g., to provide the best product yield and quality, should be used, as can be determined by experimentation. Typically, during addition of the DSC reagent, the reaction temperature is maintained at from about 0 -30° C. Illustrative reaction temperature sub-ranges are selected from, for example, from about 0-25° C., from about 0-20° C., from about 0-15° C., from about 5-30° C., from about 5-25° C., from about 5-20° C., and from about 10-30° C. Again, the optimum temperature for a specific reaction is can be determined by experimentation. Once the addition of the DSC reagent is completed, the temperature may then be adjusted, if necessary, to approximately 7.5 to 18° C. prior to addition of base. A base is then added to the solution comprising the polymeric hydroxymethyl fluorene derivative. For example, from about 1 to about 30 equivalents of base is added, or preferably from about 2 to about 20 equivalents of base is added, or from about 1 to 15 equivalents of base, or more preferably from about 3 to 10 equivalents of base is added. Suitable bases include amines; preferably, the base is a non-nucleophilic amine or is a weakly nucleophilic amine. Suitable bases include, for example, pyridine, 4-dimethylaminopyridine, N,N-diisopropylethylamine, 2,6-di-tert-butylpyridine, N-methylimidazole, N-ethylisopropylamine, 2,6-lutidine, 2,4,6-collidine, N,N,2,6-tetramethylpyridine-4-amine, and insoluble-polymer-bound forms of any of the foregoing (as described above). Additionally, the base may be a polyamine such as, for example, N,N,N',N'-tetramethyl-1,6-hexamethyldiamine, N,N',N',N'',N''-pentamethyldiethylenetriamine, hexamethylenetetramine, and insoluble polymer-bound forms of the foregoing polyamines.

In one or more particular embodiments, the base is pyridine or 4-dimethylaminopyridine. One skilled in the art will have knowledge regarding the types of bases that may be employed. Suitable bases for use in preparing the highest quality product of a particular polymeric hydroxymethyl fluorene active carbonate can readily be determined by experimentation, e.g., using the guidance provided herein.

The reaction (i.e., conversion to the NHS carbonate) is then carried out, preferably with agitation/mixing, while maintaining the solution temperature in a temperature range of from about 3-21° C. The reaction may take from minutes to hours depending on the structure of the polymeric reactant, the reaction temperature, the particular solvent, stirring rate, and other factors. Once the reaction is complete (the reaction progress can be monitored by any suitable means, e.g., by monitoring disappearance of the polymeric hydroxymethyl fluorene starting material by any suitable analytical technique, such as $^1$H NMR, or by monitoring the reaction exotherm using an apparatus-mounted thermocouple),the base can then be neutralized or partially neutralized. To neutralize or partially neutralize a base (e.g. pyridine or the like), the solution is typically maintained at a temperature ranging from about 3-15° C. while an acid is added. Exemplary acids include, for example, acetic acid, phosphoric acid, citric acid, sodium dibasic phosphoric acid, potassium hydrogen phosphate, sulfuric acid, chloroacetic acid, meta-nitrobenzoic acid, trifluoroacetic acid, trichloroacetic acid, p-toluenesulfonic acid, or the like. In some embodiments of the method, the acid is acetic acid, citric acid or phosphoric acid.

After an appropriate time for the acid-base reaction to subside, the reaction mixture can be filtered through an appropriate filter (to remove solids) into a sufficient volume of an anhydrous precipitating solvent, preferably a cold precipitating solvent, i.e., that is at a temperature above its freezing point but below room temperature (e.g., 20 to 25° C.). A precipitating solvent is generally an anhydrous, non-reactive solvent in which the NHS carbonate product is insoluble or is substantially insoluble (as defined previously). Precipitating solvents include, e.g, solvents such as diethyl ether, isopropyl alcohol, methyl t-butyl ether, and aliphatic hydrocarbons such as, for example, hexane and heptane, and mixtures of the foregoing. Upon introduction of or into a cold, anhydrous precipitating solvent, the desired NHS ester product typically precipitates out of solution as a solid. The precipitating solvent may preferably contain a small but appropriate amount of an acid species (e.g., chloroacetic acid or phosphoric acid), to neutralize any residual base comprised within the mixture. In one or more embodiments, the acid is selected from, but is not limited to, acetic acid, triflouroacetic acid, citric acid, sodium dibasic phosphoric acid, potassium hydrogen phosphate, sulfuric acid, m-nitrobenzoic acid, chloroacetic acid, trichloroacetic acid, phosphoric acid, p-toluenesulfonic acid or any other inorganic or organic acidic species that does not cause undesirable effects in the reactive NHS carbonate product. In one or more particular embodiments, the acid is selected from chloroacetic acid or phosphoric acid. In some preferred embodiments, the acid is phosphoric acid. The acid is generally added in an amount that is sufficient to partially or completely neutralize the base that is contained in the mixture. In some embodiments, the amount of acid that is added to the anhydrous solvent for promoting precipitation of the water-soluble 9-methyl-N-hydroxysuccinimidyl carbonate fluorene polymer comprises a small amount of acid. For example, the anhydrous precipitating solvent may comprise from about 0.0001 to about 0.5 mole percent acid. For example, the anhydrous precipitating solvent may comprise from about 0.0002 to about 0.4 mole percent acid, or from about 0.0010 to about 0.4 mole percent acid, or from about 0.0050 to about 0.3 mole percent acid. Even higher amounts of acid on a mole percentage may be required for an unusual set of reactants in a particular solvent. The optimum amount of a particular acid is preferably determined by experimentation. The minimum amount of acid for a given application is preferred.

The mixture may then be further processed by stirring with an anhydrous, cold non-solvent material (i.e., a solvent in which the product is insoluble or is substantially insoluble), such as ethyl ether or methyl t-butyl ether containing a small amount of an acidic species such as previously described, preferably the same acid as used earlier in the process, e.g., chloroacetic acid or phosphoric acid or the like. The precipitated product is then typically isolated, e.g., by filtration. As stated earlier, all process steps should be carried out in an environment that minimizes exposure to moisture. The filtered product is then preferably further washed with more anhydrous non-solvent, e.g., an ether such as diethyl ether, or methyl-t-butyl ether or other suitable precipitating solvent as described previously. The wash solvent will typically contain a small amount of an acidic species as previously described. Washes of a recovered FMOC-polymeric material, with, for example, an anhydrous precipitating solvent, may further comprise an antioxidant, such as butylated hydroxyl toluene (BHT), to avoid oxidative degradation of the polymer chain, if PEG is the polymer employed. The isolated product may then be further dried, e.g., by drying under reduced pressure (i.e., vacuum drying). Additionally, the isolated NHS carbonate product may be further purified by using standard art-known methods for purifying water-soluble polymeric reagents. One such purification method is reprecipitation. Another such preferred method is chromatography, e.g., size exclusion chromatography.

As further illustration of the methods and processes provided herein, Example 3, Part 2, II, describes the direct synthesis of the exemplary active carbonate, C2-PEG2-FMOC-NHS-20kD from C2-PEG2-FMOC-OH, 20kD.

Successful preparation of an exemplary brominated FMOC polymer, Br-G2-PEG2-FMOC-NHS-20k) employing the methods provided herein is described in Example 2. Thus, in one or more aspects, provided herein are FMOC starting materials, intermediates, and active carbonates having one or two bromo groups substituted onto the fluorene core, as shown by the following illustrative structures:

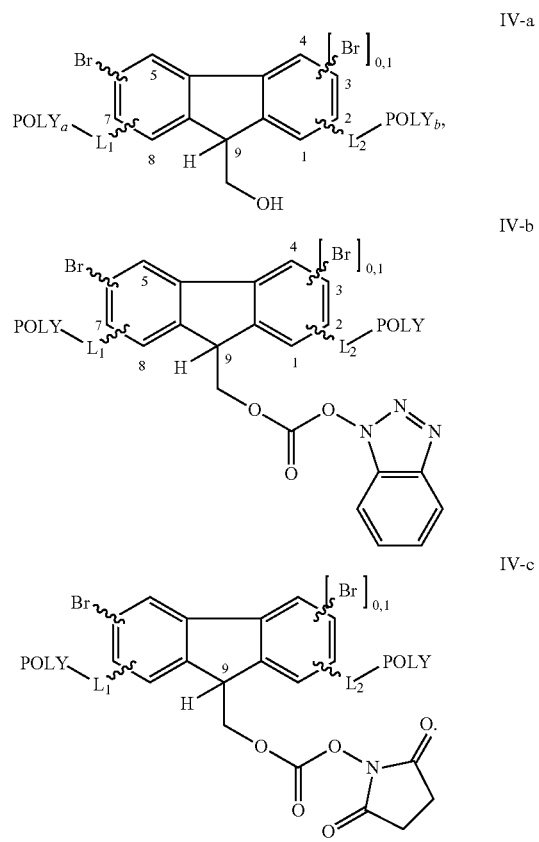

Further examples of brominated FMOC polymers include brominated versions of each of structures XI, XII, XIII, XIV, I-D, I-e, I-f, I-g, I-h, II-d, II-e, II-f, II-g, and II-h.

As the resulting polymeric FMOC-NHS carbonate reagents are subject to hydrolysis (Scheme VII, Path A) to form the original hydroxymethyl fluorene derivative, and since there is a possibility of a yet unobserved but potential thermal elimination reaction of such an activated substrate (see Meng et al. *J. Am. Chem. Soc.*, 1997, 119, 4834-4840) to form the corresponding fulvene derivative, (Scheme VII, Path B), the NHS reagents are preferably further protected by storage under a dry, inert atmosphere at low temperature, e.g. at −40° C. or lower, and more preferably at −70° C. or lower if for storage in excess of one week. Moreover, as shipping conditions of unprotected samples may lead to the reagents experiencing unacceptably high temperatures, especially during the summer, samples should, ideally be shipped with dry ice packing.

Turning now to alternate pathways for loss of reactivity of the subject polymeric FMOC reagents (other than those involving basic species as previously described): Polymeric PEG impurities are typically removed using chromatographic procedures. See, for example, McManus, S., et al., U.S. Pat. No. 8,604,159. For example, PEG carboxylic acid intermediates may be separated from neutral polyethylene glycols by chromatography using a resin such as an appropriate chromatographic medium. In the case of the fulvene formed as an impurity in the formation of the water-soluble polymer-FMOC-NHS reagents, if the fulvene is present in sufficient amounts to warrant concern, a separate purification step can be added to the process to remove the fulvene impurity. Thus, if desired, a recovered water-soluble 9-methyl N-hydroxysuccinimidyl carbonate fluorene polymer may be dissolved in an anhydrous solvent, and the resulting solution passed through a resin column containing thiol groups to allow a reactive filtration process, see Tripp et al, *Org. Lett.,* (2000), 2, 195-198, to remove the polymeric fulvene. Resins comprising appended thiol groups have been used by Dujardin, et al., Reactive and Functional Polymers (2000), 43, 123-132 to remove impurities. Such resins are commercially available, and include, for example, TENTAGEL® S SH Standard thiol resins (Rapp Polymere, Tuebingen, Germany or Advanced Chemtech, Louisville, KY) and ISOLUTE® Si-Thiol (Uppsala, Sweden). While this reactive filtration process remains a method for purification of the reactive polymeric reagents described herein, the more reactive 9-methyl N-hydroxysuccinimidyl carbonate fluorene polymers may react with the thiol-resin by thiol displacement of the succinimide moiety to leave the fluorene polymer attached to the resin, thus reducing product recovery. So, overall, it is more cost-efficient, if possible, to instead provide the subject polymeric reagents without a significant amount of the polymeric fulvene-side product using the careful application of the reaction, recovery, and purification processes otherwise described herein.

Regarding the potential for fulvene formation, during the manufacture of PEG2-FMOC reagents having linkers (L in Scheme I) that provide reduced acidity of the proton at the 9 position of the fluorene ring, e.g., the G2 series, typically, no special attention is required during the manufacturing process. While G2 and other more stable PEG FMOC reagents may not be especially unstable during their isolation, it is preferred that care is taken to neutralize all bases that may be still be present at the end of the process, e.g. pyridine, etc. Also, washing of the solid product following filtration with a non-solvent containing a small amount of an acid may provide an advantage against potential issues that may arise in storage.

With more reactive intermediates and reagents, e.g., the C2 reagent, special measures are required to prevent loss of activity of the reagent during product isolation and storage. Thus the processes described herein may be conducted, for example, to minimize moisture since water can readily hydrolyze reactive NHS carbonates and BTC intermediates. Even with special precautions to minimize the presence of basic substances (elimination initiators or catalysts), without including acids such as trifluoroacetic acid or phosphoric acid or the like for neutralization of basic species during the work-up and washing steps, loss of reagent activity will generally occur. Losses can also occur during product storage even if the reagents are stored as solids at low temperatures, since molecules residual from the process such as pyridine, DMAP, and even water, can lead to product decomposition during storage. Thus, as described herein, it is preferred to practice measures as described herein to eliminate or neutralize moisture and basic species during product isolation and purification. Moreover, the products should ideally be carefully handled during drying (e.g., under high vacuum) and bottling (e.g., dry box under inert atmosphere) to assure that no new basic substances (either charged or uncharged) are incorporated in the packaged (e.g., bottled) final reagent (product). Finally, the bottled reagent should preferably be stored until use at low temperatures, e.g. at −40° C. or lower and preferably at −70° C. or lower.

Since the elimination process to produce the PEG2 fulvene is such an important pathway to decreased reagent activity, and since it provides, as discussed above, a reactive impurity, alternate reagents and methods have been provided herein that would provide the overall end result product, but with a better conjugate yield. The FMOC NHS carbonate reagent may be favored, since it is generally preferred in reactions with proteins or polypeptides to form PEG-drug conjugates. However, as the NHS component leaving group is a better leaving group than chloride (from the respective chloroformates) or 1-hydroxybenzotriazole (from the respective BTC carbonate), then one can expect that under similar circumstances, the NHS carbonate may lead to formation of a greater amount of fulvene (when compared to the chloride or 1-hydroxybenzotriazolyl leaving groups) since that pathway is, in comparison, more favored.

Thus, if a protein to be conjugated has a highly reactive nucleophilic nitrogen (amine or other), reaction with a PEG2-FMOC-chloroformate or other reactive carbonate (e.g., a BTC carbonate) may be carried out to form the same or a similar conjugate to that formed by reaction with a PEG2-FMOC-NHS reagent. Since a resulting conjugate would be expected to possess the same release properties regardless of the reactive carbonate reagent used, the overall result provided by reaction with a non-NETS ester reagent should be favorably viewed, provided that the yield of the conjugated product is the same or better than with the NETS-carbonate reagent. Now, if, for example, a chlorocarbonate or BTC carbonate polymeric reagent exhibits a smaller loss of reagent activity (e.g., due to undergoing a slower therefore less productive conversion to the corresponding fulvene derivative in comparison to the NETS ester reagent), then the amount of intact active carbonate reagent remaining for reaction with the protein would be greater. It therefore follows that the yield of conjugate would theoretically be higher. That is to say, the choice of the leaving group in a reactive polymeric reagent is a factor that should be considered as potentially impacting the loss of reagent during one or more of manufacturing, storage and beyond, as well as potentially impacting the yield of conjugate that can be formed per mole of reagent manufactured, and ultimately delivered to the customer.

As described above, active-agent conjugates can be prepared by reaction with the polymeric reagents prepared by the methods described herein. Generally, the biologically active agent to which a polymeric reagent prepared by a method described herein is conjugated is an amine-containing biologically active agent. In some embodiments, the biologically active agent is a small molecule (e.g., a biologically active agent having a molecular weight of less than about 3,500 Daltons). In other embodiments, the biologically active agent is a macromolecule, such as a polypeptide, having a molecular weight greater than about 3,500 Daltons. Pharmacologically active polypeptides represent a preferred type of biologically active agent. It should be understood that for purposes of the present discussion, the term "polypeptide" will be generic for oligopeptides and proteins. With regard to polypeptides, the amine to which the active polymeric reagent couples can be the N-terminus and/or an amine-containing side chain of an amino acid (such as lysine) within the polypeptide. Methods for conjugating a reactive polymeric reagent such as those described herein to a biologically active agent are known to those of ordinary skill in the art.

Polymeric reagents prepared in accordance with the methods described herein will preferably contain no polymeric fulvene side products, or will contain substantially no polymeric fulvene side products. Illustrative polymeric reagents prepared in accordance with the methods provided herein contain less than 15 mole percent polymeric fulvene impurity, or preferably contain less than 10 mole percent polymeric fulvene impurity. More preferably, the polymeric reagents prepared in accordance with the methods provided herein contain less than 8 mole percent polymeric fulvene impurity, or less than 7 mole percent polymeric fulvene impurity. Even more preferably, the polymeric reagents prepared in accordance with the methods provided herein contain less than 5 mole percent polymeric fulvene impurity.

Exemplary structures of water-soluble 9-hydroxymethyl fluorene polymers for forming a polymeric active carbonate or an intermediate for forming an active carbonate, as well as exemplary structures of the polymeric intermediates and active carbonates themselves are provided herein. The following descriptions of a water-soluble polymer, an electron altering group, and a linking moiety are applicable to not only the 9-hydroxymethyl fluorene polymers, but also to the reactive carbonates formed indirectly or directly therefrom, and to the corresponding conjugates formed using the polymeric reagents resulting from the methods disclosed herein.

With respect to the structures provided herein, $POLY_a$ is a first water-soluble, non-peptidic polymer; $POLY_b$ is a second, water-soluble non-peptidic polymer; $R^{e1}$, when present, is a first electron-altering group; and $R^{e2}$, when present, is a second electron-altering group; $L_1$ is a first linking moiety; and $L_2$ is a second linking moiety. For the first and second electron altering groups, $R^{e1}$ and $R^{e2}$, a subscript of zero, e.g., $[R^{e1}]_0$, or $[R^{e2}]_0$ indicates that the electron altering group is absent (or not present), and a subscript of one, e.g., $[R^{e1}]_1$ or $[R^{e2}]_1$, indicates that the electron altering group is present.

With respect to a given water-soluble polymer, each water-soluble polymer (e.g., $POLY_a$, $POLY_b$) can comprise any polymer so long as the polymer is water-soluble and non-peptidic. Although preferably a poly(ethylene glycol), the water-soluble polymer can be, for example, other water-soluble polymers such as other poly(alkylene glycols), such as poly(propylene glycol) ("PPG"), copolymers of ethylene glycol and propylene glycol and the like, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384. The water-soluble polymer can be a homopolymer, copolymer, terpolymer, nonrandom block polymer, and random block polymer of any of the foregoing. In addition, a water-soluble polymer can be linear, but can also be in other forms (e.g., branched, forked, and the like) as will be described in further detail below. Each water-soluble polymer in the overall structure can be the same or different. It is preferred, however, that all water-soluble polymers in the overall structure are of the same type. For example, it is preferred that all water-soluble polymers within a given structure are each a poly(ethylene glycol). Further, for a given poly(ethylene glycol), each poly(ethylene glycol) can be terminally capped with an end-capping moiety selected from the group consisting of hydroxyl, alkoxy, substituted alkoxy, alkenoxy, substituted alkenoxy, alkynoxy, substituted alkynoxy, aryloxy and substituted aryloxy. A preferred terminal capping group is methoxy.

Although the weight average molecular weight of any individual water-soluble polymer can vary, the weight average molecular weight of any given water-soluble polymer reactant, intermediate, or active carbonate (i.e., the entire polymeric FMOC structure) will typically be in a range of from about 100 Daltons to about 200,000 Daltons, or from about 100 Daltons to about 150,000 Daltons. Exemplary ranges, however, include weight-average molecular weights in the following ranges: about 880 Daltons to about 5,000 Daltons (e.g., where each (n) ranges from about 10 to about 57); in the range of greater than 5,000 Daltons to about 100,000 Daltons (e.g., where each (n) ranges from about 58 to about 1136); in the range of from about 6,000 Daltons to about 90,000 Daltons (e.g., where each (n) ranges from about 68 to about 1022); in the range of from about 10,000 Daltons to about 85,000 Daltons (e.g., where each (n) ranges from about 113 to about 966); in the range of greater than 10,000 Daltons to about 85,000 Daltons (e.g., where each (n) ranges from about 114 to about 966); in the range of from about 20,000 Daltons to about 85,000 Daltons (e.g., where each (n) ranges from about 227 to about 966); in the range of from about 53,000 Daltons to about 85,000 Daltons; in the range of from about 25,000 Daltons to about 120,000 Daltons (e.g., where each (n) ranges from about 284 to about 1364); in the range of from about 29,000 Daltons to about 120,000 Daltons (e.g., where each (n) ranges from about 330 to about 1364); in the range of from about 35,000 Daltons to about 120,000 Daltons (e.g., where each (n) ranges from about 398 to about 1364); in the range of about 880 Daltons to about 60,000 Daltons (e.g., where each (n) ranges from about 10 to about 682); in the range of about 440 Daltons to about 40,000 Daltons (e.g., where each (n) ranges from about 5 to about 454); in the range of about 440 Daltons to about 30,000 Daltons (e.g., where each (n) ranges from about 5 to about 340); in a range of about 10,000 Daltons to about 25,000 Daltons (e.g., where each (n) ranges from about 113 to about 284), or in a range of about 15,000 Daltons to about 25,000 Daltons (e.g., where each (n) ranges from about 170 to about 284), and in the range of from about 40,000 Daltons to about 120,000 Daltons (e.g., where each (n) ranges from about 454 to about 1364). For any given water-soluble polymer reactant, intermediate, active carbonate reagent, etc., PEGs having a molecular weight in one or more of these ranges are preferred. In some preferred embodiments, the polymeric reagent, intermediate or reactive carbonate has an overall molecular weight of about 20,000 Daltons (where each of $POLY_a$ and $POLY_b$ has a molecular weight of about 10,000 Daltons (e.g., where each (n) is about 227). In some preferred embodiments, the polymeric starting material (reactant), intermediate or active carbonate comprises a C2 core, wherein each PEG extending from the flourenyl core ($POLY_a$ and $POLY_b$) has a molecular weight of about 10,000 Daltons. See, for example, illustrative structures XIV (NHS ester), I-h (hydroxyl reactant), and II-h (BTC), or structures corresponding to either structure XIV or II-h, where the O-succinimidyl or O-benzotriazolyl group leaving groups are replaced with another suitable leaving group well known in the art.

Exemplary weight-average molecular weights for each of POLY$_a$ and POLY$_b$ include about 100 Daltons, about 120 Daltons, about 200 Daltons, about 250 Daltons, about 300 Daltons, about 400 Daltons, about 440 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 16,000 Daltons, about 17,000 Daltons, about 18,000 Daltons, about 19,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons, about 80,000 Daltons, about 85,000 Daltons, about 90,000 Daltons, about 95,000 Daltons, and about 100,000 Daltons. Exemplary weight-average molecular weight ranges for each of POLY$_a$ and POLY$_b$ are, for example, from about 120 daltons to about 100,000 daltons (e.g., where each (n) ranges from about 3 to about 2273), or from about 250 daltons to about 60,000 daltons (e.g., where each (n) ranges from about 4.5 to about 1363). In some embodiments, weight-average molecular weight ranges for each of POLY$_a$ and POLY$_b$ are, for example, from about 120 Daltons to about 6,000 Daltons (e.g., where each (n) ranges from about 3 to about 136), or from about 6,000 Daltons to about 80,000 Daltons (e.g., where each (n) ranges from about 136 to about 1818), or from about 5,000 to about 25,000 Daltons (e.g., where each (n) ranges from about 113 to about 568), or from about 10,000 to about 25,000 Daltons (e.g., where each (n) ranges from about 227 to about 568).

As described above, POLY$_a$ and POLY$_b$ are both preferably polyethylene glycol. When a PEG is used as the water-soluble polymer in the polymeric reagent, the PEG typically comprises a number of (OCH$_2$CH$_2$) monomers [or (CH$_2$CH$_2$O) monomers, depending on how the PEG is defined]. As used throughout the description, the number of repeating units is identified by the subscript "n" in "(OCH$_2$CH$_2$)$_n$." Thus, the value of (n) typically falls within one or more of the following ranges: from 2 to about 3400, from about 4 to about 1500, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer. For example, for POLY$_a$ and POLY$_b$ wherein both are polyethylene glycol having a molecular weight of about 10,000 Daltons, the value of (n) is about 227. For POLY$_a$ and POLY$_b$ wherein both are polyethylene glycol having a molecular weight of about 20,000 Daltons, the value of (n) is about 454, and so forth.

In one or more embodiments, the fluorene moiety optionally includes one or more electron altering groups ("R$^{e1}$", "R$^{e2}$", and so forth) located at any one or more of carbons 1, 2, 3, 4, 5, 6, 7 and 8. An electron altering group is a group that is either electron donating (and therefore referred to as an "electron donating group"), or electron withdrawing (and therefore referred to as an "electron withdrawing group"). Exemplary electron withdrawing groups include halo (e.g., bromo, fluoro, chloro, and iodo), nitro, carboxy, ester, formyl, keto, azo, amidocarbonyl, amidosulfonyl, carboxamido, sulfonoxy, sulfonamide, ureido, and aryl. Exemplary electron donating groups include hydroxyl, lower alkoxy (e.g., methoxy, ethoxy and the like), lower alkyl (such as methyl, ethyl, and the like), amino, lower alkylamino, di-lower alkylamino, aryloxy (such as phenoxy and the like), arylalkoxy (such as phenoxy and the like), aminoaryls (such as p-dimethylaminophenyl and the like), mercapto, and alkylthio. In one or more embodiments, the fluorene moiety comprises one or more halo groups. More particular electron-altering groups include but are not limited to Br, —CF$_3$, —CH$_2$CF$_3$, —CH$_2$C$_6$F$_5$, —CN, —NO$_2$, —S(O)R, —S(O)Aryl, —S(O$_2$)R, —S(O$_2$)Aryl, —S(O$_2$)OR, —S(O$_2$)OAryl, —S(O$_2$)NHR, —S(O$_2$)NHAryl, —C(O)R, —C(O)Aryl, —C(O)OR, —C(O)NHR, and the like, wherein R is H or an organic radical. In some embodiments, the electron altering group is bromo. When each of R$^{e1}$ and R$^{e2}$ is different, (a) R$^{e1}$ and R$^{e2}$ can be different electron withdrawing groups, (b) R$^{e1}$ and R$^{e2}$ can be different electron donating groups, (c) or R$^{e1}$ and R$^{e2}$ can be such that one is an electron withdrawing group and the other is an electron donating group. In many circumstances, however, each of R$^{e1}$ and R$^{e2}$ will be the same.

In a fluorene ring, typical positions for addition of electron altering groups by electrophilic aromatic substitution are the "2" and "7" positions. If these positions are occupied by a linking moiety (which is attached to a water-soluble polymer) other positions on the fluorene ring will be substituted based on factors such as (a) the directing ability of the linking moiety and (b) steric influences. Often, however, the "4" and "5" positions of a fluorene ring represent the more likely sites for attachment when the "2" and "7" positions are unavailable and especially when the alpha carbon, i.e., the 9-position in fluorene (i.e., the carbon bearing an ionizable hydrogen atom, H$_\alpha$), is substituted. The electron altering groups, "R$^{e1}$", "R$^{e2}$" (when both are present), may be located on the same aromatic ring or on different aromatic rings.

The linkers, L1 and L2, between the water-soluble polymer chains, POLY$_a$ and POLY$_b$, (e.g., each polyethylene glycol chains) and the central fluorene ring may be the same or different. Typically the linkers, L1 and L2, comprise a functional group or a short chain of atoms that, for example, may be inserted during the manufacturing process. These linkers can influence the properties of the releasable polymeric reagent that is formed, and can affect the release properties of a corresponding polymer conjugate. By engineering the placement (ring position) and specific structures of the linkers, the release rate of the polymer moieties from the polymer conjugate can be altered, and can be measured, for example, typically in hours or days. Additionally, other independent functional groups, R$^{e1}$ and/or R$^{e2}$, generally referred to herein as electron-altering groups, may be, but are not necessarily, substituted onto the aromatic rings to further influence the rate of release of polymer moieties from the conjugate. For example, some illustrative R$^{e1}$ and R$^{e2}$ groups include, but are not limited to the following: halo (e.g., bromo, fluoro, chloro, and iodo), nitro, carboxy, ester, formyl, keto, azo, amidocarbonyl, amidosulfonyl, carboxamido, sulfonoxy, sulfonamide, ureido, and aryl. Exemplary electron donating groups include hydroxyl, lower alkoxy (e.g., methoxy, ethoxy and the like), lower alkyl (such as methyl, ethyl, and the like), amino, lower alkylamino, di-lower alkylamino, aryloxy (such as phenoxy and the like), arylalkoxy (such as phenoxy and the like), aminoaryls (such as p-dimethylaminophenyl and the like), mercapto, and alkylthio. More particular electron-altering groups include but are not limited to —$CF_3$, —$CH_2CF_3$, —$CH_2C_6F_5$, —CN, —$NO_2$, —S(O)R, —S(O)Aryl, —$S(O_2)$R, —$S(O_2)$Aryl, —$S(O_2)$OR, —$S(O_2)$OAryl, —$S(O_2)$NHR, —$S(O_2)$NHAryl, —C(O)R, —C(O)Aryl, —C(O)OR, —C(O)NHR, and the like, wherein R is H or an organic radical. Thus, one can design a PEG reagent of this type that will release the drug over a period of hours or a period of days, depending, for example, on the structures of $L_1$, $L_2$, and if present, $R^{e1}$ and/or $R^{e2}$, and their locations on the respective fluorenyl rings.

Exemplary linking moieties, $L_1$ and $L_2$, interposed between $POLY_a$ and/or $POLY_b$ and the fluorene moiety include, but are not limited to, —C(O)—, —$S(O_2)$—, —S(O)—, —NH—$S(O_2)$—, —$S(O_2)$—NH—, —CH=CH—, —O—CH=CH—, —C(O)—NH—, —NH—C(O)—NH—, —O—C(O)—NH—, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —S—$CH_2$—, —$CH_2$—S—, —S—$CH_2$—$CH_2$—, —$CH_2$—S—$CH_2$—, —$CH_2$—$CH_2$—S—, —S—$CH_2$—$CH_2$—$CH_2$—, —$CH_2$—S—$CH_2$—$CH_2$—, —$CH_2$—$CH_2$—S—$CH_2$—, —$CH_2$—$CH_2$—$CH_2$—S—, —S—$CH_2$—$CH_2$—$CH_2$—$CH_2$—, —$CH_2$—S—$CH_2$—$CH_2$—$CH_2$—, —$CH_2$—$CH_2$—S—$CH_2$—$CH_2$—, —$CH_2$—$CH_2$—$CH_2$—S—$CH_2$—, —$CH_2$—$CH_2$—$CH_2$—$CH_2$—S—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—, —NH—C(O)—$CH_2$—, —$CH_2$—NH—C(O)—, —NH—C(O)—$CH_2$—$CH_2$—, —$CH_2$—NH—C(O)—$CH_2$—$CH_2$—C(O)—NH—, —NH—C(O)—CH=CH—C(O)—NH—, —C(O)—O—$CH_2$—, —$CH_2$—C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—NH—C(O)—$CH_2$—$CH_2$—, —$CH_2$—$CH_2$—NH—C(O)—$CH_2$—$CH_2$—, —C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—, —$CH_2$—$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—C(O)—NH—$CH_2$—$CH_2$—NH—C(O)—, —$CH_2$—$CH_2$—, —O—C(O)—NH—[$CH_2$]$_h$—(O$CH_2$$CH_2$)$_j$—, —NH—C(O)—O—[$CH_2$]$_h$—(O$CH_2$$CH_2$)$_j$—, bivalent cycloalkyl group, —O—, —S—, an amino acid, —N($R^6$)—, and combinations of two or more of any of the foregoing, wherein $R^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific linking moieties have the following structures: —C(O)—NH—($CH_2$)$_{1-6}$—NH—C(O)—, —NH—C(O)—NH—($CH_2$)$_{1-6}$—NH—C(O)—, and —O—C(O)—NH—($CH_2$)$_{1-6}$—NH—C(O)—, wherein the subscript values following each methylene indicate the number of methylenes contained in the structure, e.g., ($CH_2$)$_{1-6}$ means that the structure can contain 1, 2, 3, 4, 5 or 6 methylenes. Additionally, any of the above linking moieties may further include an ethylene oxide oligomer chain comprising 1 to 20 ethylene oxide monomer units (i.e., —($CH_2$$CH_2$O)$_{1-20}$). That is, the ethylene oxide oligomer chain can occur before or after the linking moiety, and optionally in between any two atoms of a linking moiety comprised of two or more atoms. Also, the oligomer chain would not be considered part of the linking moiety if the oligomer is adjacent to a polymer segment and merely represent an extension of the polymer segment. Finally, it is noted that some linking moieties include an atom or group of atoms that also function as an electron altering group; in such a cases, the inclusion of one or more additional "discrete" (i.e., not a part of a linking moiety) electron altering groups may not be desired or necessary.

Preferred linking moieties for $L_1$ and $L_2$ include those selected from —C(O)—NH—$CH_2$—$CH_2$—, —$CH_2$—$CH_2$—NH—C(O)—, —C(O)—NH—$CH_2$—$CH_2$—$CH_2$—, —$CH_2$—$CH_2$—$CH_2$—NH—C(O)—, —C(O)—NH—$CH_2$—$CH_2$—$CH_2$—$CH_2$—, —$CH_2$—$CH_2$—$CH_2$—$CH_2$—NH—C(O)—, —C(O)—NH—, —NH—C(O)—, —C(O)—NH—$CH_2$—$CH_2$—$CH_2$—$CH_2$—$CH_2$—, —$CH_2$—$CH_2$—$CH_2$—$CH_2$—$CH_2$—NH—C(O)—, —NH—C(O)—$CH_2$—$CH_2$—, —$CH_2$—$CH_2$—C(O)—NH—, —NH—C(O)—$CH_2$—$CH_2$—$CH_2$—, —$CH_2$—$CH_2$—$CH_2$—C(O)—NH—, —NH—C(O)—$CH_2$—$CH_2$—$CH_2$—$CH_2$—, —$CH_2$—$CH_2$—$CH_2$—$CH_2$—C(O)—NH—, —NH—C(O)—$CH_2$—$CH_2$—, —$CH_2$—$CH_2$—$CH_2$—$CH_2$—, —$CH_2$—$CH_2$—$CH_2$—$CH_2$—, —$CH_2$—$CH_2$—C(O)—NH—, —NH—C(O)—$CH_2$—$CH_2$—C(O)—, —C(O)—$CH_2$—$CH_2$—C(O)—NH—, —NH—C(O)—$CH_2$—$CH_2$—C(O)—, —C(O)—$CH_2$—$CH_2$—C(O)—, —C(O)—$CH_2$—$CH_2$—$CH_2$—$CH_2$—C(O)—NH—, —NH—C(O)—$CH_2$—$CH_2$—$CH_2$—$CH_2$—$CH_2$—C(O)—, —C(O)—$CH_2$—$CH_2$—$CH_2$—$CH_2$—$CH_2$—C(O)—, —C(O)—$CH_2$—$CH_2$—$CH_2$—$CH_2$—$CH_2$—, —C(O)—NH—, —C(O)—$CH_2$—$CH_2$—$CH_2$—, —$CH_2$—$CH_2$—C(O)—, —C(O)—$CH_2$—$CH_2$—$CH_2$—, —$CH_2$—$CH_2$—C(O)—, —$CH_2$—$CH_2$—$CH_2$—C(O)—, —C(O)—$CH_2$—$CH_2$—$CH_2$—$CH_2$—, —C(O)—$CH_2$—$CH_2$—$CH_2$—$CH_2$—$CH_2$—, —$CH_2$—$CH_2$—$CH_2$—$CH_2$—, —$CH_2$—$CH_2$—$CH_2$—$CH_2$—C(O)—, —$CH_2$—$CH_2$—C(O)—, —NH—$CH_2$—$CH_2$—(O$CH_2$$CH_2$)$_{1-3}$—NH—C(O)—, —C(O)—NH—($CH_2$$CH_2$O)$_{1-3}$—$CH_2$—$CH_2$—NH—, —C(O)—NH—$CH_2$—$CH_2$—(O$CH_2$$CH_2$)$_{1-3}$—NH—C(O)—, —C(O)—NH—($CH_2$$CH_2$O)$_{1-3}$—$CH_2$—$CH_2$—NH—C(O)—, —NH—C(O)—$CH_2$—, —$CH_2$—C(O)—NH—, —NH—C(O)—$CH_2$—O—, —O—$CH_2$—C(O)—NH—, —$CH_2$—$CH_2$—NH—C(O)—$CH_2$—$CH_2$—$CH_2$—C(O)—NH—, —NH—C(O)—$CH_2$—$CH_2$—$CH_2$—C(O)—NH—$CH_2$—$CH_2$—, —O—$CH_2$—$CH_2$—NH—C(O)—$CH_2$—$CH_2$—$CH_2$—C(O)—NH—, —NH—C(O)—$CH_2$—$CH_2$—$CH_2$—C(O)—NH—$CH_2$—$CH_2$—O—, —C(O)—NH—$CH_2$—$CH_2$—, —$CH_2$—$CH_2$—NH—C(O)—, —C(O)—NH—$CH_2$—$CH_2$—O—, and —O—$CH_2$—$CH_2$—NH—C(O)—.

Each linking moiety, when present, in the overall structure can be the same or different than any other linking moiety in the overall structure. With respect to $L^1$ and $L^2$, it is sometimes preferred that $L^1$ and $L^2$ are the same.

Preferred linking moieties include amidocarboxy, carboxyamido, sulfonamide, ester and ureido. Further particular linking moieties include, e.g., —(CH$_2$)$_{1-6}$C(O)NH— and —NH—C(O), NH—C(O)—(CH$_2$)$_{1-6}$C(O)NH—. More particular linking moieties are selected from, for example, —(CH$_2$)C(O)NH—, —(CH$_2$)$_3$C(O)NH—, —NH—C(O), and NH—C(O)—(CH$_2$)$_3$C(O)NH—.

The linking moieties, $L^1$ and $L^2$, and thus the water-soluble polymer "arms", POLY$_a$ and POLY$_b$, may similarly be located at any two available positions on the fluorene ring, e.g., at carbon 1, 2, 3, 4, 5, 6, 7 or 8. In some embodiments, $L^1$ and $L^2$ are attached to fluorene carbons C-2 and C-7. In some other embodiments, $L^1$ and $L^2$ are attached to fluorene carbons C-2 and C-5. See, for example, illustrative structures XI, XIII, I-d, I-f, I-g, II-d, II-f, and II-g (positions C-2 and C-5) and structures XII, XIV, I-e, I-h, II-e, and II-h (positions C-2 and C-7).

The examples that follow illustrate improved methods for (i) preparing fluorenyl-based polymeric reagents, (ii) recovering and purifying such reagents, (iii) methods of reducing unwanted impurities in a fluorenyl-based polymeric reagent, (iv) methods which circumvent the use of poisonous and potentially explosive reactants, such as phosgene and DiBTC, respectively, (v) methods that convert a non-succinimidyl fluorenyl-based polymeric ester to a desired NHS-ester, among other things.

All articles, books, patents, patent publications and other publications referenced herein are incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

EXAMPLES

It is to be understood that the foregoing description as well as the examples that follow are intended to illustrate and not limit the scope of the invention(s) provided herein. Other aspects, advantages and modifications within the scope of the invention will be apparent to those skilled in the art to which the invention pertains.

Materials and Methods

This disclosure will, unless otherwise indicated, utilize conventional techniques of organic synthesis and the like, which are understood by one of ordinary skill in the art and are explained in the literature. In the following examples, efforts have been made to ensure accuracy with respect to numbers used (e.g. amounts, temperatures, and so forth), but some experimental error and deviation should be accounted for. Unless otherwise indicated, temperature is in degrees Celcius and pressure is at or near atmospheric pressure at sea level.

All radiochemical processes and analyses of radiolabeled polymers ($^1$H and $^3$H-NMR, specific activity, molecular weight using GFC with both RI and UV detectors) were conducted at Moravek Biochemicals, Inc., Los Angeles, CA, with one of the inventors present for oversight and consultation.

Except for PEG reagents, all reagents were obtained commercially unless otherwise indicated. All PEG raw materials were supplied by Nektar Therapeutics in Huntsville, Ala. All NMR data generated at Nektar Therapeutics were obtained using either 300 or 400 MHz NMR systems manufactured by Bruker (Billerica, MA). Reactions involving PEG derivatives were carried out in glass or glass-lined vessels.

Safety Warning: Before carrying out procedures with reagents bearing safety or hazard warnings, laboratory workers should become familiar with safe handling procedures to avoid serious accidents. In particular, dibenzotriazoyl carbonate (di-BTC) is an explosion hazard in certain states. These procedures should be carried out by skilled chemists or highly trained technicians.

Abbreviations:
ACN acetonitrile
anh anhydrous
BHT butylated hydroxytoluene
di-BTC dibenzotriazoyl carbonate
DCM dichloromethane
DCC N,N'-dicyclohexyl carbodiimide
DMAP 4-dimethylaminopyridine
DMF dimethylformamide
EDAC HCl 1-ethyl-3-(3'-dimethylaminopropyl)carbodiimide, HCl
HOBT hydroxybenzotriazole
IPA isopropyl alcohol
MTBE methyl-tert-butyl ether
NHS N-hydroxysuccinimide
Pyr pyridine
RB round-bottomed
RT room temperature, 20 to 25° C.
THF tetrahydrofuran Example 1

Synthesis of an Illustrative G2-PEG2-FMOC-NHS Reagent

Scheme E1—Illustration of Exemplary Reactions for the Synthesis of a G2-PEG2-FMOC-NHS Reagent via the Benzotriazole Carbonate

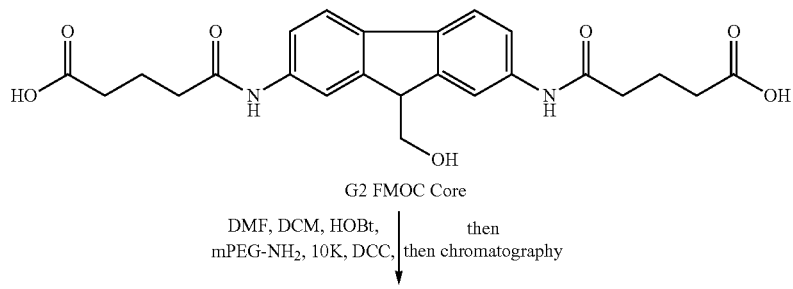

G2 FMOC Core

DMF, DCM, HOBt, mPEG-NH$_2$, 10K, DCC, then then chromatography

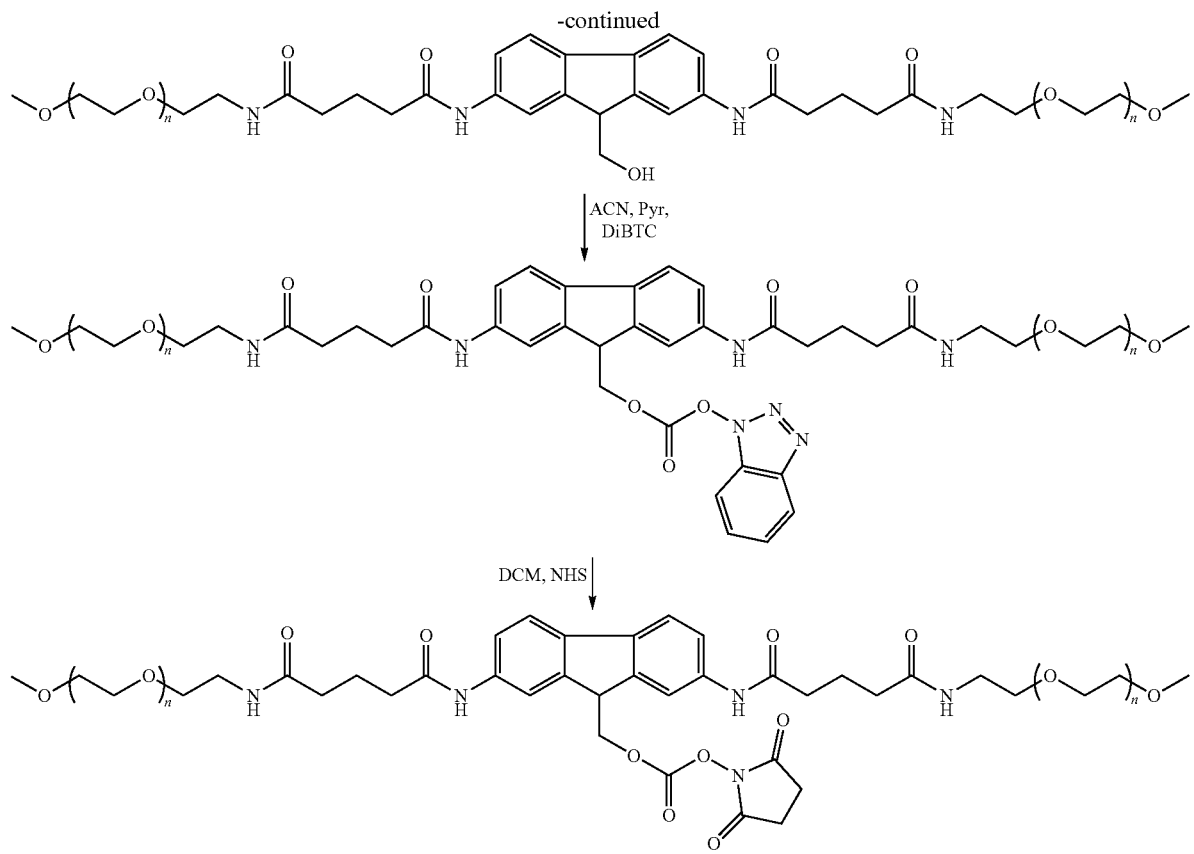

A. Preparation of G2-PEG2-FMOC-OH 20K mPEG-NH$_2$ (10,000 Da) (25.1 g, 2.51 mmol) dissolved in anhydrous toluene (250 mL) was azeotropically dried by distilling off toluene under reduced pressure at 45° C. on a rotary evaporator. The solid residue was dissolved in anhydrous dichloromethane (DCM) (125 mL) under nitrogen atmosphere. A solution of G2-FMOC-core (9-Hydroxymethyl-2,7-di(amidoglutaric acid)fluorene) (0.5211 g, 1.15 mmol) and anhydrous N-hydroxybenzotriazole (HOBt) (0.3251 g, 2.41 mmol) dissolved in anhydrous DMF (12.7mL) was added to the mPEG-NH$_2$ solution. 1,3-Dicyclohexylcarbodiimide (DCC) (0.645 g, 3.13 mmol) was then added to the solution. The reaction mixture was stirred at room temperature for 17 h. Next the solvent was distilled off under reduced pressure. The thick syrup was dissolved in anhydrous isopropyl alcohol (IPA) (300 mL, slow addition) with gentle heating. The PEG product was precipitated by addition of diethyl ether (200 mL) at room temperature. The precipitate was cooled to 10° C. for twenty minutes, filtered and washed with IPA (300 mL) and then diethyl ether (500 mL×3). The crude product was dried under vacuum giving 25 g of an off-white powder.

The crude material was dissolved in deionized water (500 mL) and diluted to a total volume of 1300 ml. The pH of the solution was adjusted to 9.7 with 1M NaOH. Chromatographic removal of unreacted mPEG-NH$_2$ (10,000) was performed on POROS HS50 media (500 mL) using water as an eluent. Fractions containing PEG product were collected and further purified by passing through DEAE Sepharose FF media (200 mL). The purified product was found to contain no mPEG-NH$_2$ (10,000) or mono PEG acid products (HPLC analysis).

A small amount of diethylenetriaminepentaacetic acid (DTPA) and sodium chloride (170 g) was added and the pH was adjusted to 7.56 with 1M NaOH. The product was extracted from the aqueous layer with DCM (250, 250, 100 mL). The DCM extract was dried with sodium sulfate, filtered and isolated with IPA and diethyl ether. The purified product was dried under vacuum (yield 20.95 g, off-white powder). GPC analysis showed 99% of the desired G2-PEG2-FMOC-OH 20K. $^1$H-NMR (CD$_2$Cl$_2$): δ (ppm): 8.6 (s, NH, 2H); 7.9 (s, Ar, 2H); 7.6 (m, Ar, 4H); 6.4 (bs, NH, 2H); 4.1 (m, CH, 1H); 4.0 (d, CH$_2$, 2H) 3.6 (bs, PEG backbone); 3.3 (s, OCH$_3$, 6H); 2.4 (t, CH$_2$, 4H); 2.3 (t, CH$_2$, 4H); 2.0 (m, CH$_2$, 4H).

B. Preparation of G2-PEG2-FMOC-BTC 20K

G2-PEG2-FMOC-OH 20K (1.8 g, 0.28 mmol) was dissolved in DCM (5 mL) and anhydrous toluene (20 mL) was added. Next, the solvents were distilled off to dryness to remove moisture and the dried material was dissolved in 5.4 mL of anhydrous acetonitrile. To this solution was added dibenzotriazolyl carbonate (di-BTC) (77 mg) and anhydrous pyridine (7.3 µL). The solution was stirred for 2 h and 15 min at RT and then anh IPA (200 mL containing 50 ppm BHT) was added to precipitate the product. After 15 min, the solution was filtered, and the solid was washed with anh IPA (45 mL containing 50 ppm BHT), and then with diethyl ether (4×50 mL containing 100 ppm BHT). The product was dried under vacuum overnight. Yield 1.49 g. $^1$H-NMR (DMSO-d6): δ (ppm) 8.6 (s, NH, 2H); 8.0 (s, Ar, 2H); 7.6 (m, Ar, 4H); 6.4 (bs, NH, 2H); 5.0 (m, CH$_2$-BTC, 2H); 4.5 (t, CH, 1H);) 3.6 (s, PEG backbone); 3.3 (s, OCH$_3$, 6H); 2.4 (t, CH$_2$, 4H); 2.3 (t, CH$_2$, 4H); 2.0 (m, CH$_2$, 4H).

C. Preparation of G2-PEG2-FMOC-NHS 20K

G2-PEG2-FMOC-BTC 20K (1.47 g) was dissolved in anh DCM (5.9 mL) and the solution was cooled to 8° C. NHS (170.6 mg) was added and the mixture was stirred overnight at 8° C. The product was precipitated by addition of IPA (60 mL containing 293 mg citric acid and 10 mg BHT), filtered off and washed with anh IPA (60 mL containing 10 mg BHT) and then with anh methyl tert-butyl ether (MTBE) (50 mL containing 35 mg citric acid and 8.2 mg BHT). Next, the product was dried under vacuum overnight. Yield 1.27 g. $^1$H-NMR (DMSO-d6): δ (ppm) 8.6 (s, NH, 2H); 7.8 (s, Ar, 1H); 7.7 (s, Ar, 2H); 7.6 (m, Ar, 4H); 6.4 (bs, NH, 2H); 4.6 (d, CH$_2$, 2H); 4.3 (t, CH, 1H), 3.6 (bs, PEG backbone); 3.3 (s, OCH$_3$, 6H); 2.8 (s, NHS, 4H); 2.4 (t, CH$_2$, 4H); 2.3 (t, CH$_2$, 4H); 2.0 (m, CH$_2$, 4H).

A product end group percent substitution of the active carbonate was determined by reaction with glycine followed by HPLC analysis of the conjugate showed 88.1 mol %.

After 136 h storage at 11° C., analysis by glycine substitution showed a percent substitution of 86.6 mol %. A similar product precipitated with no citric acid added to IPA and with no citric acid present in MTBE wash had substitution 86.2 mol % after preparation and 75.3 mol % after 136 h storage at 11° C. The G2-PEG2-FMOC-Glycine conjugate was prepared as follows: G2-PEG2-FMOC-NHS 20K (10 mg)) was dissolved in 1 mL of a buffered solution of 5% glycine (pH 7.4). The resulting solution was mixed well and reacted at room temperature for 10 min. Analysis was carried out by injecting of a sample of the solution for GFC analysis (Waters; Ultrahydrogel250; 10 mM HEPES buffer at pH 7.4, 75° C.).

Example 2

Synthesis of Brominated G2-PEG2-FMOC-NHS 20K (BR-G2-PEG2-FMOC-NHS

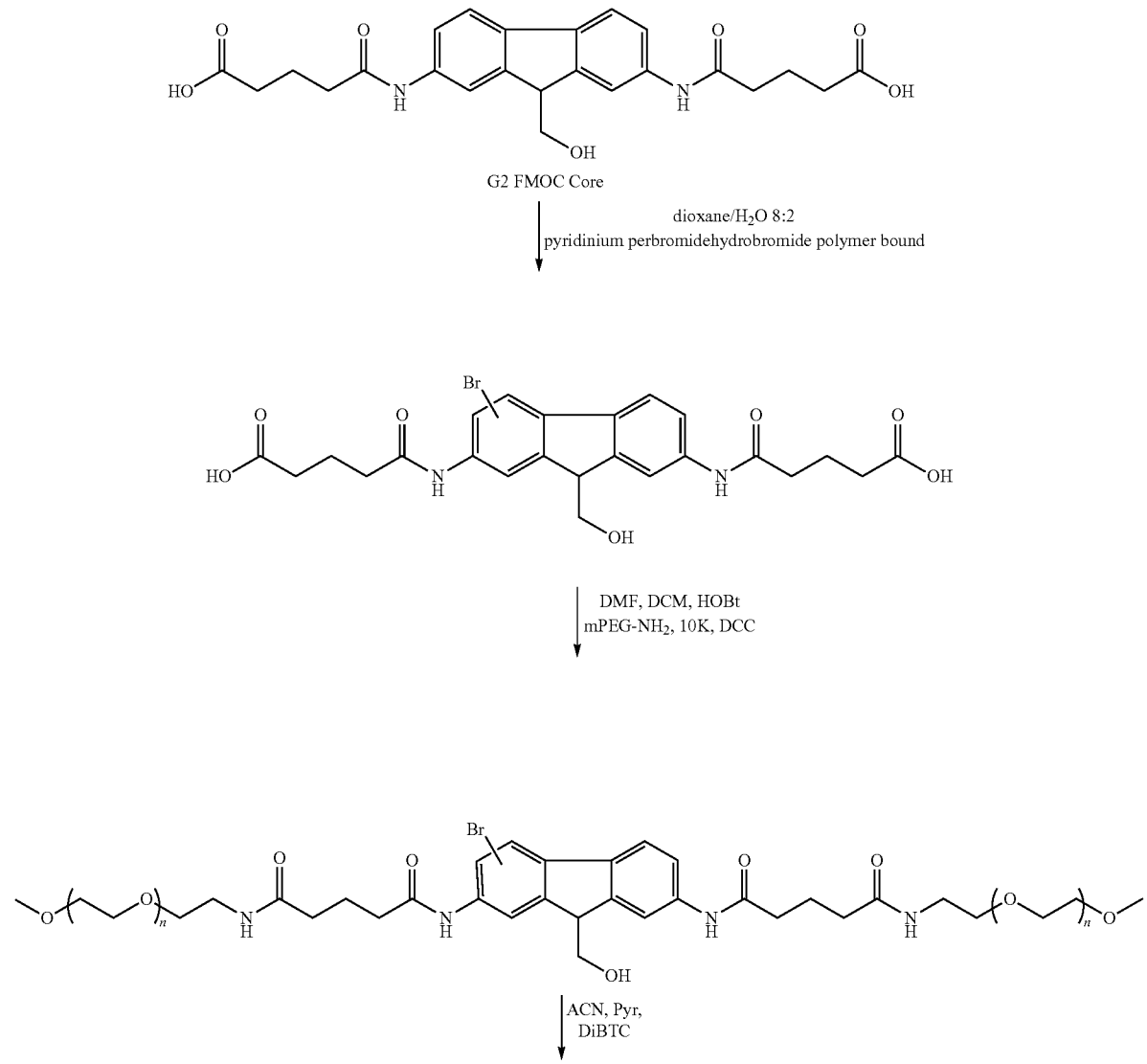

SCHEME E2 Synthesis of a Brominated G2 Reagent (Br-G2-PEG2-FMOC-NHS 20K).

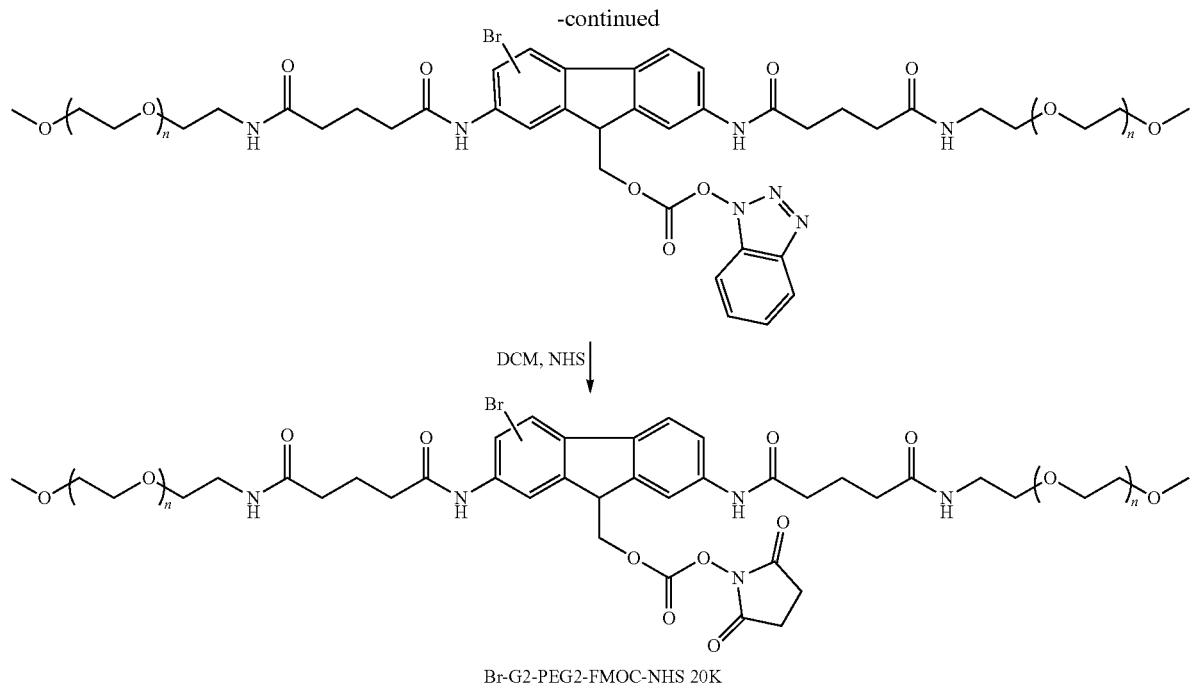

Br-G2-PEG2-FMOC-NHS 20K

A. Preparation of Brominated G2-FMOC Core (9-Hydroxymethyl-bromo-2,7-di(amidoglutaric acid)fluorene)

9-Hydroxymethyl-2,7-di(amidoglutaric acid)fluorene (1.5g, 3.3 mmol) was dissolved in 1,4-dioxane (45 mL) and deionized water (30 mL). Pyridine hydrobromide perbromide (bound on vinyl pyridine polymer, ~2 mmol $Br_3$/g resin, 25 g) was added and stirred in the dark for 2 h. The reaction suspension was filtered and washed with 1,4-dioxane/water (20 mL) and then 1,4-dioxane (20 mL). The product was extracted with half-saturated sodium chloride and ethyl acetate (400 mL×2). The organic extract was dried over anhydrous sodium sulfate, filtered and the solvent was distilled off under reduced pressure. The resulting crude product was purified by C18 silica chromatography using a 50 mM ammonium acetate (pH 4.75) and methanol gradient elution giving 0.4 g of the off-white powder. $^1$H-NMR (DMSO-d6): δ (ppm) 8.1 (s, Ar, 1H); 7.9 (s, Ar, 1H); 7.8 (m, Ar, 2H); 7.6 (d, Ar, 1H); 4.0 (t, CH, 1H); 3.7 (m, $CH_2$, 2H,); 2.4 (m, $CH_2$, 4H); 2.2 (m, $CH_2$, 4H); 1.8 (m, $CH_2$, 4H).

B. Preparation of Brominated G2-PEG2-FMOC-OH (9-Hydroxymethyl-bromo-2,7-di(mPEG(10K)-amidoglutaric amide) fluorene)

mPEG-$NH_2$ (10,000 Da) (14 g, 1.42 mmol) dissolved in anhydrous toluene (250 mL) was azeotropically dried by distilling off the solvent under reduced pressure at 50° C. on a rotary evaporator. The solid residue was dissolved in anh DCM (130 mL) under nitrogen atmosphere. A solution of brominated G2-FMOC-OH (0.315 g, 0.59 mol) and anh N-hydroxybenzotriazole (HOBt) (0.17 g, 1.24 mmol) in anh DMF (8 mL) was added to the PEG-$NH_2$ solution. 1,3-dicyclohexylcarbodiimide (DCC) (0.34 g, 1.65 mmol) was then added. The mixture was stirred at room temperature for 21 hours, and the solvent was then distilled off under reduced pressure. The thick syrup was dissolved in anh IPA (500 mL, slow addition) with gentle heating. The PEG product was precipitated by addition of diethyl ether (200 mL) at room temperature. The precipitate was cooled to 10° C. for ten minutes, filtered off and washed with cold IPA (150 mL) and with diethyl ether (150 mL) then it was dried under vacuum giving 13.2 g off-white powder.

The dried crude product was dissolved in deionized water (850 mL) and the pH was adjusted to pH 9.7 with 1M NaOH. Chromatographic removal of unreacted mPEG-$NH_2$ (10,000 Da) was performed on POROS HS50 media (500 mL) using water as an eluent. Fractions containing PEG product were collected and further purified with DEAE Sepharose media (200 mL). GPC analysis showed 93% of the desired brominated G2-PEG2-FMOC-OH product. $^1$H-NMR ($CD_2Cl_2$): δ (ppm) 8.8 (s, NH); 8.5 (s, NH); 7.9 (s, Ar, 2H); 7.8 (s, Ar); 7.7 (m, Ar); 7.6 (m, Ar); 6.6 (bs, NH); 6.4 (bs, NH); 4.1 (m, $CH_2$); 3.6 (bs, PEG backbone); 3.4 (s, $OCH_3$); 2.6 (t, $CH_2$); 2.5 (t, $CH_2$); 2.3 (m, $CH_2$).

C. Preparation of Brominated G2-PEG2-FMOC-BTC

Brominated G2-PEG2-FMOC-OH (5.6 g, 0.28 mmol) dissolved in toluene (55 mL) was azeotropically dried at 50° C. by distilling off the solvent and then dissolved in 10 mL of anhydrous acetonitrile. Next di-BTC (0.33 g, 0.50 mmol) and anhydrous pyridine (22.5 µL, 0.28 mmol) were added. The solution was stirred for 3 h at room temperature and then the product was precipitated with IPA (250 mL) and filtered off. The filtrate was washed with IPA (100 mL), and with diethyl ether (100 mL) and was then dried at rt in vacuo for 2 h. The obtained brominated G2-PEG2-FMOC-BTC was used in the next step of synthesis without additional purification. $^1$H-NMR ($CDCl_3$): δ (ppm) 9.0 (s, NH); 8.6 (s, NH); 8.1-7.5 (m, Ar); 6.9 (bs, NH); 6.8 (bs, NH); 4.9 (d, $CH_2$); 4.4 (t, CH); 3.6 (bs, PEG backbone); 3.4 (s, $OCH_3$); 2.5 (t, $CH_2$); 2.3 (t, $CH_2$); 2.0 (m, $CH_2$).

D. Preparation of Brominated G2-PEG2-FMOC-NHS (Br-G2-PEG2-FMOC-NHS 20K)

Brominated G2-PEG2-FMOC-BTC (4.71 g. 0.235 mmol) was dissolved in DCM (18.8 mL) and N-hydroxysuccinimide (NHS) (0.542 g, 4.71 mmol) was added. The reaction mixture was stirred for 22 h and was then added to IPA (200 mL) containing 0.5% acetic acid. The precipitated product was filtered off, washed with 20 mL of IPA (20 mL)

containing 0.5% acetic acid, and then with diethyl ether (60 mL) containing 0.5% acetic acid. The wet product was dried in vacuo for 2 h and then was reprecipitated by dissolving in anh acetonitrile (14.1 mL) followed by the addition of IPA (235 mL) containing 0.5% acetic acid). The precipitate was filtered off, washed with diethyl ether (60 mL) containing 0.5% of acetic acid and 0.005% BHT and dried at rt in vacuo overnight. Yield: 4.2 g. Substitution 87 mol % of active NHS ester groups. 20K. GFC analysis showed the presence of 93.3% of 20K PEG product and 6.4% of 10K PEG product. $^1$H-NMR (CD$_2$Cl$_2$) δ (ppm): 8.8 and 8.5 (s,s, NH); 8.0-7.5 (m, Ar); 6.6 and 6.4 (s, s, NH); 4.7, 4.6 (m, CH$_2$); 4.3 (m, CH); 3.6 (bs, PEG backbone); 3.4 (s, OCH$_3$); 2.8 (s, NHS); 2.5 (t,CH$_2$); 2.3 (t, CH$_2$) 2.0 (m, CH$_2$).

Example 3

Methods for Synthesis of C2-PEG2-FMOC-NHS 20K

Part 1. Synthesis of 9-Hydroxymethyl-2,7-fluorenedicarboxylic acid (C2-FMOC Core), see Scheme E3a.

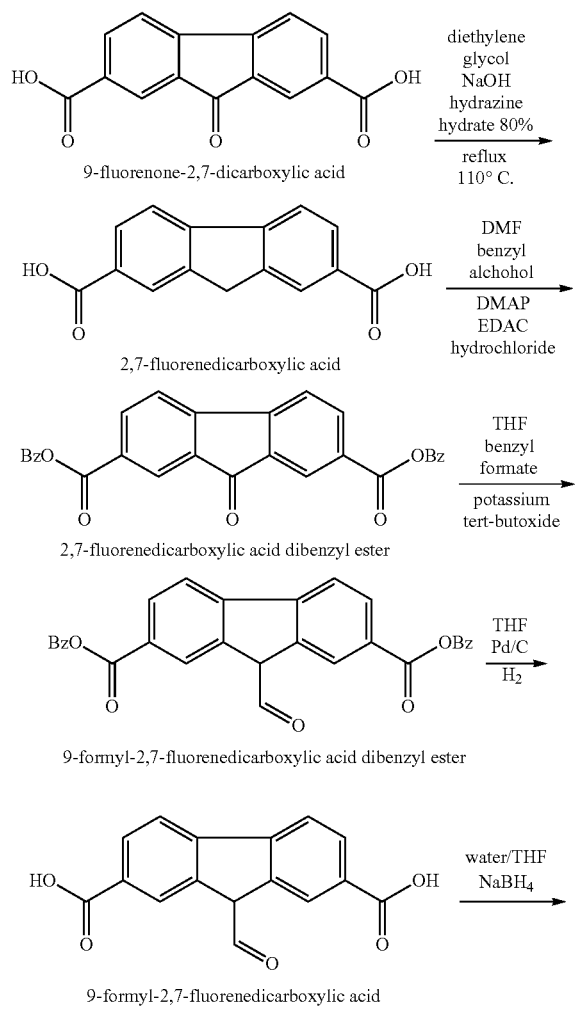

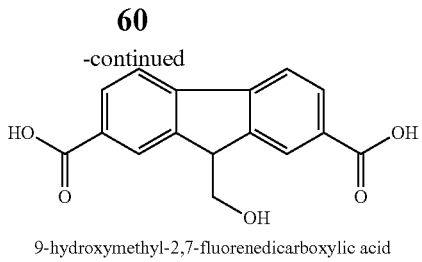

9-hydroxymethyl-2,7-fluorenedicarboxylic acid

A. Preparation of 2,7-Fluorenedicarboxylic Acid

In an argon purged flask, 9-fluorenone-2,7-dicarboxylic acid (10.0 g, 0.037 mol) was suspended in diethylene glycol (75 mL). The flask was placed in a room temperature oil bath then NaOH (6.2 g, 0.155 mol) and an 80% solution of hydrazine hydrate (7.4 mL, 0.12 mol) were added successively. The reaction mixture was slowly heated to 110° C. and then refluxed for approximately 4 hours. The reaction mixture was cooled, carefully poured into water and acidified to pH 2 with concentrated HCl. The precipitated crude product was filtered off and washed with water then it was dissolved in warm NaOH solution (0.5M) and reprecipitated by acidification to pH 2 with HCl. The precipitate was filtered and washed with water giving a solid yellow product (9.0 g, 96%). $^1$H-NMR (DMSO-d$_6$): δ (ppm) 8.2 (s, Ar, 2H); 8.1 (m, Ar, 2H); 8.0 (m, Ar, 2H); 4.1 (s, 2H, CH$_2$).

B. Preparation of 2,7-Fluorenedicarboxylic Acid Dibenzyl Ester

In a nitrogen purged dry flask, 2,7-fluorenedicarboxylic acid (8.0 g, 0.031 mol) was dissolved in anh DMF (400 mL). Next anh benzyl alcohol (82 mL, 0.788 mol), DMAP (0.58 g, 0.0047 mol) and 1-ethyl-3-(3-dimethylaminopropyl)carbodiimide (EDAC) hydrochloride (16 g, 0.082 mol) were added at rt. After stirring for 24 h diluted HCl solution (1.5 L) was added. The mixture was cooled and the solid precipitate was filtered off and washed with water. Next the product was dissolved in warm acetone (800 mL), the solution was filtered and the solvent was distilled off under reduced pressure. (Yield 5.9 g, 43%). $^1$H-NMR (DMSO-d$_6$): δ (ppm) 8.3 (s, Ar, 2H); 8.2 (m, Ar, 2H); 8.1 (m, Ar, 2H); 7.5-7.4 (m, BnO, 10H); 5.4 (s, CH$_2$, 4H); 4.1 (s, Ar, 2H).

C. Preparation of 9-Formyl-2,7-fluorenedicarboxylic Acid Dibenzyl Ester

In a dry argon purged flask, 2,7-fluorenedicarboxylic acid dibenzyl ester (3.0 g, 0.0065 mol) was dissolved in anh THF (60 mL) at room temperature. Benzyl formate (4.2 mL, 0.035 mol, stored over anh K$_2$CO$_3$) was added followed by addition of potassium tert-butoxide 95% (2.7 g, 0.023 mol). The mixture was stirred for 3 hours then the reaction was quenched with the addition of water and acidified with HCl to pH 2. The organic solvent was partially evaporated under reduced pressure. The product was extracted 2 times with ethyl acetate (600 mL then 200 mL). The combined organic layers were washed 3 times with brine, dried over sodium sulfate, filtered and the solvent was evaporated to dryness. The crude product was washed with hexanes and methanol and then was dried. Yield 1.9 g, (60%). $^1$H-NMR (DMSO-d$_6$): δ (ppm) 11.9 (s, formyl, ~1H); 8.8 (s, Ar, 1H); 8.5 (s, Ar, 1H); 8.4 (s, Ar, 1H); 8.2 (m, Ar, 2H); 7.9 (m, Ar, 2H); 7.5-7.4 (m, BnO, 10H); 5.4 (s, Ar, 4H).

D. Preparation of 9-Formyl-2,7-Fluorenedicarboxylic Acid

In a Parr hydrogenation bottle 9-formyl-2,7-fluorenedicarboxylic acid dibenzyl ester (3.0 g, 0.0061 mol) was dissolved in anh THF (350 mL). Next 20% Pd/C (wet with 50% water; 600 mg) was added and the Parr bottle was evacuated/filled 3 times on a Parr apparatus to ensure hydrogen atmosphere. The suspension was shaken under 20-30 psi of hydrogen for approximately 60 hours and then the remaining hydrogen was removed at the reduced pressure. The solution was filtered over a bed of celite, and the solvent was distilled off under reduced pressure. $^1$H-NMR (DMSO-$d_6$): δ (ppm) 9.0 (s, Ar, 1H); 8.5-8.1 (m, Ar, 6H).

E. Preparation of 9-Hydroxymethyl-2,7-fluorenedicarboxylic Acid (C2 FMOC Core or C2-FMOC-OH)

A small sample of 9-formyl-2,7-fluorenedicarboxylic acid (5-10 mg) was dissolved in water containing a small amount of THF. An excess amount of sodium borohydride was added and allowed to react for 2 h. The reaction was quenched with the careful addition of 1 M HCl. The product was extracted with ethyl acetate, dried over sodium sulfate, filtered and the solvent was distilled off dried under reduced pressure. $^1$H-NMR (CD$_3$OD): δ (ppm) 8.4 (s, Ar, 2H); 8.2 (m, Ar, 2H); 8.0 (m, Ar, 2H); 4.2 (t, CH, 1H); 4.0 (d, CH$_2$, 2H). The scaled up version of this reaction produced product that was typically 80-85% pure. Purification using Biotage column chromatography provided C2-FMOC-OH at a purity level of 98-99%.

Part 2. Methods for the Synthesis of PEG2-C2-FMOC-NHS from the C2-FMOC Core, See Schemes E3b and E3c.

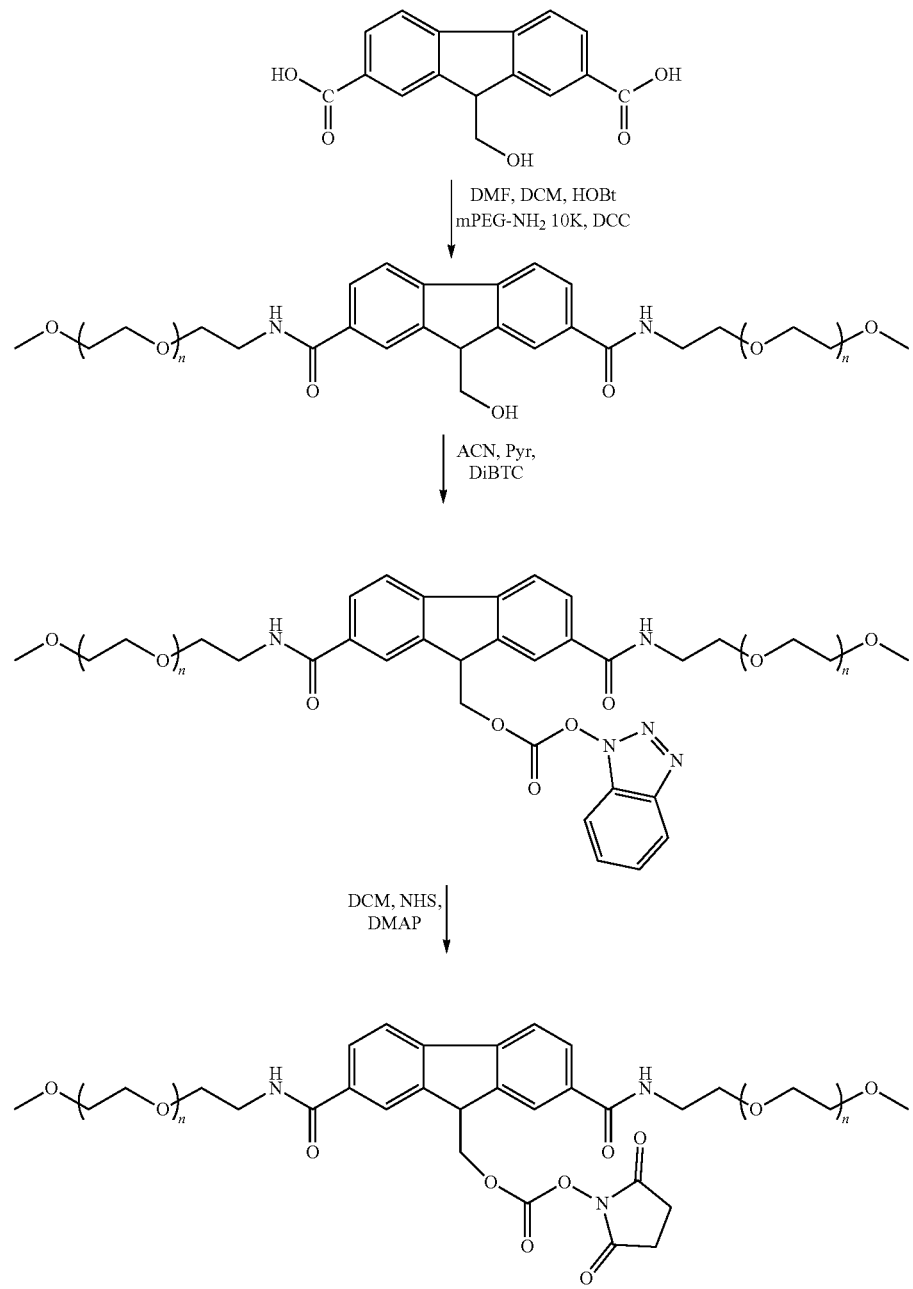

SCHEME E3b Synthesis of PEG2-C2-FMOC-NHS via PEG2-C2-FMOC-BTC 20K

I. Synthesis of C2-PEG2-FMOC-NHS via C2-PEG2-FMOC-BTC 20K

A. Preparation of C2-PEG2-FMOC-OH 20 kDa.

mPEG-NH$_2$ (Mn=10 kDa; 12.0 g) and was dissolved in anh DCM (10 mL) at 25° C. In a separate flask Biotage purified C2-FMOC-OH (0.165 g) and N-hydroxybenzotriazole hydrate (0.232 g) were dissolved in anh DMF (5.5 mL) and the resulting solution was added to the mPEG-NH$_2$ solution. Next 1.0 M solution of DCC in DCM (1.53 mL) was added and the reaction mixture was stirred 10 h at 25° C. The crude product was isolated by precipitation with the mixture of IPA (120 mL) and MTBE (350 mL). The precipitate was filtered off, rinsed with IPA (60 mL), twice with MTBE (60 mL and 130 mL) and dried under vacuum. Next the product was dissolved in 560 mL of deionized water and the pH of the solution was adjusted to pH 9.7 with 0.2 M NaOH. Ion exchange chromatography removal of unreacted mPEG-NH$_2$ was performed on POROS HS50 media (80 mL) using water as an eluent. Fractions containing PEG product were collected and further filtered through DEAE Sepharose FF media (40 mL). Sodium chloride (96 g) was added to the DEAE purified eluate and the pH of the solution was adjusted to 7.5 with 1M NaOH. The C2-PEG2-FMOC-OH 20K was extracted from the aqueous layer with DCM (120 mL). The DCM extract was dried (Na$_2$SO$_4$) and the product was precipitated with the IPA/MTBE mixture, filtered off and dried under vacuum. Yield: 11.5 g of white solid product. $^1$H-NMR (CDCl$_3$): δ (ppm) 8.2 (s, Ar, 2H); 7.9 (d, Ar, 2H); 7.8 (d, Ar, 2H); 4.2 (t, CH, 1H); 4.0 (d, CH$_2$, 2H); 3.6 (bs, PEG backbone); 3.4 (s, OCH$_3$, 6H).

B. Preparation of C2-PEG2-FMOC-BTC 20K

C2-PEG2-FMOC-OH 20K (11.0 g) dissolved in anh toluene (110 mL) was azeotropically dried by distiling off the solvent under reduced pressure. Toluene was again added and distilled off in a vacuo to dryness and the residue was dissolved in anh acetonitrile (33 mL). The obtained solution was cooled to 5° C. and di-BTC (0.50 g) and anh pyridine (56 µL) were added. The mixture was stirred at 4-6° C. for 6 h 40 min, then it was slowly added to a cooled to 5° C. IPA (275 mL) containing 0.005% phosphoric acid. After mixing for 0.5 h, cooled to 5° C. MTBE (275 mL) containing 0.005% phosphoric acid was added and the mixture was stirred for 30 min to precipitate the product. The product was filtered off and then was washed two times with 1:1 mixture of IPA/MTBE (275 mL) containing 0.005% phosphoric acid followed by second two washes with 1:1 mixture of IPA/MTBE (275 mL) containing 0.002% phosphoric acid. The resulting product, C2-PEG2-FMOC-BTC 20K, was dried under vacuum at 15° C. Yield 10.5 g $^1$H-NMR (CDCl$_3$): δ (ppm) 8.3 (s, Ar, 2H); 8.0 (d, Ar, 2H); 7.9 (d, Ar, 2H); 7.8 (d, benzotriazole, 1H); 7.6(d, benzotriazole, 1H); 7.4 (t, benzotriazole, 1H); 7.1 (t, benzotriazole, 1H); 4.8 (m, CH$_2$-BTC, 2H); 4.5 (t, CH, 1H); 3.6 (bs, PEG backbone); 3.4 (s, OCH$_3$, 6H).

C. Preparation of C2-PEG2-FMOC-NHS 20K from C2-PEG2-FMOC-BTC 20K

C2-PEG2-FMOC-BTC (10.0 g) was dissolved in anh DCM (40 mL). With stirring, solid NHS (0.60 g) was added and mixed for a minimum of 15 min keeping the temperature at −5 to −10° C. While maintaining the reaction temperature constant, an equivalent amount of anhydrous DMAP (0.030 g) was added and the reaction mixture was stirred 20 hours until an NMR analysis showed that C2-PEG2-FMOC-BTC has been converted to the NHS product. Next the mixture was added to IPA (250 mL) containing trifluoroacetic acid (TFA) (0.30 mL) at the temperature −5° C. A cold MTBE (250 mL) was added and the precipitated product was filtered off and washed with cold 1:1 mixture of IPA/MTBE (250 mL) containing 0.01% TFA. The washing step was repeated and the precipitate was further washed with cold 1:1 mixture of IPA/MTBE (500 mL) containing 0.01% phosphoric acid, followed by twice washing with cold MTBE (250 mL) containing 0.01% phosphoric acid. The wet product, C2-PEG2-FMOC-NHS 20K, was dried under vacuum overnight. Yield 9.5 g. $^1$H NMR (CDCl$_3$): δ (ppm) 8.1 (s, Ar, 2H); 8.0 (d, Ar, 2H); 7.9 (d, Ar, 2H); 4.7 (d, CH$_2$, 2H); 4.5 (t, CH, 1H); 3.6 (bs, PEG backbone); 3.4 (s, OCH$_3$, 6H); 2.9 (s, NHS).

II. Direct Synthesis of C2-PEG2-FMOC-NHS 20K from C2-PEG2-FMOC-OH 20K

Scheme E3c Synthesis of C2-PEG2-FMOC-NHS directly from C2-PEG2-FMOC-OH 20K

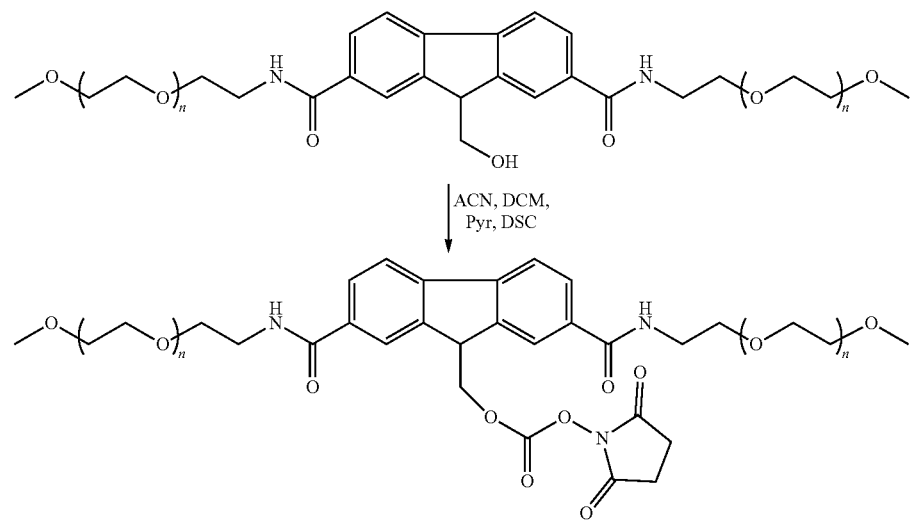

C2-PEG2-FMOC-OH 20K (5.0 g) dissolved in 100 mL of anh DCM was azeotropically dried by distilling off the solvent under reduced pressure. The drying process was repeated and the residue was dissolved in anh DCM (25 mL). While maintaining an inert atmosphere (dry nitrogen)

through the process, disuccinimidyl carbonate (DSC) (0.130 g, 2.0 equiv) was added maintaining a bath temperature at approximately 15° C. The temperature was lowered to 10° C., pyridine (0.101 mL, 5.0 equiv) was added and the mixture was stirred 20 h at 8-10° C. Then it was cooled to 5° C., TFA (0.19 mL, 10 equiv) was added and the stirring was continued for about 0.3 h. The solution was filtered through a 0.2 micron filter and added at 5° C. to 100 mL of cold IPA (100 mL) containing 0.1% TFA. The mixture was stirred for about 3.0 h and then cold MTBE (100 mL) containing 0.1% TFA was added. The precipitated product was filtered off, washed with MTBE (200 mL and 100 mL containing 0.1% of phosphoric acid) and dried under vacuum for 12 h. $^1$H-NMR (CDCl$_3$): δ (ppm) 8.1 (s, Ar, 2H); 8.0 (d, Ar, 2H); 7.9 (d, Ar, 2H); 4.7 (d, CH$_2$, 2H); 4.5 (t, H, CH); 3.6 (bs, PEG backbone); 3.4 (s, OCH$_3$, 6H); 2.9 (s, NHS).

Example 4

Method for the Synthesis of $^3$H-G2-PEG2-FMOC-NHS 20K by Tritium Exchange

Tritium Exchange on G2-PEG2-FMOC-OH 20K

G2-PEG2-FMOC-OH 20K from Example 1 (1.2 g), was dissolved in 7.2 mL of phosphate buffer pH 8.5 and palladium hydroxide on the active carbon (0.42 g, 20% Pd content (dry basis), moist with water 52%) was added. The suspension was sparged with argon for 30 min and then was frozen with liquid nitrogen. The frozen solution was then exposed tritium gas, allowed to warm to rt and then blanketed with tritium for 4.5 h. The tritium gas was pumped out of the vessel and approximately 50 mL of DI water was added. The solution was filtered to remove the palladium catalyst. Water was distilled in vacuo at ambient temperature to remove residual tritium gas and then redissolved in 20 mL DI water. The labeled PEG was stored as frozen aqueous solution overnight. After thawing the sample at rt, sodium chloride (8.5 g) was added and the pH was adjusted to pH 7.1 with dilute phosphoric acid. The labeled PEG was then extracted with DCM (3×20 mL), dried over sodium sulfate (9 g), and filtered. The DCM was evaporated under argon. The PEG was dissolved in DCM (5 mL) and anh toluene (20 mL) and the solvent was evaporated under argon to give $^3$H-G2-PEG2-FMOC-OH 20K (9) Yield was 0.96 g. $^1$H-NMR (CD$_2$Cl$_2$): δ (ppm) 8.8, 8.7 (s, s, NH); 7.9 (d, Ar); 7.6-7.4 (m, Ar); 6.5 (bs, NH); 4.0 (m, CH, CH$_2$); 3.6 (s, PEG backbone); 3.3 (s, OCH$_3$); 2.4 (t, CH$_2$); 2.3 (t, CH$_2$); 2.0 (m, CH$_2$).

Preparation of the Active Carbonate $^3$H-G2-PEG2-FMOC-NHS 20K

3H-G2-PEG2-FMOC-OH 20K (0.96 g) was dissolved in anh acetonitrile (3 mL). Di-BTC) (67 wt % slurry in trichloroethane, 48 mg) and anh pyridine (4 μL) was added and the reaction mixture was stirred for 2 hours. The product was precipitated with IPA (50 mL, containing BHT 50 ppm), chilled on ice, filtered off and washed with IPA (50 mL, containing BHT 50 ppm) and then with anh diethyl ether (200 mL, containing BHT 50 ppm).

The obtained $^3$H-G2-PEG2-FMOC-BTC 20K was dissolved in anh DCM (3.0 mL). NHS (90.1 mg) was added and the reaction mixture was stirred at 4° C. overnight. Next anh IPA (40 mL, containing citric acid and BHT) was added. The suspension was cooled on the ice batch for 10 minutes then the precipitate was filtered off and washed with anh IPA (40 mL) containing BHT and with anh MTBE (100 mL) containing citric acid and BHT. The obtained product was dried under vacuum for about 4 hours. Yield 663 mg, 54% active NHS by HPLC of glycine conjugate. $^1$H-NMR (CD$_2$Cl$_2$): δ, (ppm) 8.8, 8.7 (s, s, NH); 7.9-7.4 (m, Ar); 6.8 (bm, NH); 4.6 (m, CH); 4.3 (m, CH$_2$); 3.6 (s, PEG backbone); 3.3 (s, OCH$_3$); 2.8 (s, CH$_2$); 2.5 (t, CH$_2$); 2.3 (t, CH$_2$); 2.0 (m, CH$_2$). Specific activity was 7.0 Ci/mmol. Analysis by GPC showed 88% 20K MW with the remained both low and high MW fractions.

The material was split into 3 portions (each 220 mg) for storage stability analysis at −80° C. Product for solid storage (220 mg) was divided into aliquots of 40 mg each and stored at −80° C. for later analysis. Another product portion (220 mg) was dissolved in anhydrous dichloromethane (4.4 mL) and stored at −80° C. in 1 mL aliquots. The remaining product (220 mg) was dissolved in 2 mM HCl solution (2.2 mL, pH=2.55) and placed at −80° C. in 0.5 mL aliquots. Sample aliquots were analyzed for MW and % substitution to observe the effects of radiolysis at different storage conditions. The results at 14 days are summarized in Table 1.

TABLE 1

Storage form stability for $^3$H-G2-PEG2-FMOC-NHS 20K.

| | Storage Form @ production | | | |
|---|---|---|---|---|
| | % Sub | MW >20K | MW 20K | MW <20K |
| | 54% | 6% | 88% | 6% |
| @14 days | | | | |
| Solid | 49% | 10% | 76% | 14% |
| 2 mM HCl | 42% | 12% | 79% | 9% |
| Dichloromethane | 53% | 8% | 85% | 7% |
| Glycine Conjugate pH 5.9 | 37% | 8% | 84% | 9% |

Example 5

Method for the Synthesis of $^3$H—C2-PEG2-FMOC-NHS 20K by Tritium Exchange

Tritium Exchange on mPEG-NH$_2$ 10 kDa mPEG amine 10 kDa (2.0 g) was dissolved in 100 mM phosphate buffer pH 8.55 with and palladium hydroxide on the active carbon (0.71 g, 20% Pd content (dry basis), moist with water (50%) was added. The suspension was sparged with argon for 30 min and then was frozen with liquid nitrogen. The frozen solution was then exposed to tritium gas, allowed to warm to rt and then blanketed with tritium for 3 h. Tritium gas was pumped out of the vessel and approximately 70 mL DI water was added. The solution was filtered to remove the palladium catalyst. Water was distilled off in vacuo at ambient temperature to remove residual tritium gas and the residue was redissolved in 20-30 mL DI water. Distillation and addition of water was repeated 3 times and the final solid was dissolved in ~30 mL DI water.

NaCl (3 g) was added and the pH was adjusted to 9.5 with sodium hydroxide solution. The product was extracted with DCM (25 mL×3; 5 mL×1), the extract was dried (Na$_2$SO$_4$). Next the solvent was distilled off under reduced pressure giving the solid $^3$H-mPEG-NH$_2$ 10 kDa product, 2.06 g. The specific activity for the product was 11.59 Ci/mmol. To lower the specific activity, the tritiated product was diluted with unlabeled mPEG amine 10 kDa. Thus to the tritium labeled sample from above was added unlabeled mPEG amine 10 kDa (2.0 g) and the resulting mixture was dissolved in DCM (6 mL). The diluted PEG amine was precipitated from the solution by addition of IPA (150 mL, containing BHT 100 ppm) and diethyl ether (150 mL) and then filtered. The precipitate was washed with diethyl ether (containing BHT 100 ppm) and dried under vacuum (~30 min); yield 3.0 g, specific activity: 6.7 Ci/mmol.

Preparation of $^3$H—C2-PEG2-FMOC-OH 20 kDa

The labeled mPEG amine ($^3$H-mPEG-NH$_2$ 10 kDa) (3.0 g) and HOBt hydrate (46 mg, 0.28 mmol, 2.1 eq.) were dissolved in DCM (10 mL) and toluene (10 mL). The solvent was removed in vacuo at 25° C. and the residue was dried under nitrogen flow for about 20 min. In a separate flask C2-FMOC-OH core (38.7 mg, 0.135 mmol, 1.0 eq.) was dissolved in anh DMF (2.2 mL). Next the solvent was removed in vacuo at 50° C. The dried C2-FMOC-OH core material was dissolved in anh DMF and transferred (2.2 mL dissolution, 1.0 mL transfer) to the mPEG amine containing HOBt solution. DCC (86.0 mg, 0.42 mmol, 3.1 eq.) was added and the mixture was stirred overnight at room temperature. The crude product was isolated with IPA (120 mL), filtered off, rinsed with diethyl ether (40 mL) and dried under vacuum. Next it was dissolved in deionized water (120 mL) and the solution was diluted with an additional 180 mL of deionized water. The pH of the solution was adjusted to pH 9.7 with 1M NaOH. Chromatographic removal of unreacted labeled mPEG-NH$_2$ (10,000 Da) was performed on POROS HS50 media (40 mL) using water as an eluent. Fractions containing neutral PEG were collected and further purified by the filtration through DEAE Sepharose media (30 mL). A Diethylenetriaminepentaacetic acid (DTPA) solution and sodium chloride (170 g) were added and the pH was adjusted to 7.50 with 1M NaOH. The product was extracted with DCM (120 mL total). The extract was dried with sodium sulfate, filtered, and IPA and diethyl ether were added. The precipitated product was dried under vacuum. Yield 1.53 g, specific activity: 11.6 Ci/mmol.

Preparation of the Active Carbonate $^3$H-C2-PEG2-FMOC-NHS 20 kDa.

The labeled intermediate $^3$H-C2-PEG2-FMOC-OH 20 kDa was converted to $^3$H-C2-PEG2-FMOC-NHS 20 kDa by activation to active benzotriazolyl carbonate ($^3$H-C2-PEG2-FMOC-BTC) carbonate and then displacement with NHS as described in Example 3. The yield of the labeled $^3$H-C2-PEG2-FMOC-NHS 20 kDa product was 1.24 g. 86% active NHS by HPLC of glycine conjugate. $^1$H-NMR (CD$_2$Cl$_2$; 300 MHz): δ (ppm) 8.0, 7.9 (d, d, Ar); 8.0 (s, Ar); 4.7 (d, CH2); 4.5 (t, CH); 4.3 (m, CH$_2$); 3.6 (s, PEG backbone); 3.3 (s, —OCH$_3$); 2.9 (s, CH$_2$). Specific activity was 11.8 Ci/mmol. GFC: 3.1% high MW, 90.1% product, 6.8% LMW.

Example 6

Release Rates of Glycine Conjugates

For the measurement of release rates of the model drug conjugates, glycine conjugates were prepared from the G2, Br-G2, and C2 PEG2-FMOC 20K NHS reagents using the procedure in Example 1. The results of the new structures are compared in Table 2 with structures previously described.

Release data for G2-PEG2-FMOC-20K-glycine carbamate conjugate at 37° C. and pH 7.4: 15 days (one experiment), which agrees with the previously reported value (Bentley et al, U.S. Pat. No. 8,252,275).

Release data for Br-G2-PEG2-FMOC-20K-glycine carbamate conjugate at 37° C. and pH 7.4: 2.3 days (one experiment).

Release data for C2-PEG2-FMOC-20K-glycine carbamate conjugate at 37° C. and pH 7.4: 1.0±0.06 days (duplicate experiments).

TABLE 2

Half-lives of Glycine Conjugates of PEG2-FMOC Reagents at 37° C., pH 7.4.

| Reagent | 4,7-CAC[a] | 2,7-G2 | 4,7-CG[a] | Br-2,7-G2 | 2,7-C2 |
|---|---|---|---|---|---|
| Half-life | 18 d | 15 d | 4 d | 2.3 d | 1.0 d |

[a]Data from Bentley et al., U.S. Pat. No. 8,252,275

Example 7

Detection of Fulvene Content in C2-PEG2-FMOC-NHS-20kDa

Various lots of C2-PEG2-FMOC-NHS-20kDa were prepared as generally described in U.S. Pat. No. 8,252,275. The various lots were analyzed for C2-PEG2-fulvene content by HPLC.

| Lot No. | Fulvene Content, Mol %, HPLC |
|---|---|
| 181 | 4.8 |
| 182 | 7.4 |
| 183 | 5.9 |
| 184 | 6.6 |
| 185 | 5.4 |
| 186 | 6.6 |
| 187 | 7.0 |

Example 8

Removal of PEG Fulvene Impurities by Reaction of C2-PEG2-Fulvene with 3-Mercaptopropionic Acid Followed by Chromatographic Purification

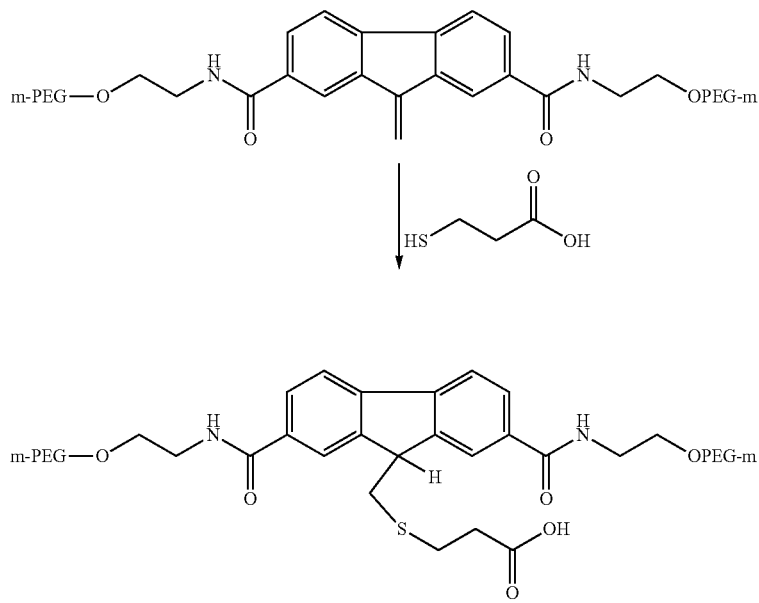

In a stirred round bottomed flask, a 90:10 mixture of 2,7-C2-PEG2-FMOC-OH 20K and 2,7-C2-PEG2-Fulvene 20K (25 mg), the latter prepared as described by Culbertson et al (U.S. Pat. No. 8,905,235), was dissolved in a buffer solution of 50 mM HEPES containing 10 mM 3-mercaptopropionic acid (pH 6.8) and the reaction allowed to proceed for 2 h. The reaction mixture was then subjected to chromatographic removal of the resultant 2,7-C2-FMOC-Acid using a DEAE Sepharose FF column. Reversed phase HPLC analysis of the product (Waters 2695 HPLC system, C4 column, 10 mM $K_2HPO_4$— THF gradient, ambient temperature, 0.5 mL/min flow rate, and UV detection (300 nm)), indicated that the purified 2,7-C2-PEG2-FMOC-OH 20K contained only trace yet detectable amounts of 2,7-C2-FMOC-Fulvene 20K (~0.2 wt %). The purified product contained no 2,7-C2-FMOC-Acid 20K.

This example illustrates yet another method for removing a fulvene impurity from a 9-hydroxymethyl fluorene polymer. In this approach, the impurity, fulvene, is removed from a 9-hydroxymethyl fluorene polymer (that is, any of the exemplary 9-hydroxymethyl fluorene polymers described herein) by reaction with an exemplary bifunctional reactant, a thiol-carboxylic acid, in this instance, 3-mercaptopropionic acid. The reactant includes a thiol group for selective reaction with the fulvene double bond (and not the 9-hydroxymethyl fluorene polymer), and a carboxylic acid group to facilitate chromatographic removal of the resultant 2,7-C2-FMOC-acid reaction product, e.g., by ion exchange chromatography. Reactants suitable for use in this method include, for example, C1-C10 mercaptoalkanoic acids such as, for example, $HS(CH_2)_{1-9}C(O)OH$. Although fulvene formation can occur during formation of any of a number of FMOC species, such as for example, the 9-hydroxymethyl fluorene polymers, as well as during formation of the corresponding esters and the like, this approach is not applicable to FMOC reagents that are sensitive to hydrolysis, such as the BTC and NHS esters.

It is claimed:

1. A method for preparing a reactive polymeric reagent, said method comprising:

(i) reacting a water-soluble 9-hydroxymethyl fluorene polymer having a structure (I):

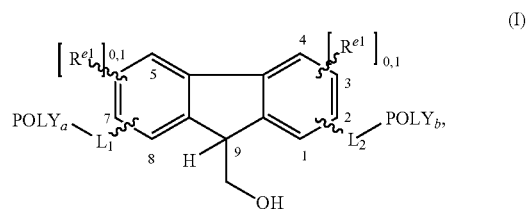

wherein $POLY_a$ is a first water-soluble, non-peptidic polymer;

$POLY_b$ is a second, water-soluble non-peptidic polymer;

$R^{e1}$, when present, is a first electron-altering group; and $R^{e2}$, when present, is a second electron-altering group;

$L_1$ is a first linking moiety; and $L_2$ is a second linking moiety;

with dibenzotriazolyl carbonate in an aprotic organic solvent in the presence of a base under anhydrous conditions to provide a reaction mixture comprising a water-soluble 9-methyl benzotriazolyl carbonate fluorene polymer having a structure:

(II)

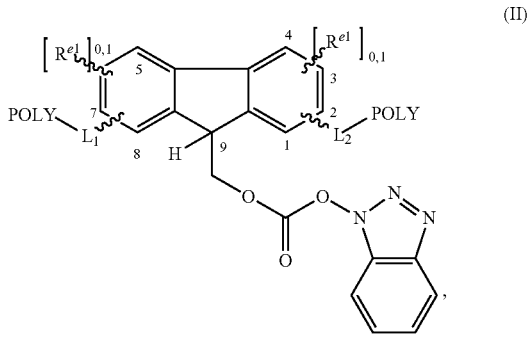

wherein POLY$_a$, POLY$_b$, R$^{e1}$, R$^{e2}$, L$_1$, and L$_2$ each have values as described in step (i), and (ii) recovering the water-soluble 9-methyl benzotriazolyl carbonate fluorene polymer (II) by precipitation with an anhydrous solvent effective to promote precipitation of the water-soluble 9-methyl benzotriazolyl carbonate fluorene polymer.

2. The method of claim 1, wherein step (i) comprises reacting the water-soluble 9-hydroxymethyl fluorene polymer of structure (I) with from about 1 to about 30 equivalents of dibenzotriazolyl carbonate.

3. The method of claim 1, wherein the base is an amine.

4. The method of claim 3, wherein the base is a non-nucleophilic amine or is a weakly nucleophilic amine.

5. The method of claim 3, wherein the base is selected from the group consisting of pyridine, 4-dimethylaminopyridine, N,N-diisopropylethylamine, 2,6-di-tert-butylpyridine, N-methylimidazole, N-methylmorpholine, 2,6-lutidine, 2,4,6-collidine, N,N,2,6-tetramethylpyridine-4-amine, N,N,N',N'-tetramethyl-1,6-hexamethyldiamine, N,N',N',N'',N''-pentamethyldiethylenetriamine, hexamethylenetetramine, and insoluble-polymer-bound forms of any of the foregoing.

6. The method of claim 1, wherein step (i) comprises from about 1 to about 30 equivalents of base.

7. The method of claim 6, wherein step (i) comprises from about 1 to about 10 equivalents of base.

8. The method of claim 1, wherein step (i) is carried out under a dry and inert gas atmosphere.

9. The method of claim 1, wherein step (i) is carried out with mechanical agitation.

10. The method of claim 1, wherein the reacting step is carried out at a temperature in a range of from about −20° C. to about 35° C.

11. The method of claim 10, wherein the reacting step is carried out at a temperature in a range of from about −10° C. to about 25° C.

12. The method of claim 10, wherein the reacting step is carried out at a temperature in a range of from about −5° C. to about 10° C.

13. The method of claim 1, where the water-soluble 9-hydroxymethyl fluorene polymer of step (i) is dissolved in the anhydrous, aprotic organic solvent.

14. The method of claim 1, where in step (ii), the anhydrous solvent effective to promote precipitation further comprises an acid.

15. The method of claim 14, wherein the anhydrous solvent effective to promote precipitation of the water-soluble 9-methyl benzotriazolyl carbonate fluorene polymer comprises from about 0.0001 to about 0.5 mole percent acid.

16. The method of claim 14, where the acid is selected from the group consisting of acetic acid, phosphoric acid, citric acid, sodium dibasic phosphoric acid, potassium, hydrogen phosphate, sulfuric acid, meta-nitrobenzoic acid, trifluoroacetic acid, and trichloroacetic acid, p-toluenesulfonic acid.

17. The method of claim 16, wherein the acid is selected from acetic acid, citric acid and phosphoric acid.

18. The method of claim 17, wherein the acid is phosphoric acid.

19. The method of claim 1, further comprising, prior to the reacting step, dissolving the water-soluble 9-hydroxymethyl fluorene polymer of structure (I) in the aprotic organic solvent to form a polymer solution, and drying the polymer solution by azeotropic distillation to provide a polymer solution having a water content of less than 500 ppm.

20. The method of claim 1, wherein the recovered water-soluble 9-methyl benzotriazolyl carbonate fluorene polymer from step (ii) comprises less than 10 mole percent of a water-soluble fulvene polymer.

21. The method of claim 1, wherein the dibenzotriazolyl carbonate in step (i) is in a halogenated solvent.

22. The method of claim 21, wherein the halogenated solvent is a chlorinated solvent that is either dichloromethane or trichloroethylene.

23. The method of claim 1, wherein the aprotic organic solvent from step (i) is selected from dimethylformamide, acetone, acetonitrile, dioxane, and tetrahydrofuran.

24. The method of claim 14, wherein the recovering step comprises filtering the reaction mixture from step (i) to remove solids to provide a solution comprising the water-soluble 9-methyl benzotriazolyl carbonate fluorene polymer, followed by adding an amount of the anhydrous solvent effective to precipitate the water-soluble 9-methyl benzotriazolyl carbonate fluorene polymer from the solution.

25. The method of claim 1, further comprising isolating the recovered precipitated water-soluble 9-methyl benzotriazolyl carbonate fluorene polymer by filtration.

26. The method of claim 1, wherein the anhydrous solvent in step (ii) is miscible with the aprotic organic solvent from step (i), and is a solvent in which the water-soluble 9-methyl benzotriazolyl carbonate fluorene polymer is substantially insoluble.

27. The method of claim 1, wherein the anhydrous solvent effective to promote precipitation of the water-soluble 9-methyl benzotriazolyl carbonate fluorene polymer is selected from diethyl ether, isopropyl alcohol, methyl-t-butyl ether, pentane, hexane, heptane, and mixtures of the foregoing.

28. The method of claim 1, further comprising washing the recovered water-soluble 9-methyl benzotriazolyl carbonate fluorene polymer with an anhydrous solvent in which the water-soluble 9-methyl benzotriazolyl carbonate fluorene polymer is substantially insoluble, the solvent comprising from about 0.0001 to about 0.5 mole percent acid.

29. The method of claim 1, further comprising (iii) purifying the recovered water-soluble 9-methyl benzotriazolyl carbonate fluorene polymer.

30. The method of claim 1, comprising converting the recovered water-soluble 9-methyl benzotriazolyl carbonate fluorene polymer to a different reactive carbonate.

31. The method of claim 30, wherein the different reactive carbonate is a water-soluble 9-methyl N-hydroxy succinimidyl carbonate fluorene polymer.

32. The method of claim 31, wherein the converting reaction is carried out by reacting the recovered or purified water-soluble 9-methyl benzotriazolyl carbonate fluorene polymer with N-hydroxysuccinimide in dichloromethane.

33. The method of claim 32, wherein the converting reaction is carried out in the presence of dimethylaminopyridine.

34. The method of claim 1, wherein each of POLY$_a$ and POLY$_b$ is a polyethylene glycol.

35. The method of claim 34, wherein each POLY$_a$ and POLY$_b$ is a polyethylene glycol having a weight average molecular weight of from about 120 daltons to about 100,000 daltons, or from about 250 daltons to about 60,000 daltons, or from about 5,000 daltons to about 25,000 daltons.

36. The method of claim 35, wherein each POLY$_a$ and POLY$_b$ is a polyethylene glycol having a weight average molecular weight of from about 250 daltons to about 60,000 daltons.

37. The method of claim 1, wherein the water-soluble 9-hydroxymethyl fluorene polymer of structure (I) has a structure:

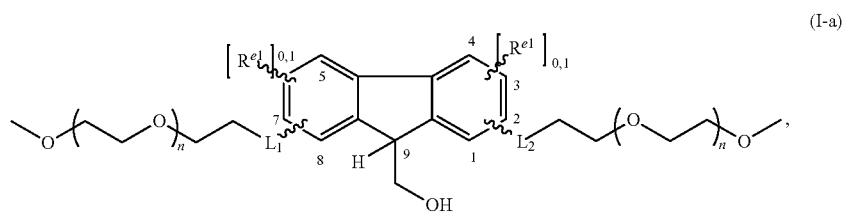

wherein each n independently ranges from about 3 to about 2273, or from about 4 to about 1363, or from about 3 to about 136, or from about 136 to about 1818, or from about 113 to about 568, or from about 227 to about 568; and the water-soluble 9-methyl benzotriazolyl carbonate fluorene polymer of structure (II) has a structure:

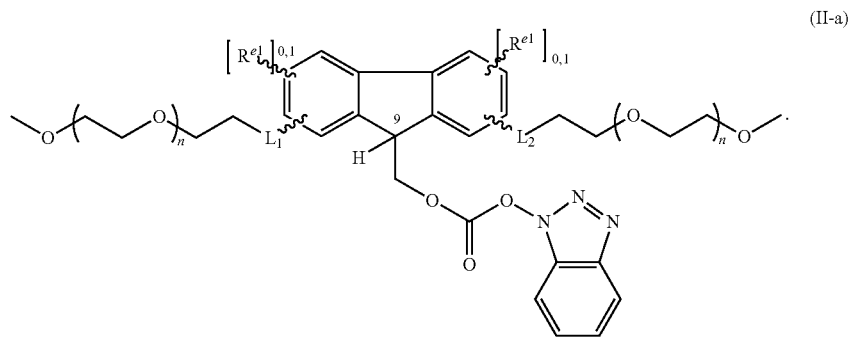

38. A method for preparing an N-hydroxyl succinimidyl carbonate ester-activated polymeric reagent, said method comprising:

reacting a water-soluble 9-hydroxymethyl fluorene polymer having a structure:

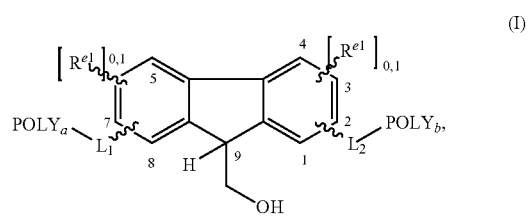

wherein

POLY$_a$ is a first water-soluble, non-peptidic polymer;

POLY$_b$ is a second, water-soluble non-peptidic polymer;

$R^{e1}$, when present, is a first electron-altering group;

$R^{e2}$, when present, is a second electron-altering group;

$L_1$ is a first linking moiety;

$L_2$ is a second linking moiety;

$R^{e1}$, which may or may not be present, is a first electron-altering group; and $R^{e2}$, which may or may not be present, is a second electron-altering group;

with from about 1 to 20 equivalents of disuccinimidyl carbonate in an anhydrous aprotic organic solvent in the presence of a base to provide a reaction mixture comprising a water-soluble 9-methyl N-hydroxysuccinimidyl carbonate fluorene polymer having a structure:

(III)

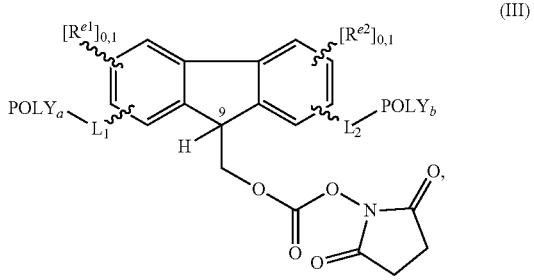

(III)

wherein POLY$_a$, POLY$_b$, R$^{e1}$, R$^{e2}$, L$_1$, and L$_2$ each have values as described in step (i);
and (ii) recovering the water-soluble 9-methyl N-hydroxysuccinimidyl carbonate fluorene polymer of structure (III) from the reaction mixture.

39. The method of claim 38, wherein prior to reacting step (i), the water-soluble 9-hydroxymethyl fluorene polymer is dissolved in the anhydrous aprotic organic solvent to provide a polymer solution, followed by drying the polymer solution to remove water that may be present to provide a dried polymer solution having less than 500 ppm water content.

40. The method of claim 39, wherein the drying is repeated until a dried polymer solution having a water content of less than 200 ppm or less than 100 ppm is attained.

41. The method of claim 39, wherein the drying step comprises azeotropically distilling the polymer solution.

42. The method of claim 39, wherein said drying is repeated until the water content of the polymer solution remains constant.

43. The method of claim 38, wherein the base is a non-nucleophilic or a weakly nucleophilic amine.

44. The method of claim 43, wherein the base is selected from the group consisting of pyridine, 4-dimethylaminopyridine, N,N-diisopropylethylamine, 2,6-di-tert-butylpyridine, N-methylimidazole, N-methylmorpholine, 2,6-lutidine, 2,4,6-collidine, N,N,2,6-tetramethylpyridine-4-amine, N,N,N',N'-tetramethyl-1,6-hexamethyldiamine, N,N',N',N'',N''-pentamethyldiethylenetriamine, hexamethylenetetramine and insoluble-polymer-bound forms of any of the foregoing.

45. The method of claim 38, wherein step (i) comprises from about 1 to about 15 equivalents of base.

46. The method of claim 45, wherein step (i) comprises from about 3 to about 10 equivalents of base.

47. The method of claim 38, wherein step (i) is carried out under a dry and inert atmosphere.

48. The method of claim 38, wherein the reacting step (i) comprises adding the disuccinimidyl carbonate to a solution of the water-soluble 9-methyl N-hydroxysuccinimidyl carbonate fluorene polymer in the anhydrous aprotic organic solvent while maintaining a temperature of from about 0 to about 30° C.

49. The method of claim 48, wherein said reacting step (i) further comprises, following the adding step, adjusting the temperature of the reaction mixture to between about 7.5 to about 18° C., followed by addition of base.

50. The method of claim 38, wherein step (i) is carried out with mixing.

51. The method of claim 50, wherein during said mixing, the temperature of the reaction mixture is maintained in a range between about 3° C. to about 21° C.

52. The method of claim 38, further comprising, prior to said recovering step, adding an acid to the reaction mixture from step (i) in an amount effective to neutralize the base.

53. The method of claim 52, where the acid is selected from the group consisting of acetic acid, phosphoric acid, citric acid, sodium dibasic phosphoric acid, potassium hydrogen phosphate, sulfuric acid, meta-nitrobenzoic acid, trifluoroacetic acid, p-toluenesulfonic acid, and trichloroacetic acid.

54. The method of claim 53, wherein the acid is selected from acetic acid, citric acid and phosphoric acid.

55. The method of claim 38, wherein the recovered water-soluble 9-methyl N-hydroxysuccinimidyl carbonate fluorene polymer comprises 15 mole percent or less of a water-soluble fulvene polymer.

56. The method of claim 38, wherein said recovering step (ii) comprises (ii-a) filtering the reaction mixture to remove solids and provide a solution, followed by (ii-b) precipitating the water-soluble 9-methyl N-hydroxysuccinimidyl carbonate fluorene polymer from the solution.

57. The method of claim 56, wherein the precipitating step comprises addition of an anhydrous precipitating solvent in which the water-soluble 9-methyl N-hydroxysuccinimidyl carbonate fluorene polymer is substantially insoluble.

58. The method of claim 57, wherein the precipitating solvent is at a temperature above its freezing point and below room temperature.

59. The method of claim 57, wherein the precipitating solvent comprises a small amount of acid sufficient to essentially neutralize any remaining base.

60. The method of claim 57, wherein the precipitating solvent is selected from diethyl ether, isopropyl alcohol, methyl t-butyl ether, ethyl acetate, pentane, hexane, heptane and mixtures of the foregoing.

61. The method of claim 38, further comprising washing the recovered water-soluble 9-methyl N-hydroxysuccinimidyl carbonate fluorene polymer with an acidified precipitating solvent.

62. The method of claim 38, further comprising (iv) purifying the recovered water-soluble 9-methyl N-hydroxysuccinimidyl carbonate fluorene polymer.

63. The method of claim 62, further comprising detecting water-soluble fulvene polymer in the recovered water-soluble 9-methyl N-hydroxysuccinimidyl carbonate fluorene polymer, wherein the purifying step (iv) comprises dissolving the recovered water-soluble 9-methyl N-hydroxysuccinimidyl carbonate fluorene polymer in a solvent to provide a solution, passing the solution through a thiol-containing resin to remove any water-soluble fulvene polymer to thereby provide a purified solution, and removing solvent from the purified solution to recover purified water soluble 9-methyl N-hydroxysuccinimidyl carbonate fluorene polymer.

64. The method of claim 1, wherein the water-soluble 9-hydroxymethyl fluorene polymer of step (i) has a structure:

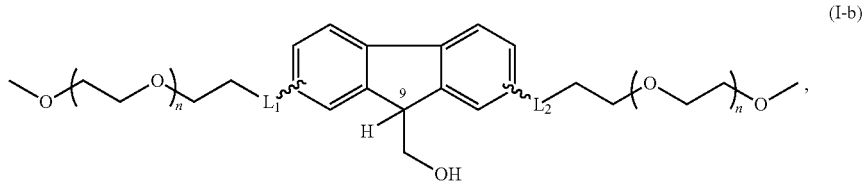
(I-b)

wherein each n is independently from about 3 to 2273, or from about 4 to about 1363, or from about 3 to about 136, or from about 136 to about 1818, or from about 113 to about 568, or from about 227 to about 568.

65. The method of claim 1, wherein the water soluble 9-hydroxymethyl fluorene polymer of step (i) has a structure:

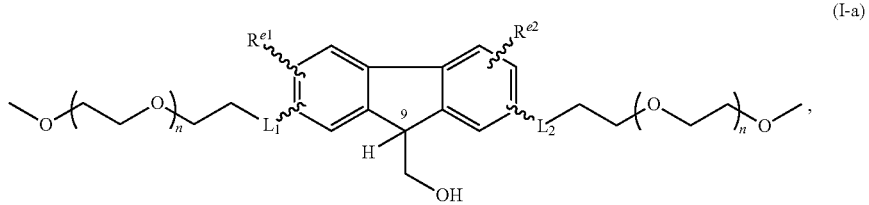
(I-a)

wherein each n is independently from about 3 to 2273, or from about 4 to about 1363, or from about 3 to about 136, or from about 136 to about 1818, or from about 113 to about 568, or from about 227 to about 568.

66. The method of claim 1, wherein the water soluble 9-hydroxymethyl fluorene polymer of step (i) has a structure:

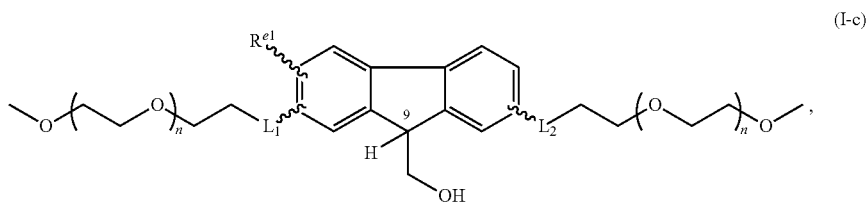
(I-c)

wherein each n is independently from about 3 to 227.

67. The method of claim 65, wherein $R^{e1}$ and $R^{e2}$ are each independently selected from halo, nitro, lower alkyl, lower alkoxy, trifluoromethyl, and —$SO_3H$.

68. The method of claim 65, wherein $L_1$ and $L_2$ each independently has a length of from 1 to 25 atoms.

69. The method of claim 65, wherein $R^{e1}$ and $R^{e2}$ are both located on the same aromatic ring.

70. The method of claim 65, wherein $R^{e1}$ and $R^{e2}$ are located on different aromatic rings.

71. The method of claim 64, wherein $L_1$ and $L_2$ are each independently selected from the group consisting of —$(CH_2)_{1-6}$C(O)NH— and —NH—C(O), NH—C(O)—$(CH_2)_{1-6}$C(O)NH—.

72. The method of claim 71, wherein $L_1$ and $L_2$ are each independently selected from the group consisting of —$(CH_2)$C(O)NH—, —$(CH_2)_3$C(O)NH—, —NH—C(O), and NH—C(O)—$(CH_2)_3$C(O)NH—.

73. The method of claim 64, wherein the weight average molecular weight of each polyethylene glycol in structure (I) is about the same (e.g., each "n" is about the same).

74. The method of claim 73, wherein each polyethylene glycol in structure (I) has a weight average molecular weight ranging from about 120 daltons to about 6,000 daltons.

75. The method of claim 73, wherein each polyethylene glycol in structure (I) has a weight average molecular weight ranging from about 6,000 daltons to about 80,000 daltons.

76. The method of claim 73, wherein each polyethylene glycol in structure (I) has a weight average molecular weight selected from the group consisting of about 5,000 daltons, 7500 daltons, 10,000 daltons, 15,000 daltons, 20,000 daltons, 30,000 daltons and 40,000 daltons.

77. The method of claim 64, where in structures (I) and (II), L1 is attached to fluorene carbon-5 and L2 is attached to fluorene carbon-2.

78. The method of claim 64, where in structures (I) and (II), L1 is attached to fluorene carbon-7 and L2 is attached to fluorene carbon-2.

79. The method of claim 64, wherein structure (I) is selected from the group consisting of:

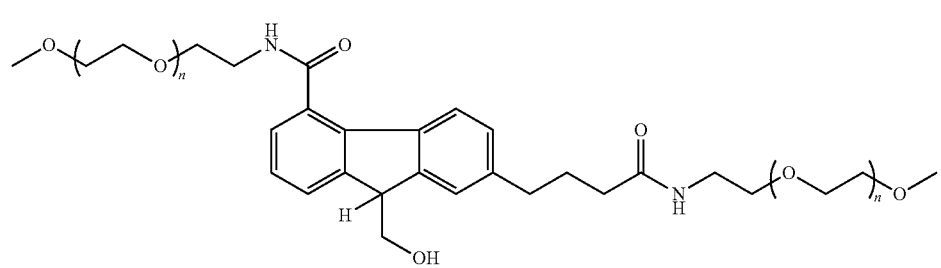
(I-d.)

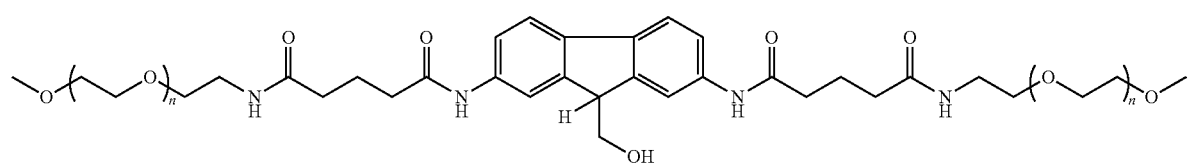
(I-e.)

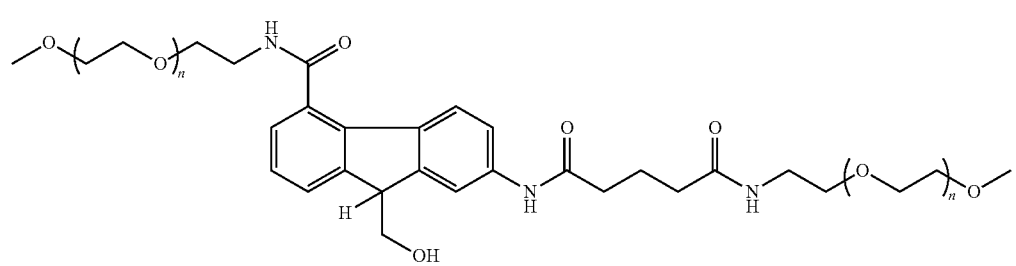
(I-f.)

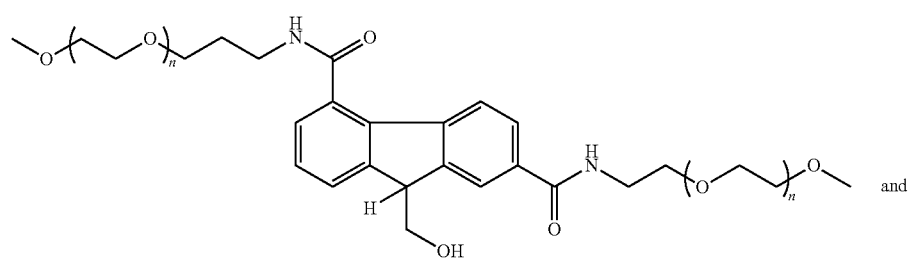
(I-g.)

and

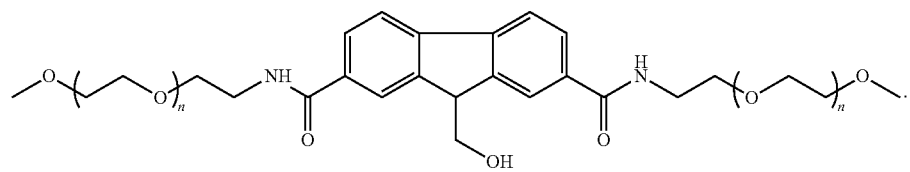
(I-h)

80. The method of claim 1, further comprising reacting the recovered or purified water-soluble 9-methyl benzotriazolyl carbonate fluorene polymer or other reactive carbonate with an amine-containing biologically active agent.

81. The method of claim 38, further comprising reacting the recovered or purified water-soluble 9-methyl N-hydroxy succinimidyl carbonate fluorene polymer with an amine-containing biologically active agent.

* * * * *